US011439688B2

(12) United States Patent
Sen Gupta et al.

(10) Patent No.: US 11,439,688 B2
(45) Date of Patent: *Sep. 13, 2022

(54) SYNTHETIC PLATELETS

(71) Applicant: CASE WESTERN RESERVE UNIVERSITY, Cleveland, OH (US)

(72) Inventors: Anirban Sen Gupta, Cleveland, OH (US); Christa Pawloski, Seven Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/590,045

(22) Filed: Oct. 1, 2019

(65) Prior Publication Data

US 2020/0030416 A1    Jan. 30, 2020

Related U.S. Application Data

(63) Continuation of application No. 16/017,174, filed on Jun. 25, 2018, now Pat. No. 10,426,820, which is a continuation-in-part of application No. 15/584,793, filed on May 2, 2017, now Pat. No. 10,434,149, which is a continuation-in-part of application No. 14/826,387, filed on Aug. 14, 2015, now Pat. No. 9,636,383, which is a continuation of application No. 14/111,650, filed as application No. PCT/US2012/033444 on Apr. 13, 2012, now Pat. No. 9,107,845.

(60) Provisional application No. 62/546,312, filed on Aug. 16, 2017, provisional application No. 62/524,265, filed on Jun. 23, 2017, provisional application No. 61/475,039, filed on Apr. 13, 2011.

(51) Int. Cl.

| | |
|---|---|
| *A61K 38/39* | (2006.01) |
| *A61K 9/127* | (2006.01) |
| *A61K 9/48* | (2006.01) |
| *A61K 47/69* | (2017.01) |
| *C07K 14/745* | (2006.01) |
| *A61K 38/00* | (2006.01) |
| *A61K 38/17* | (2006.01) |
| *A61K 47/62* | (2017.01) |
| *A61K 9/00* | (2006.01) |
| *A61K 9/19* | (2006.01) |
| *A61K 38/18* | (2006.01) |
| *C07K 14/195* | (2006.01) |
| *C07K 14/705* | (2006.01) |
| *C07K 14/78* | (2006.01) |
| *B82Y 5/00* | (2011.01) |

(52) U.S. Cl.
CPC ............ *A61K 38/39* (2013.01); *A61K 9/0019* (2013.01); *A61K 9/127* (2013.01); *A61K 9/1271* (2013.01); *A61K 9/19* (2013.01); *A61K 9/4825* (2013.01); *A61K 38/00* (2013.01); *A61K 38/177* (2013.01); *A61K 38/1774* (2013.01); *A61K 38/185* (2013.01); *A61K 47/62* (2017.08); *A61K 47/6911* (2017.08); *C07K 14/195* (2013.01); *C07K 14/70596* (2013.01); *C07K 14/745* (2013.01); *C07K 14/78* (2013.01); *B82Y 5/00* (2013.01)

(58) Field of Classification Search
None
See application file for complete search history.

(56) References Cited

U.S. PATENT DOCUMENTS

| | | | | |
|---|---|---|---|---|
| 9,107,845 | B2 * | 8/2015 | Gupta | C07K 14/745 |
| 9,636,383 | B2 * | 5/2017 | Sen Gupta | A61K 38/177 |
| 10,426,820 | B2 * | 10/2019 | Sen Gupta | A61K 9/19 |
| 10,434,149 | B2 * | 10/2019 | Gupta | C07K 14/705 |
| 2007/0059376 | A1 | 3/2007 | Takeoka et al. | |
| 2008/0213369 | A1 | 9/2008 | Gyongyossy-Issa et al. | |
| 2021/0008223 | A1 | 1/2021 | Mitragotri et al. | |

FOREIGN PATENT DOCUMENTS

| | | | |
|---|---|---|---|
| WO | WO 2010/008792 | * | 1/2010 |
| WO | WO 2017/040976 | * | 3/2017 |

OTHER PUBLICATIONS

Stein et al. (J Trauma. 2009;66:63-75) (Year: 2009).*
Mann et al. (Nat Commun. Jun. 28, 2016;7:11980) (Year: 2016).*
Palange et al. (Mol Ther . Jul. 5, 2017;25(7):1514-1521, Epub Mar. 22, 2017) (Year: 2017).*
Scordino (downloaded on Jul. 10, 2020 from URL:< https://imagebank.hematology.org/image/60932/normal-platelet) (Year: 2020).*
Ruozi et al. (Mol Neurobiol (2015) 52:899-912) (Year: 2015).*

* cited by examiner

*Primary Examiner* — Sergio Coffa
(74) *Attorney, Agent, or Firm* — Tarolli, Sundheim, Covell & Tummino LLP

(57) ABSTRACT

A synthetic platelet including a biocompatible flexible nanoparticle, the nanoparticle having an outer surface and a plurality of site targeted peptides conjugated to the surface, the synthetic platelet also including a therapeutic agent, wherein the therapeutic agent is encapsulated by the nanoparticle, wherein the synthetic platelet adheres to the site targeted and promotes delivery of the therapeutic agent onto sites of the synthetic platelet adhesion, and wherein the therapeutic agent is released at the site targeted via a site-relevant enzyme.

9 Claims, 45 Drawing Sheets

Specification includes a Sequence Listing.

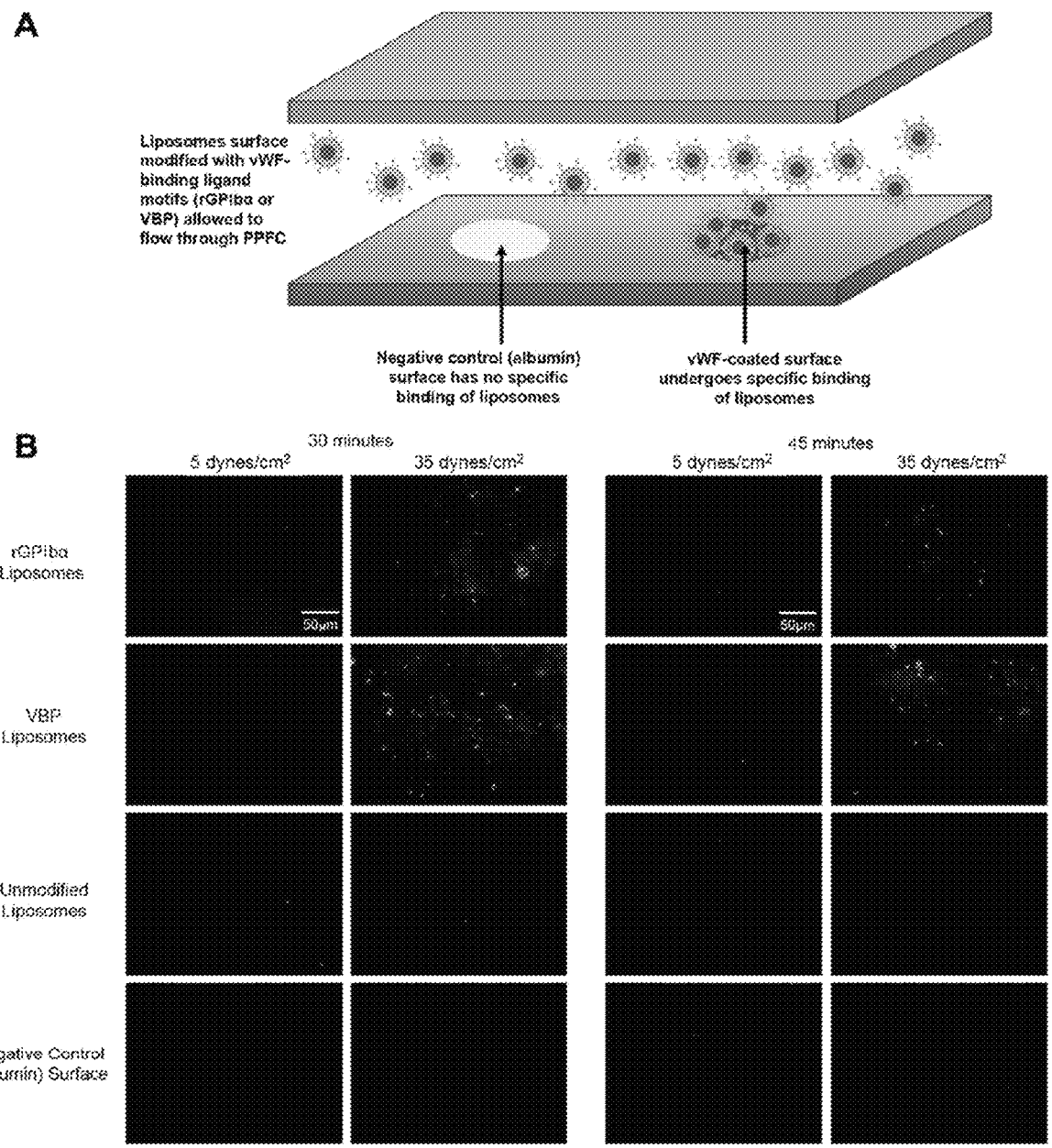
Figs. 3A-B

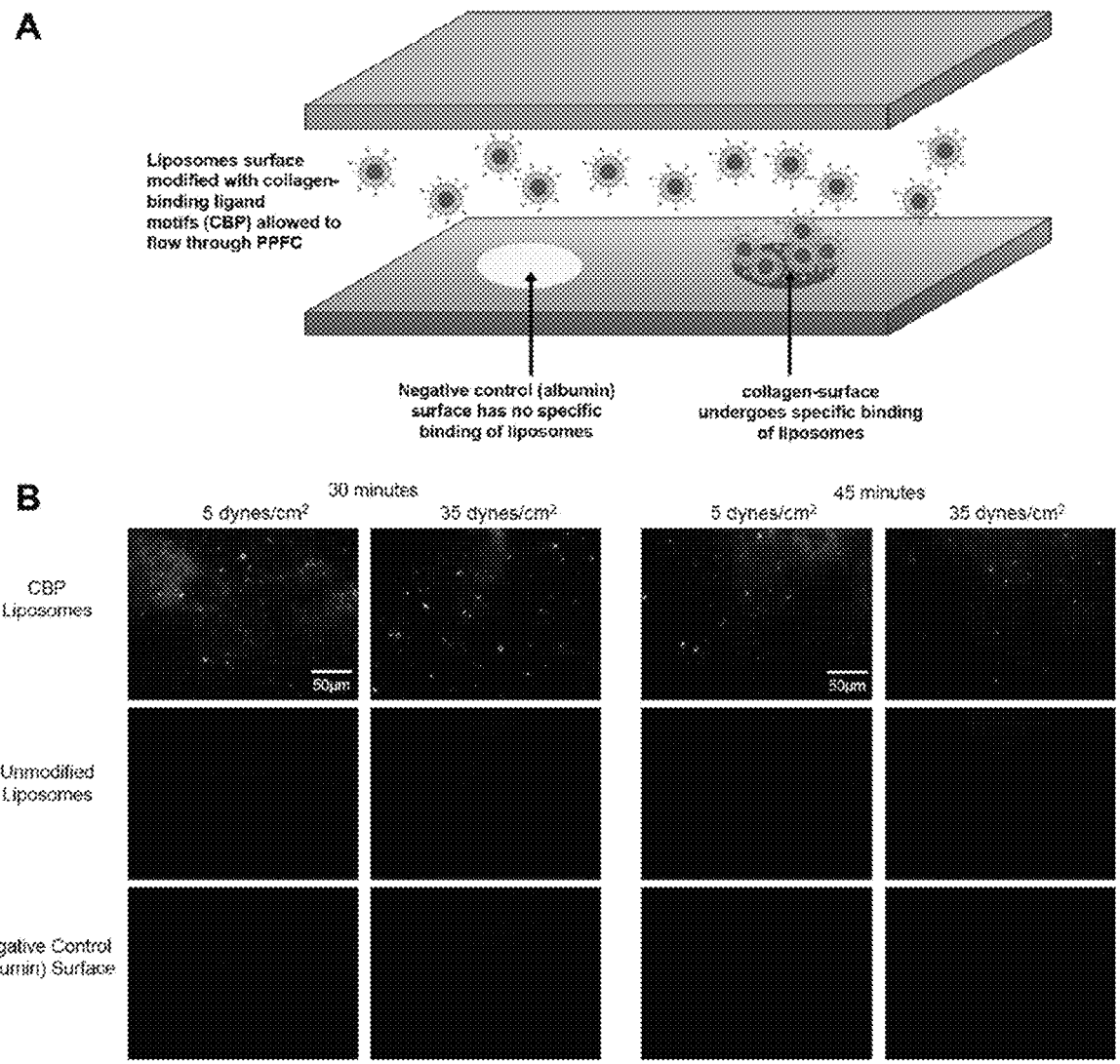
Figs. 5A-B

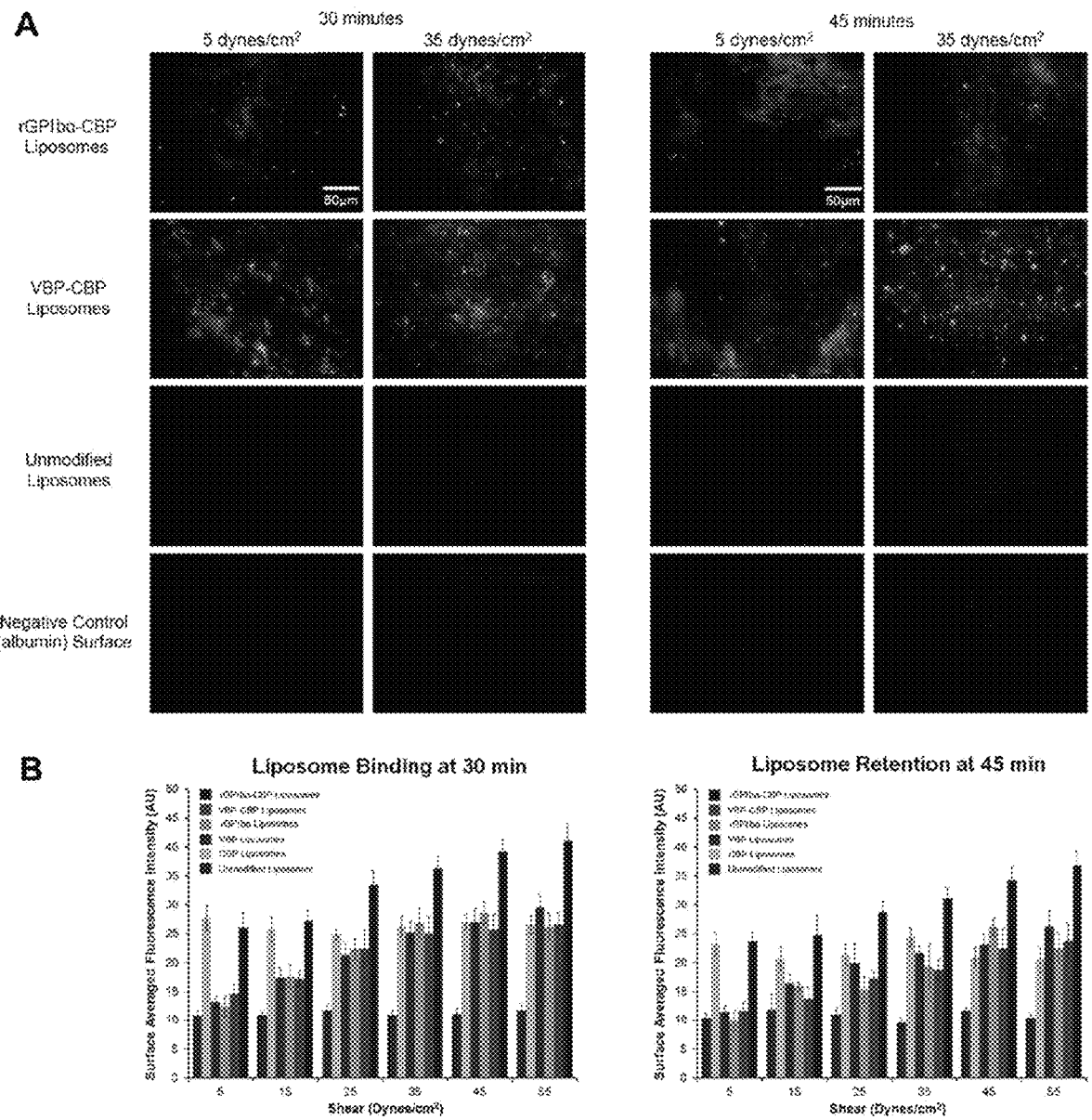
Figs. 6A-B

B

C

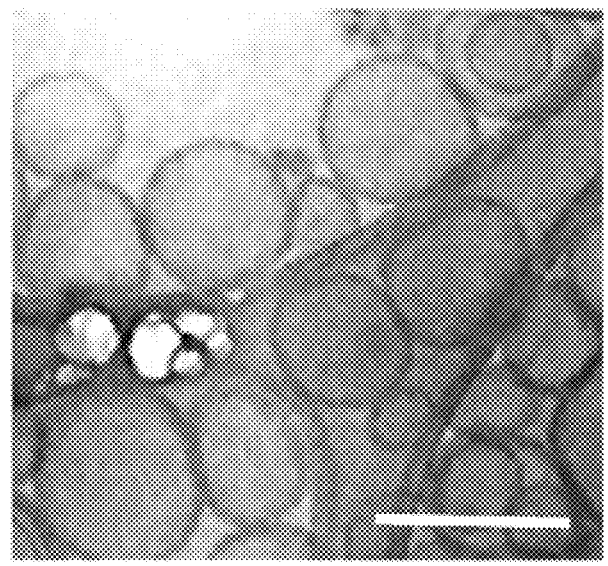
Fig. 13D
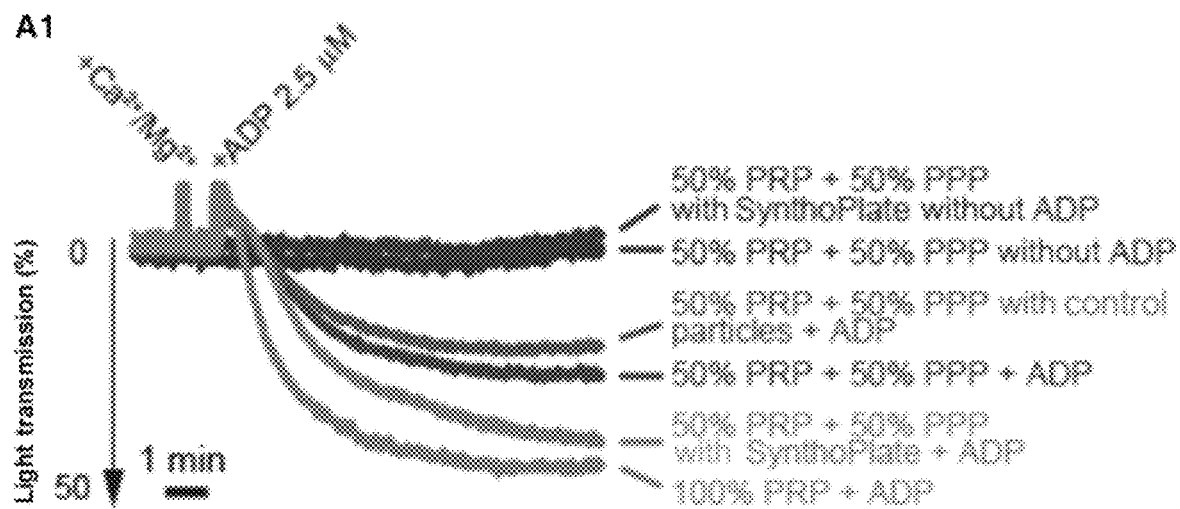
Fig. 14A1

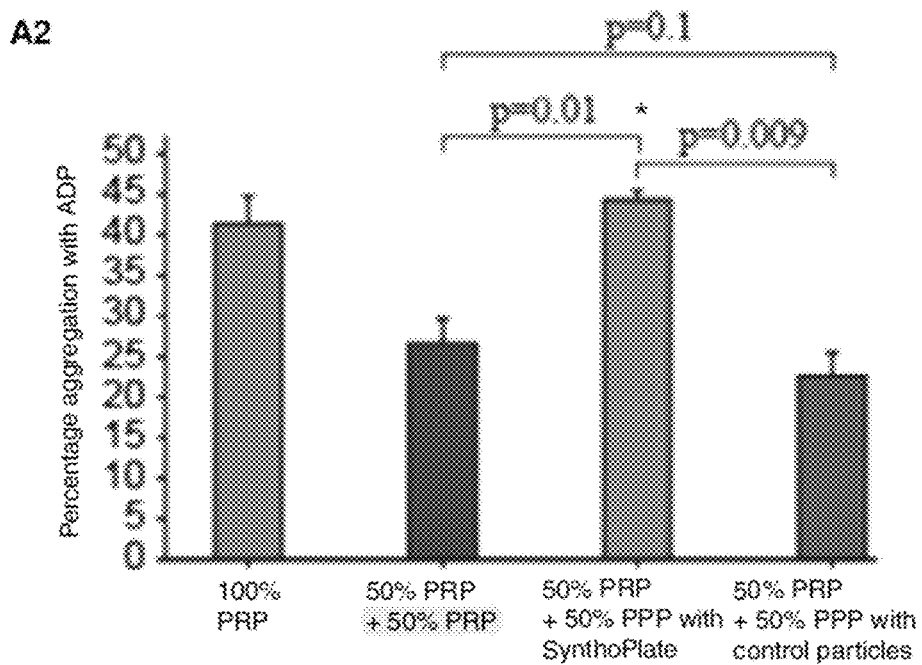
Fig. 14A2
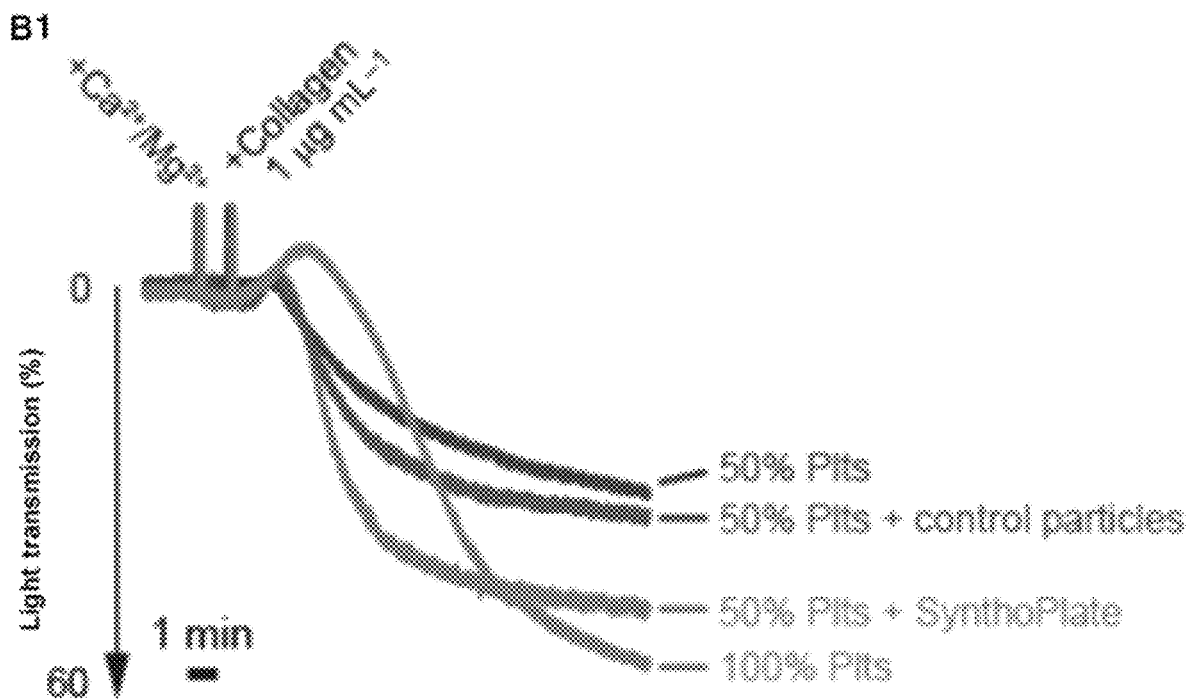
Fig. 14B1

Fig. 14B2

| GROUPS | Lag time (min) | Time to peak (min) | Maximum thrombin activity slope/s |
|---|---|---|---|
| PPP | 20 ± 3.51 | 24.33 ± 1.86 | 21.67 ± 1.67 |
| PRP | 33.33 ± 1.20 | 46.33 ± 5.46 | 22.78 ± 2.42 |
| PPP + SynthoPlate | 27.67 ± 3.84 | 31 ± 3.46 | 22.22 ± 1.47 |
| PRP + SynthoPlate | 34.33 ± 1.86 | 40.67 ± 1.86 | 25.56 ± 7.22 |
| PPP +tissue factor | 1 ± 0 | 3.33 ± 0.88 | 77.22 ± 7.47 |
| PRP +tissue factor | 1 ± 0 | 3.67 ± 1.20 | 92.22 ± 2.94 |
| PRP + SynthoPlate + Tissue Factor | 1 ± 0 | 5.33 ± 1.76 | 88.89 ± 13.14 |
| PRP + ADP + Tissue Factor | 1.33 ± 0.33 | 3.33 ± 0.67 | 117.22 ± 11.40 |
| PRP + ADP + SynthoPlate + Tissue Factor | 1.33 ± 0.33 | 4 ± 0.57 | 124.44 ± 9.15 |

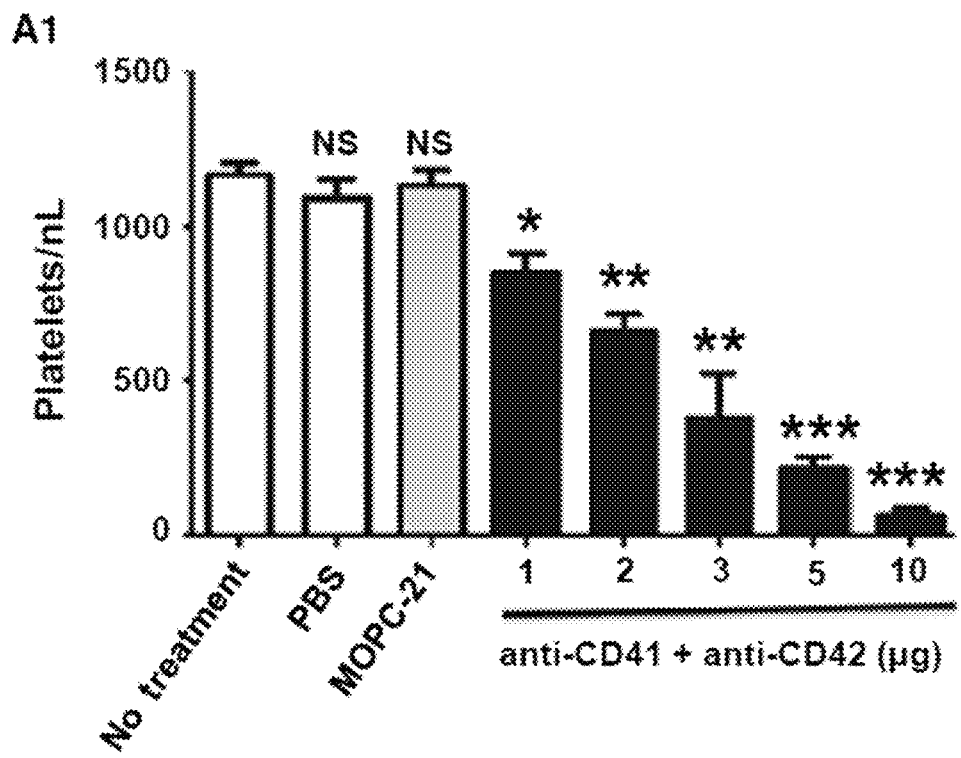
Fig. 16A1
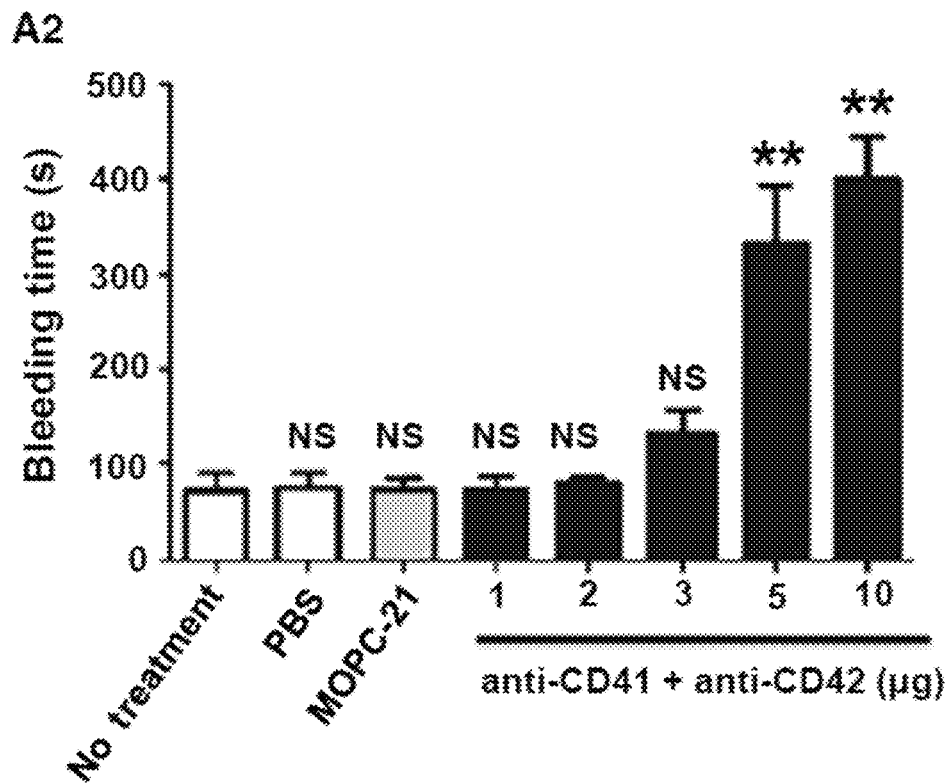
Fig. 16A2

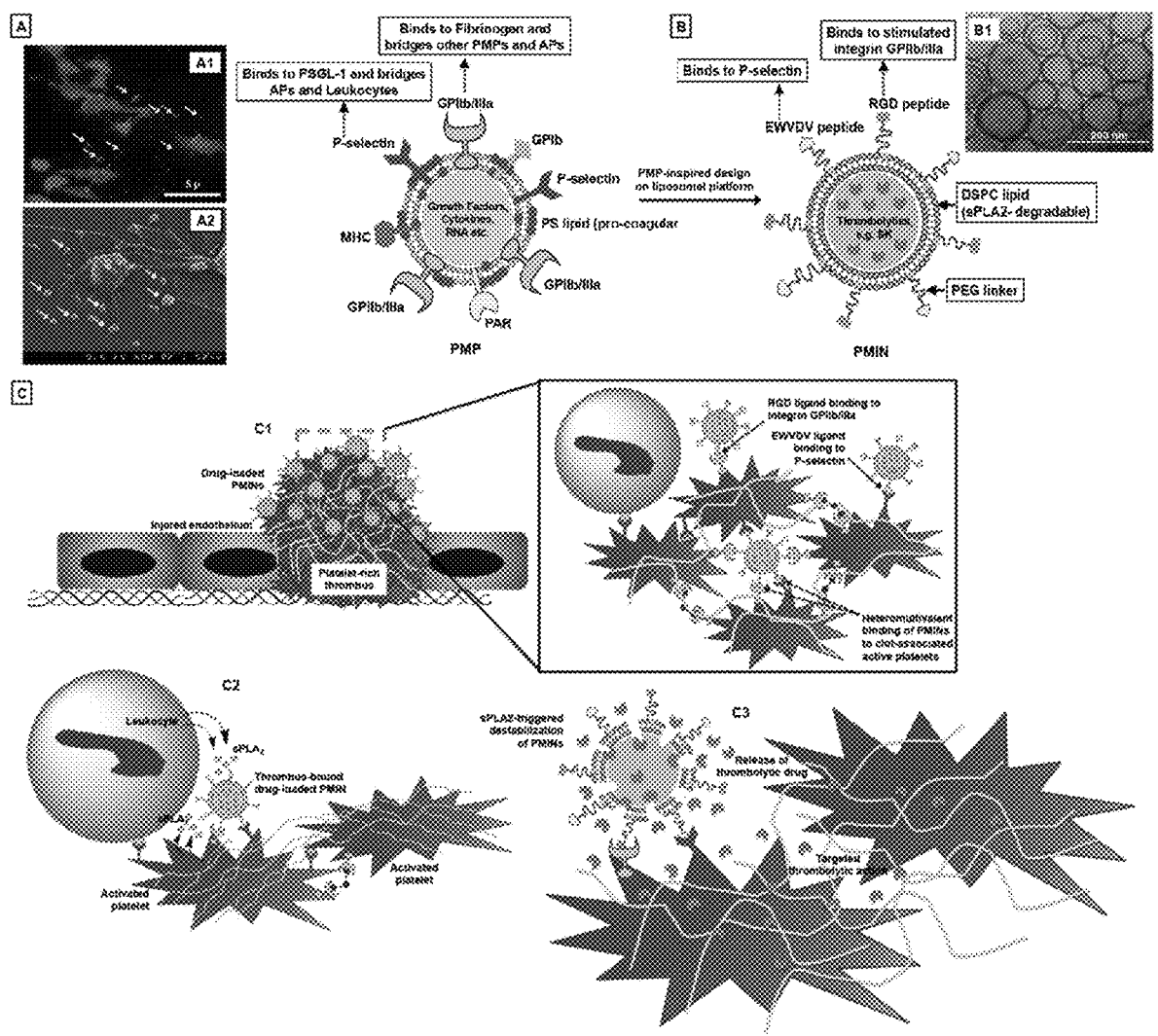
Figs. 19A-C

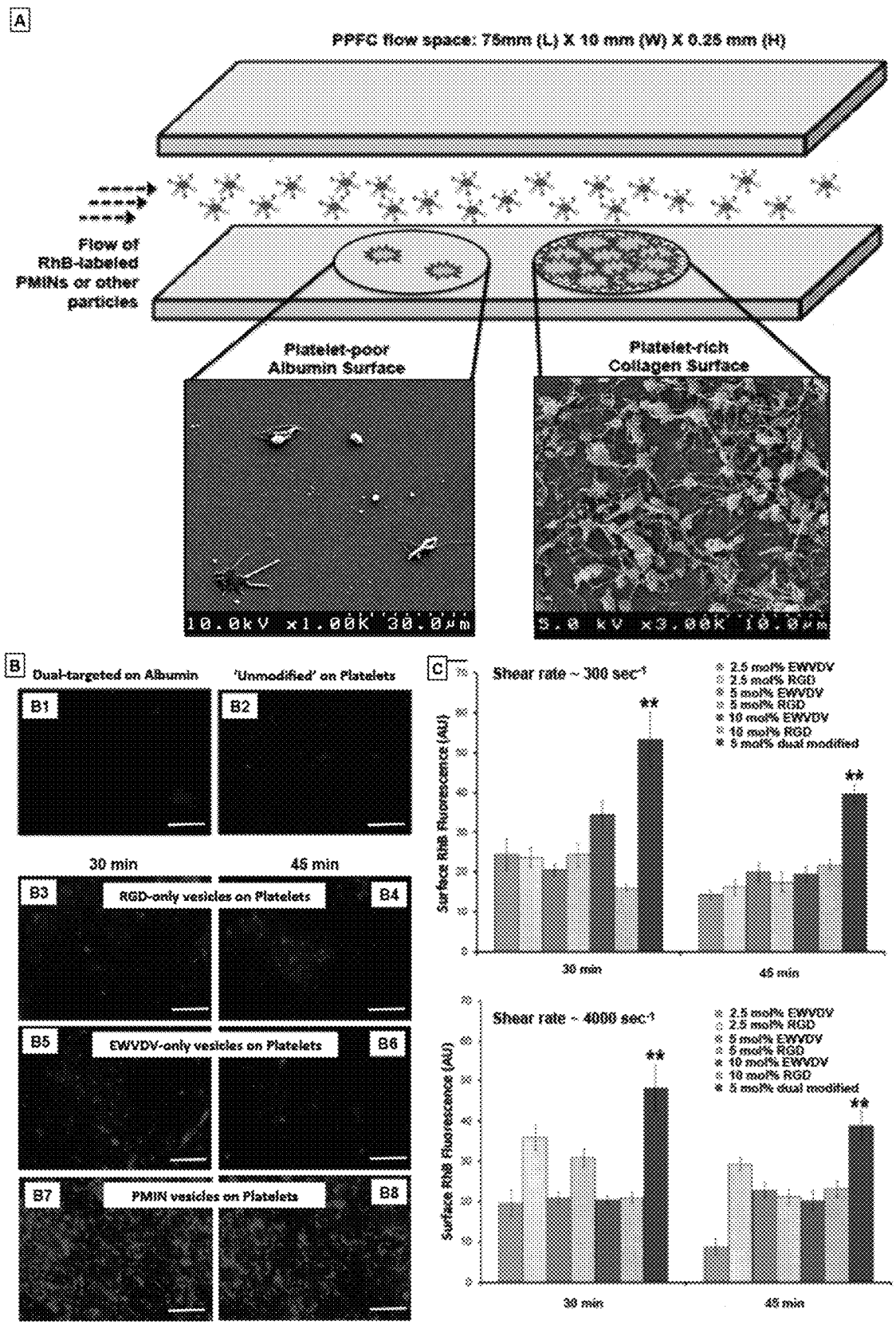
Figs. 21A-C

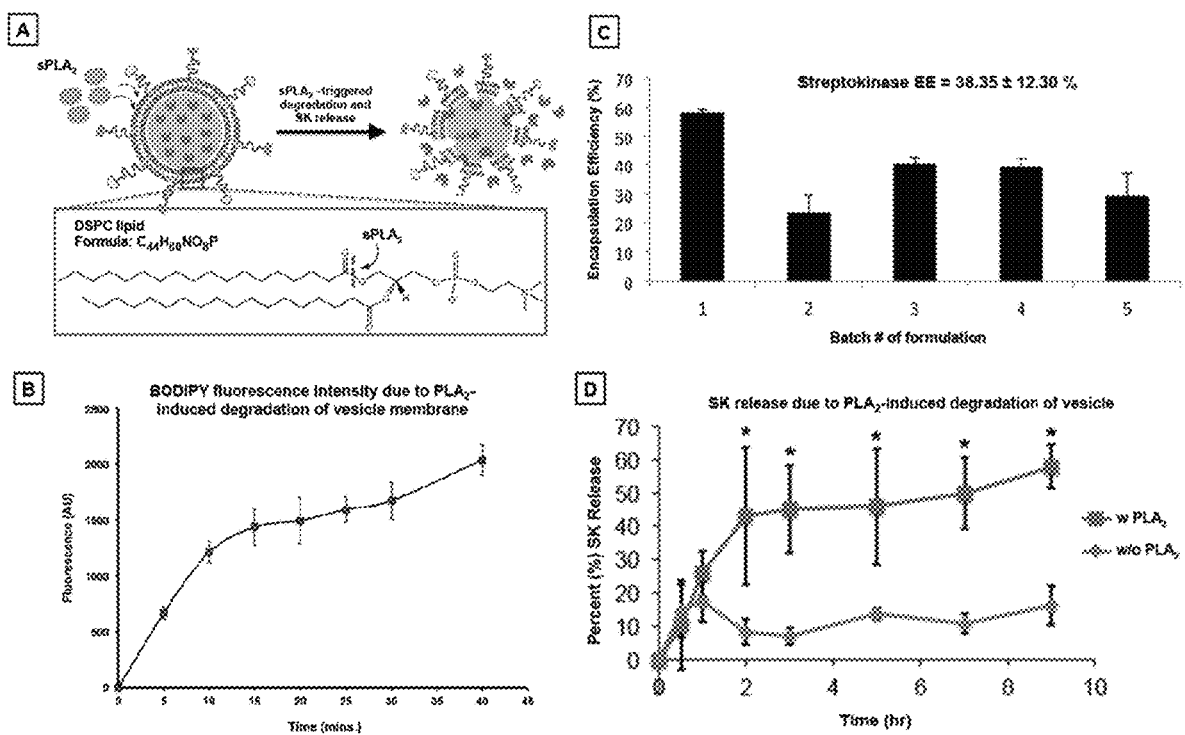
Figs. 22A-D

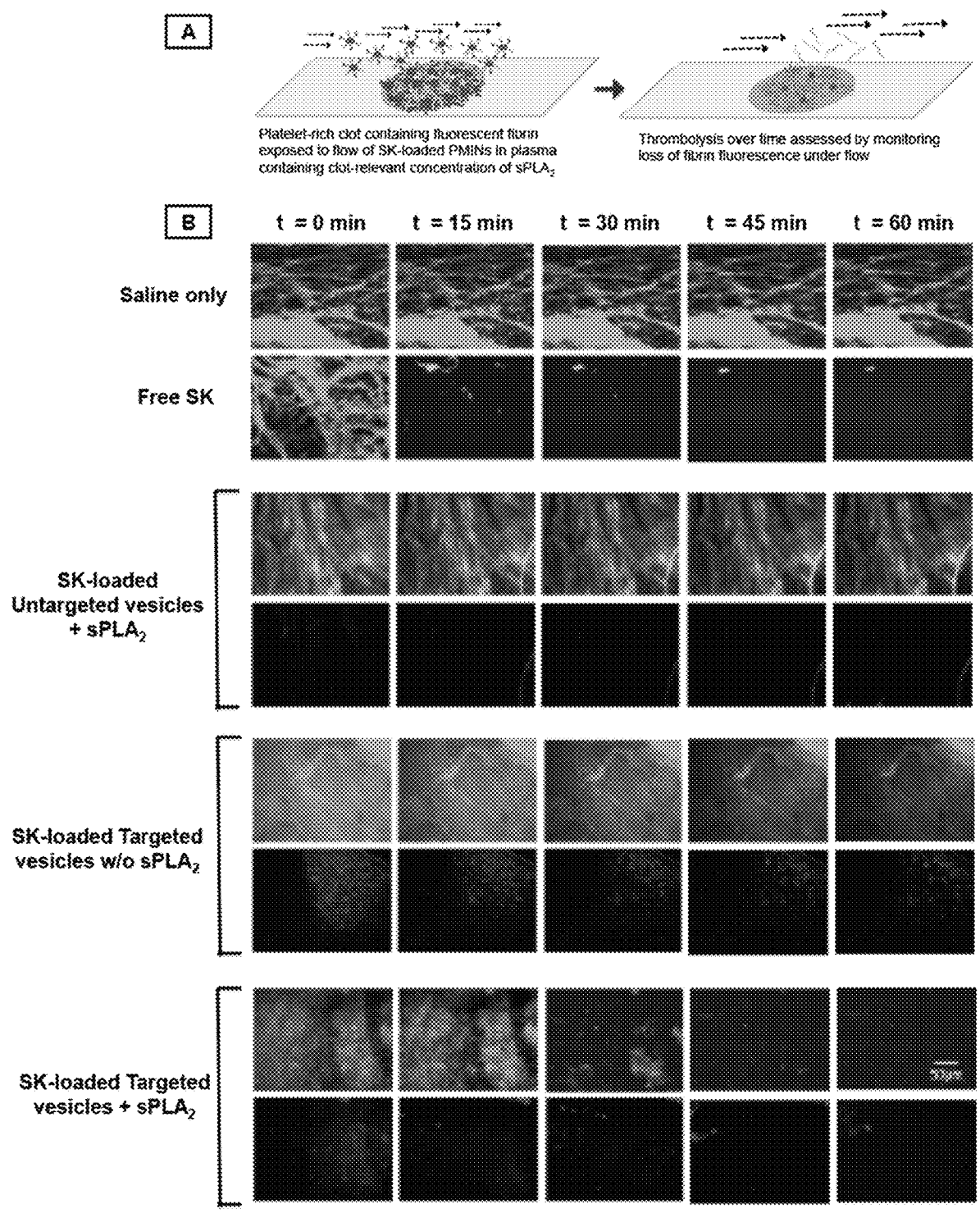
Figs. 23A-B

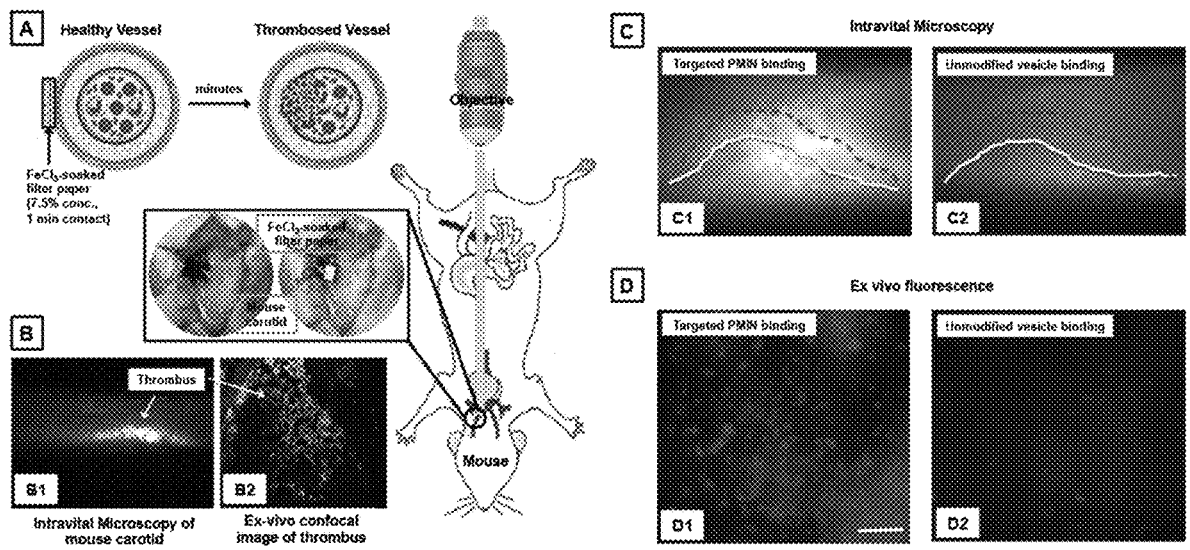
Figs. 24A-D
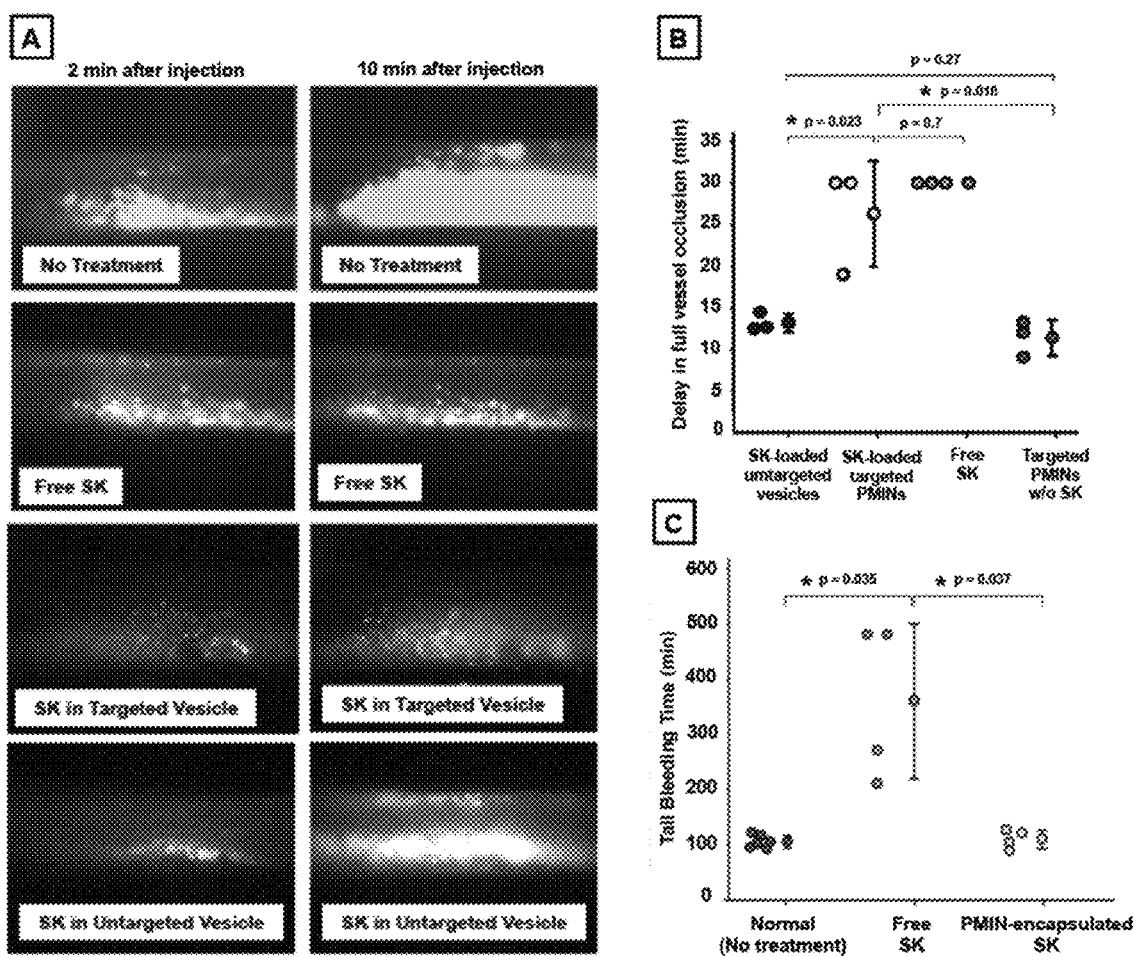
Figs. 25A-C

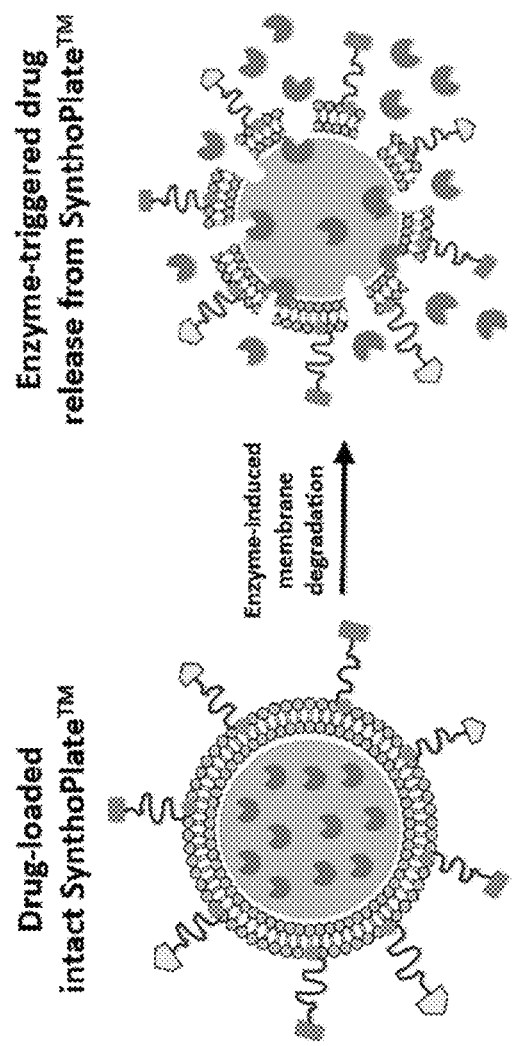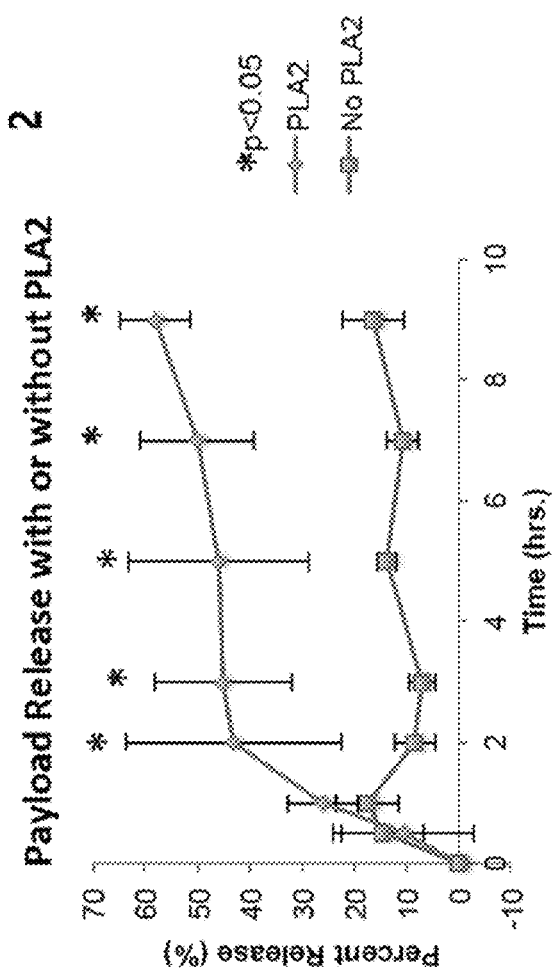
Fig. 29

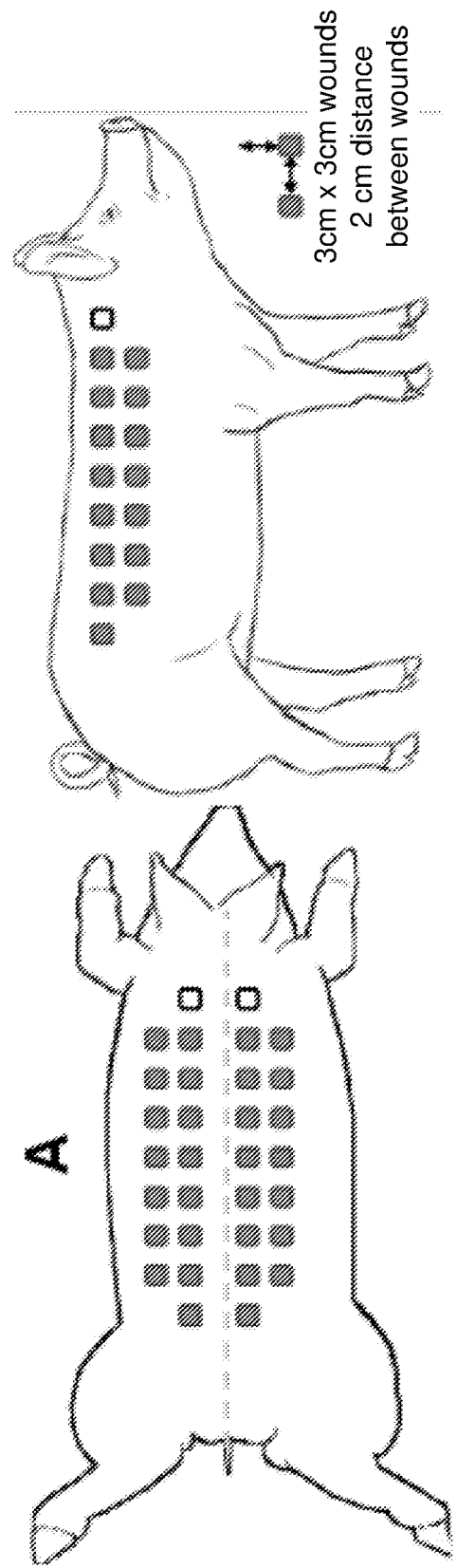
Fig. 32A
Fig. 32B

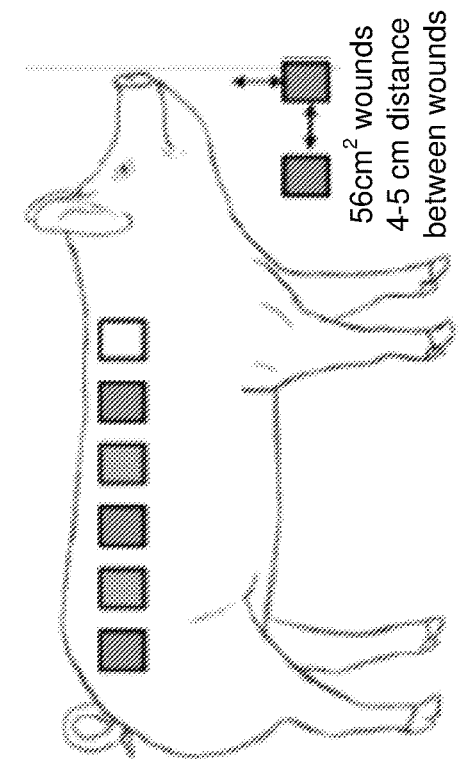
Fig. 33A
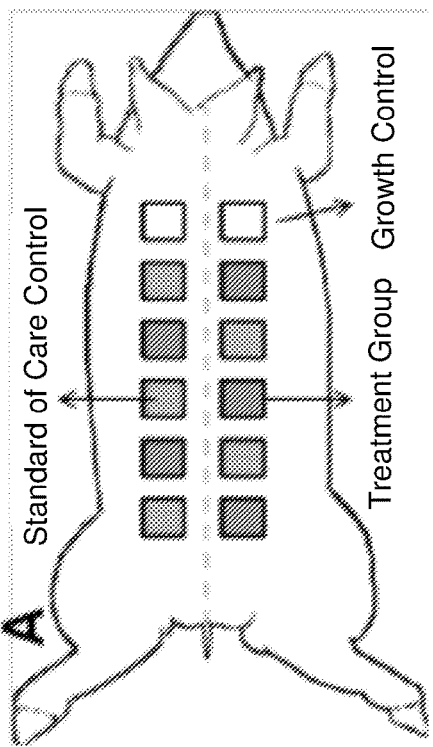
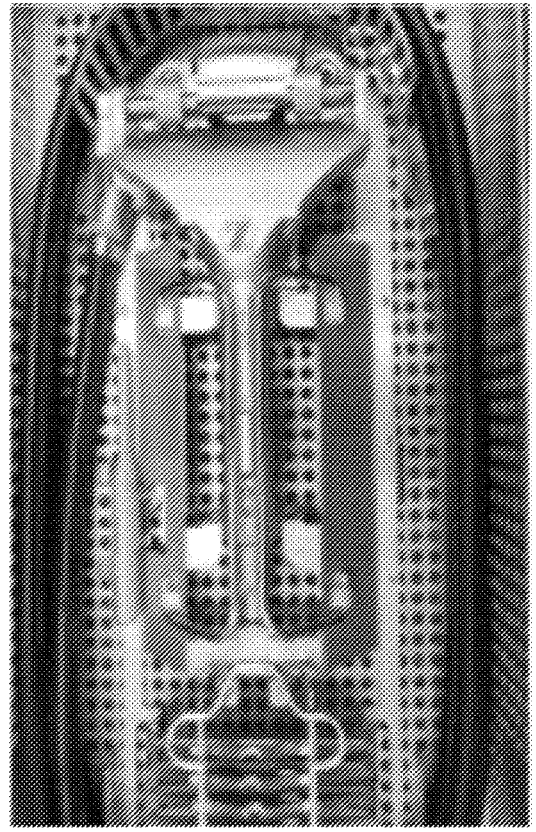
Fig. 33B

SEQUENCE LISTING

```
<160> NUMBER OF SEQ ID NOS: 3

<210> SEQ ID NO 1
<211> LENGTH: 15
<212> TYPE: PRT
<213> ORGANISM: Homo sapiens

<400> SEQUENCE: 1

Thr Arg Tyr Leu Arg Ile His Pro Gln Ser Trp Val His Gln Ile
1               5                   10                  15

<210> SEQ ID NO 2
<211> LENGTH: 21
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: 4HYP 4-Hydroxyproline
<220> FEATURE:
<221> NAME/KEY: MISC_FEATURE
<222> LOCATION: (6)..(6)
<223> OTHER INFORMATION: 4HYP 4-Hydroxyproline
<220> FEATURE:
<221> NAME/KEY: MISC_FEATURE
<222> LOCATION: (9)..(9)
<223> OTHER INFORMATION: 4HYP 4-Hydroxyproline
<220> FEATURE:
<221> NAME/KEY: MISC_FEATURE
<222> LOCATION: (12)..(12)
<223> OTHER INFORMATION: 4HYP 4-Hydroxyproline
<220> FEATURE:
<221> NAME/KEY: MISC_FEATURE
<222> LOCATION: (15)..(15)
<223> OTHER INFORMATION: 4HYP 4-Hydroxyproline
<220> FEATURE:
<221> NAME/KEY: MISC_FEATURE
<222> LOCATION: (18)..(18)
<223> OTHER INFORMATION: 4HYP 4-Hydroxyproline
<220> FEATURE:
<221> NAME/KEY: MISC_FEATURE
<222> LOCATION: (21)..(21)
<223> OTHER INFORMATION: 4HYP 4-Hydroxyproline

<400> SEQUENCE: 2

Gly Pro Xaa Gly Pro Xaa Gly Pro Xaa Gly Pro Xaa Gly Pro Xaa Gly
1               5                   10                  15
```

```
Pro Xaa Gly Pro Xaa
            20

<210> SEQ ID NO 3
<211> LENGTH: 9
<212> TYPE: PRT
<213> ORGANISM: Homo sapiens

<400> SEQUENCE: 3

Cys Asn Pro Arg Gly Asp Tyr Arg Cys
1               5
```

SYNTHETIC PLATELETS

RELATED APPLICATION

This application claims priority to U.S. Provisional Application No. 62/524,265, filed Jun. 23, 2017, this application is also a Continuation-in-Part of U.S. patent application Ser. No. 15/584,793, which is a Continuation-in-Part of U.S. patent application Ser. No. 14/826,387, filed Aug. 14, 2015, now U.S. Pat. No. 9,686,383, which is a Continuation of U.S. patent application Ser. No. 14/111,650, filed Dec. 18, 2013, now U.S. Pat. No. 9,107,845, which is a National Phase filing of PCT/US2012/033444, filed Apr. 13, 2012, which claims priority from U.S. Provisional Application No. 61/475,039, filed Apr. 13, 2011, the subject matter of which are incorporated herein by reference in their entirety.

GOVERNMENT FUNDING

This invention was made with government support under Grant No. F31-DE019998, R01HL121212, R01HL089796 awarded by The National Institutes of Health. R35GM119526, awarded by the National Institute of General Science. The United States government has certain rights in the invention.

TECHNICAL FIELD

This application relates to compositions and methods of treating injuries and conditions and particularly relates to synthetic platelets and to their use in treating vascular injuries and conditions.

BACKGROUND

Traumatic injury is the leading cause of death for individuals between the ages of 5 and 44, and blood loss is the major factor in both civilian and battlefield traumas. Following injury, hemostasis is established through a series of coagulatory events including platelet activation. However, with severe injuries, these processes are insufficient and result in uncontrolled bleeding. Methods to staunch bleeding have included pressure dressings and absorbent materials, but these treatments are limited to compressible and exposed wounds. Alternatives have included allogeneic platelet transfusions, clotting factors, and platelet substitutes, but efficacy, immunogenicity, and thrombosis have stalled their application. Immediate intervention is one of the most effective means of minimizing mortality associated with severe trauma.

Administration of allogenic platelets are a logical means to halt bleeding; however, platelets have a short shelf life, and administration of allogenic platelets can cause graft versus host disease, alloimmunization, and transfusion-associated lung injuries. Recombinant factors including Factor VIIa can augment hemostasis, but immunogenic and thromboembolic complications are unavoidable risks. Nonetheless, administration of recombinant factors has become the standard of care in a number of trauma and surgical situations where bleeding cannot otherwise be controlled. Non-platelet alternatives including red blood cells modified with the Arg-Gly-Asp (RGD) sequence, fibrinogen-coated microcapsules based on albumin, and liposomal systems have been studied as coagulants, but toxicity, thrombosis, and limited efficacy have stalled many of these products.

SUMMARY

This application relates to a synthetic platelet that includes a biocompatible flexible nanoparticle. The nanoparticle includes an outer surface and a plurality of site targeted peptides conjugated to the surface. The synthetic platelet also includes a therapeutic agent. The therapeutic agent can be encapsulated and/or conjugated to by the nanoparticle. The synthetic platelet adheres to the site targeted and promotes delivery of the therapeutic agent onto sites of the synthetic platelet adhesion. The therapeutic agent can be released at the site targeted via a site-relevant enzyme, which cleaves or destabilizes the nanoparticle to release the therapeutic agent.

The site targeted peptides can be spatially or topographically arranged on the flexible nanoparticle surface such that the site targeted peptides do not spatially mask each other and the synthetic platelet is able to adhere to a targeted site.

In some embodiments, the flexible nanoparticle shape, size and/or elastic modulus upon administration to a vasculature of a subject can facilitate margination to a vascular wall and bio-interaction with cells of the vascular wall. For example, the flexible nanoparticle can have an about 2 to about 5 μm diameter discoidal shape and an about 10 to about 50 kPa mechanical elastic modulus.

In some embodiments, the nanoparticle can include a liposome. In other embodiments, the nanoparticle can include an outer shell that comprises alternating layers of albumin and a polyallyamine.

In some embodiments, the plurality of peptides can include a plurality of von Willebrand factor-binding peptides (VBPs), collagen-binding peptides (CBPs) and active platelet GPIIb-IIIa-binding peptides (GBPs), wherein the synthetic platelet adheres to a vascular surface, vascular disease site, and/or vascular injury site with exposed von Willebrand factor and collagen, promotes arrest and aggregation of active platelets onto sites of the synthetic platelet adhesion, and promotes delivery of the therapeutic agent onto sites of the synthetic platelet adhesion.

In some embodiments, the therapeutic agent can be selected from the group consisting of an anti-fibrinolytic agent, a fibrin crosslinking agent, a coagulation-promoting agent, a wound healing agent, an anti-infective agent, an anti-inflammatory agent and combinations thereof.

In some embodiments, the VBPs can include a peptide having SEQ ID NO: 1, the CBPs can include a peptide having SEQ ID NO: 2, and the GBPs can include a peptide having SEQ ID NO: 3.

In other embodiments, the ratio of VPBs to CPBs provided on the nanoparticle surface is about 70:30 to about 30:70. In still other embodiments, the ratio of VPB:CPB:GBP is about 1:1:2 to 1:2:1 to 2:1:1.

In other embodiments, the plurality of peptides can include a plurality of active platelet GPIIb-IIIa-binding peptides (GBPs) and active platelet p-selectin binding peptides. The synthetic platelet can adhere to an active platelet rich thrombus site and promote delivery of the therapeutic agent onto sites of the active platelet rich thrombus. The GBPs can include a peptide having SEQ ID NO: 4 and the p-selectin binding peptides can include a peptide having SEQ ID NO: 5. In some embodiments, the ratio of GBP: the p-selectin binding peptides is about 1:1. In some embodiments, the therapeutic agent is an anti-fibrinolytic agent.

In some embodiments, the plurality of peptides can include a plurality of brain injury site-targeted peptides. The plurality of brain injury site targeted peptides can include extracellular matrix domain (ECD) binding peptides or perineuronal net (PNN) binding peptides that bind to ECDs or PNNs rich in chondroitin sulfate proteoglycans that are upregulated at the brain injury site. The synthetic platelet can adhere to a brain injury site and promote delivery of the therapeutic agent to sites of the brain injury. The brain injury site-targeted peptides can include a peptide having the SEQ ID NO: 6.

In some embodiments, the therapeutic agent is a neuroprotective therapeutic agent. The neuroprotective therapeutic agent can be selected from the group consisting of brain-derived neurotrophic factor (BDNF), glial cell line-derived neurotrophic factor (GDNF), nerve growth factor (NGF), ciliary neurotrophic factor (CNTF), and combinations thereof.

In some embodiments, the synthetic platelets can be used in a method of treating a vascular injury. In other embodiments, the synthetic platelets can be used in a method of treating a vascular occlusive condition. In still other embodiments, the synthetic platelets can be used in a method of treating a traumatic brain injury.

BRIEF DESCRIPTION OF THE DRAWINGS

FIGS. 6(A-B) illustrate representative results from PPFC studies using heteromultivalent liposomal constructs surface-modified with both vWF-binding (rGPIbα or VBP) and collagen-binding (CBP) ligand motifs allowed to flow over vWF/collagen mixed (50:50) surface versus albumin surface. (A) The heteromultivalent ligand-modified liposomes showed minimal adhesion or retention on albumin surface and the unmodified liposomes showed minimal adhesion or retention on the vWF/collagen mixed surface, whereas, the liposomes modified simultaneously with both vWF binding and collagen-binding ligand motifs showed significant adhesion and retention on the vWF/collagen mixed surface; (B) quantitative analysis of the adhesion (at 30 min) and retention (at 45 min) data using surface-averaged fluorescence intensity shows that the liposomes surface modified simultaneously with rGPIbα and CBP (red bars) do not undergo statistically different adhesion and retention on the vWF/collagen surface compared to liposomes surface-modified with rGPIbα alone, whereas, liposomes modified with VBP and CBP (indigo bars) undergo significantly enhanced adhesion and retention on the vWF/collagen surface compared to liposomes surface-modified with VBP alone and CBP alone, under increasing shear stress.

FIGS. 14(A-B) illustrate ex vivo aggregometry studies for SynthoPlate with mouse platelets. Representative aggregometry traces (A1, B1) and corresponding per-centage platelet aggregation histograms (A2, B2) of SynthoPlate versus control (unmodified) particles for platelet-rich plasma (PRP) with ADP as agonist and a washed platelet suspension (Plts) with collagen as agonist. SynthoPlate itself does not activate and aggregate resting platelets (the brown trace is similar to the indigo trace in [A1]). Addition of platelet agonist (ADP in [A1] and collagen in [B1]) to 100% PRP or 100% Plts significantly enhances aggregation (green traces in [A1] and [B1]), but this aggregation is significantly decreased if the PRP is 50% diluted with platelet-poor plasma (PPP) or Plts is 50% diluted with phosphate-buffered saline (PBS) (purple traces in [A1] and [B1]). Addition of control (unmodified) particles in the diluting volume of PPP or Plts does not improve this aggregation (red traces in [A1] and [B1]), but addition of SynthoPlate to the diluting volume of PPP or Plts significantly improves aggregation (cyan traces in [A1] and [B1]). Corresponding histograms (A2, B2) clearly show the ability of SynthoPlate to improve percentage aggregation of ADP-activated platelets in 50% diluted PRP and of collagen-activated platelets in 50% diluted Plts.

FIGS. 19(A-C) illustrate (A) schematic images of platelet-derived microparticles (PMP) showing characteristic surface entities, with (A1) showing representative red fluorescence image of PE-anti-CD62P stained active platelets (stained for P-selectin, shown with blue arrows) shedding PMPs (shown with yellow arrows, and (A2) showing representative high resolution SEM image of active platelet shedding microparticle, with PMPs (shown with arrows) visible as sub-micron vesicular structures; (B) Schematic images of PMP inspired nanovesicle (PMIN), with (B1) showing representative cryo-TEM image of PMINs developed for the studies; (C) Envisioned mechanism of targeted thrombolytic action using PMINs, where (C1) PMINs can actively anchor onto platelet-rich thrombi by virtue of heteromultivalent binding to integrin GPIIb-IIIa and P-selectin on active platelets, (C2) clot-bound PMINs get acted upon by sPLA2 enzymes secreted from leukocytes and active platelets in the thrombus milieu and (C3) drug released from degraded PMINs renders sitespecific fibrinolysis.

FIGS. 21(A-C) illustrate a schematic image, images, and graphs showing: (A) experimental set-up of parallel plate flow chamber (PPFC) where platelet-poor albumin-coated regions (control surface) and active platelet-rich thrombus region (on collagen-coated area) were created and unmodified RhB-labeled unmodified vesicles or singly modified vesicles (bearing RGD decorations or EWVDV decorations only) or dual modified PMINs (bearing both peptide decorations) were flowed over these surfaces at various flow rates (low-to-high shear rates); (B) representative fluorescent images of particle binding shows that (B1) dual-targeted particles (i.e., PMINs) have minimal binding on albumin-coated surface and (B2) unmodified particles have minimal binding on the platelet-rich thrombus surface; (B3, B4) RGD-decorated vesicles and (B5, B6) EWVDV-decorated vesicles have reasonable extent of binding and retention on the platelet-rich thrombus surface, but the level of binding and retention levels are significantly enhanced for (B7, B8) dual modified PMINs; (C) Quantitative analysis of vesicle binding and retention (based on surface-averaged RhB fluorescence intensity) from multiple batches of experiments show that irrespective of flow conditions (low or high shear rate), dual modified vesicles (PMINs) have significantly higher binding and retention capabilities compared to singly modified vesicles even when the mol % composition of single peptide modification is to twice (10 mol %) that of dual peptide modification (5 mol %).

FIGS. 22(A-D) illustrate a schematic, graphs, and plot showing (A) mechanism of sPLA2-induced membrane degradation due to cleavage of sn-2 acyl group of the phosphatidyl choline lipids; (B) vesicle membrane degradation kinetics as monitored by measuring the increase in BODIPY fluorescence over time due to cleavage of the BODIPY moiety from the bis-BODIPY FL C11-PC due to sPLA2 action; (C) Encapsulation efficiency (EE) assessment for streptokinase (SK) encapsulation various batches of PMINs show an average EE of ~38%; [D] Release kinetics assessment of SK from PMINs with or without sPLA2 incubation shows that upon sPLA2 exposure the percent (%) release of SK from PMINs is significantly enhanced (~4 fold) compared passive release (principally via diffusion) without sPLA2 exposure.

FIGS. 23(A-B) illustrate a schematic and images showing: (A) in vitro experimental set-up where SK-loaded RhB-labeled clot-targeted PMINs (or untargeted vesicles) were flowed over platelet-rich clots containing green fluorescent fibrin, in presence (or absence) of clot-relevant concentration of sPLA2, and clot lysis was monitored by imaging fate of vesicle and clot fluorescence over time; (B) representative images where 'saline only' was unable to affect clot fluorescence while free SK caused substantial loss of clot fluorescence (hence thrombolysis); SKloaded targeted PMINs in presence of sPLA2 showed similar clot lysis along with vesicle degradation, compared to the control conditions (SK-loaded targeted vesicles w/o sPLA2 or untargeted vesicles with sPLA2).

FIGS. 24(A-D) illustrate a schematic and images showing: (A) experimental set-up and resultant clot formation in the carotid artery of mouse upon application of FeCl$_3$-soaked filter paper on the adventitial side and real-time observation of clot (thrombus) by intra-vital microscopy; (B) representative image of thrombosed carotid as observed by (B1) intravital microscopy and (B2) ex vivo immunofluorescence; (C) representative intravital microscopy images of vesicle binding to carotid thrombus upon intravenous (through jugular) administration shows that (C1) active platelet-targeted PMINs can bind to the thrombi at substantially high levels compared to (C2) unmodified vesicles (thrombus surface profile shown by yellow and dotted red lines); (D) Representative ex vivo fluorescence microscopy images of excised arteries show that (D1) targeted PMINs have high level of binding to thrombosed arteries, compared to binding of (D2) unmodified vesicles.

FIGS. 25(A-C) illustrate a schematic, images, and plots showing: (A) representative intravital microscopy images (2 min and 10 min time point post treatment injection) of Rhodamine G-labeled platelet-rich thrombi (FeCl$_3$-induced) within mouse carotid after intravenous (through jugular) administration of free SK or SK-loaded targeted PMIN vesicles or SK-loaded unmodified (untargeted) vesicles or no treatment, shows that without any treatment the artery is significantly occluded within 10 min, free SK treatment keeps the artery significantly open due to persistent thrombolysis, treatment with SK-loaded targeted PMINs shows similar thrombolytic effect as free SK, and treatment with SK-loaded untargeted vesicles have much reduced thrombolytic effect; (B) quantitative results of delay in vessel occlusion emphasizes the fact that SK-loaded targeted PMINs can delay vessel occlusion with an efficacy close to that of free SK, targeted PMINs without SK cannot effectively delay vessel occlusion, and SK-loaded untargeted vesicles are unable to delay vessel occlusion to the level of SK-loaded targeted PMINs; (C) tail bleeding studies on mouse injected with free SK versus SK-loaded PMINs show that free SK have systemic off-target effect on hemostatic capability (tail bleeding time increased significantly compared to normal 'no treatment' mice) while PMIN-encapsulated SK does not have such drastic effect.

FIG. 29 illustrates a schematic and plot showing a feasibility study of drug encapsulation and customizable slow or fast release of encapsulated drug from SynthoPlate system.

FIGS. 32(A-B) illustrate a schematic and image showing: (A) a burn Model with proposed burn sites and growth control groups; and (B) a burning Device used to produce the model: Brass block with T-Type Thermocoupler FIGS. 33(A-B) illustrate a schematic and images showing: (A) tangential excision wounds; and (B) dermatome used for making excision wounds.

DETAILED DESCRIPTION

Figure 1:
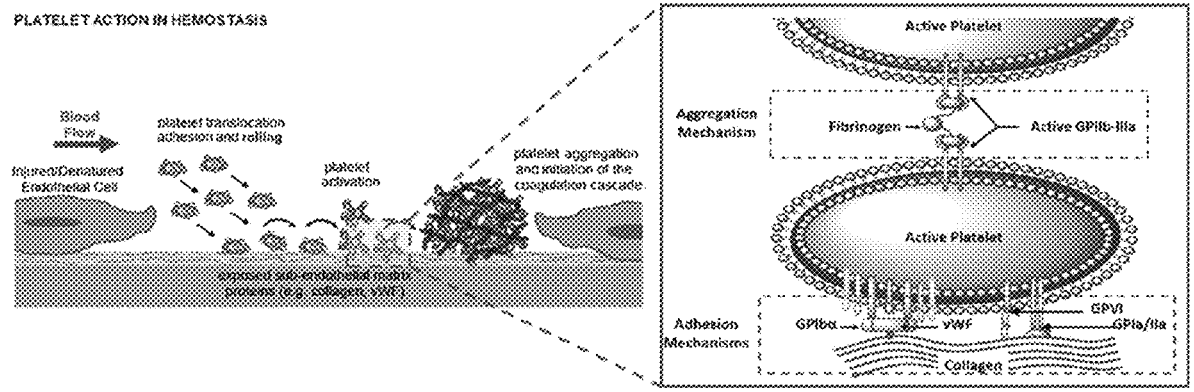
FIG. 1 is a schematic representation of molecular mechanisms of adhesion and aggregation of blood platelets in primary hemostasis. The adhesion is mediated by binding of the extracellular domain of GPIbα of the platelet surface receptor GPIb/IX/V to vWF and binding of the platelet surface receptors GPIa/IIa and GPVI to collagen.

As used herein, each of the following terms has the meaning associated with it in this section.

The articles "a" and "an" are used herein to refer to one or to more than one (i.e., to at least one) of the grammatical object of the article. By way of example, "an element" means one element or more than one element. Unless specifically stated or obvious from context, as used herein, the term "or" is understood to be inclusive.

The term "about" will be understood by persons of ordinary skill in the art and will vary to some extent on the context in which it is used. For example, the term "about" can be understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

"More than one" is understood as 2, 3, 4, 5, 6, 7, 8, 9, 10, 11, 12, 13, 14, 15, 16, 17, 18, 19, 20, 25, 30, 40, 50, 100, etc., or any value there between. "At least" a specific value, is understood to be that value and all values greater than that value.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

The term "agent" is used herein to denote a chemical compound, a mixture of chemical compounds, a biological macromolecule, or an extract made from biological materials.

The term "antibody," as used herein, refers to an immunoglobulin molecule, which is able to specifically bind to a specific epitope on an antigen. Antibodies can be intact immunoglobulin's derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

A "conservative substitution" is the substitution of an amino acid with another amino acid with similar physical and chemical properties. In contrast, a "nonconservative substitution" is the substitution of an amino acid with another amino acid with dissimilar physical and chemical properties.

The term "homology" is used synonymously with "identity."

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

The terms "diminishing," "reducing," or "preventing," "inhibiting," and variations of these terms, as used herein include any measurable decrease, including complete or substantially complete inhibition.

A "recombinant polypeptide" is one, which is produced upon expression of a recombinant polynucleotide.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

"Nanoparticle" is meant to include particles, spheres, capsules, and other structures having a length or diameter of about 10 nm to about 10 μm. For the purposes of this application, the terms "nanosphere", "nanoparticle", "nanocapsule", "microsphere", "microparticle", and "microcapsule" are used interchangeably.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "portion" of a polypeptide means at least about three sequential amino acid residues of the polypeptide. It is understood that a portion of a polypeptide may include every amino acid residue of the polypeptide.

The phrases "parenteral administration" and "administered parenterally" refer to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The terms "prevent", "preventing", "prevention", "prophylactic treatment" and the like are meant to refer to reducing the probability of developing a disorder or condition in a subject, who does not have, but is at risk of or susceptible to developing a disorder or condition. Prevention and the like do not mean preventing a subject from ever getting the specific disease or disorder. Prevention may require the administration of multiple doses. Prevention can include the prevention of a recurrence of a disease in a subject for whom all disease symptoms were eliminated, or prevention of recurrence in a relapsing-remitting disease.

This application relates to synthetic platelets and to their use in treating vascular injuries and conditions as well as to compositions and methods useful in the delivery of therapeutic agents to targeted sites in the vasculature of a subject. The synthetic platelets described herein integrate platelet-mimetic adhesion-, aggregation-, and therapeutic agent promoting functionalities on a single flexible nanoparticle.

It was found that the platelet-mimetic adhesion- and aggregation-promoting functionalities can be achieved by including on, conjugating to, or decorating a flexible nanoparticle with a plurality of site targeted peptides. It was further found that therapeutically relevant amounts of therapeutic agents can be encapsulated by and/or conjugated to the flexible nanoparticles described herein. Encapsulating and/or conjugating the therapeutic agents to the flexible nanoparticles can protect the agents in circulation, prevent non-specific distribution, prevent off-target side-effects and plasma-induced deactivation of the agents, and enhance target specific availability of the therapeutic agents by virtue of active anchorage of the nanoparticle to the targeted site via the plurality of site targeted peptides. Advantageously, destabilization of the flexible nanoparticles by site-relevant enzymes can trigger release of therapeutic agents at the targeted site.

In some embodiments, the synthetic platelets described herein having aggregation and therapeutic agent delivery-promoting functionalities can include a biocompatible, biodegradable, flexible nanoparticle core, a plurality of site targeted peptides bound to, conjugated to, and/or decorated on the outer surface defined by the flexible nanoparticle core, and a bioactive agent, diagnostic agent, and/or therapeutic agent encapsulated by and/or conjugated to the nanoparticle.

The plurality of site targeted peptides can include a plurality of single site-targeted peptides (homo multivalent peptides) or a plurality of site-targeted peptides capable of binding to two or more target sites (heteromultivalent peptides). The site targeted peptides can be spatially or topographically arranged on the flexible nanoparticle surface such that the site targeted peptides do not spatially mask each other and are able to adhere to a target site (e.g., a vascular surface, vascular disease site, and/or vascular injury site with exposed vWF and collagen) and thereby promote arrest and aggregation of active platelets as well as delivery of the therapeutic agent onto sites of nanoparticle adhesion.

The biocompatible, biodegradable, flexible nanoparticles can be made from any biocompatible, biodegradable material that can form a flexible nanoparticle to which the peptides described herein can be attached, conjugated, and/or decorated. In some embodiments, the biocompatible, biodegradable flexible nanoparticles can include a liposome, a hydrogel, micelle, and/or polymer, which can include and/or be surface modified or engineered with the site targeted peptides (e.g., a von Willebrand factor-binding peptide (VBP), a collagen-binding peptide (CBP), an active platelet GPIIb-IIIa-binding peptide (GBP), p-selectin binding peptides, and a brain injury site-targeting peptides).

The liposome or micelle can include a lipid and/or any naturally-occurring, synthetic or semi-synthetic (i.e., modified natural) moiety that is generally amphipathic (i.e., including a hydrophilic component and a hydrophobic component) and that can form an outer monolayer or bilayer membrane or shell of the nanoparticle. Examples of lipids can include fatty acids, neutral fats, phospholipids, oils, glycolipids, surfactants, aliphatic alcohols, waxes, terpenes and steroids. Semi-synthetic or modified natural lipids can include natural lipids that have been chemically modified in some fashion. The at least one lipid can be neutrally-charged, negatively-charged (i.e., anionic), or positively-charged (i.e., cationic). Examples of anionic lipids can include phosphatidic acid, phosphatidyl glycerol, and fatty acid esters thereof, amides of phosphatidyl ethanolamine, such as anandamides and methanandamides, phosphatidyl serine, phosphatidyl inositol and fatty acid esters thereof, cardiolipin, phosphatidyl ethylene glycol, acidic lysolipids, sulfolipids and sulfatides, free fatty acids, both saturated and unsaturated, and negatively-charged derivatives thereof. Examples of cationic lipids can include N-[1-(2,3-dioleoyloxy)propyl]-N,N,N-trimethyl-ammonium chloride and common natural lipids derivatized to contain one or more basic functional groups.

Other examples of lipids, any one or combination of which may be used to form the nanoparticle, can include: phosphocholines, such as 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine, dimyristoylphosphatidylcholine, dipentadecanoylphosphatidylcholine, dilauroylphosphatidylcholine, dipalmitoylphosphatidylcholine (DPPC), distearylphosphatidylcholine (DSPC), and diarachidonylphosphatidylcholine (DAPC); phosphatidylethanolamines, such as dioleoylphosphatidylethanolamine, dipalmitoylphosphatidylethanolamine (DPPE), and distearoylphosphatidylethanolamine (DSPE); phosphatidylserine; phosphatidylglycerols, including distearoylphosphatidylglycerol (DSPG); phosphatidylinositol; sphingolipids, such as sphingomyelin; glycolipids, such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG); lipids bearing sulfonated mono-, di-, oligo- or polysaccharides; cholesterol, cholesterol sulfate, and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes, such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN (commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3-yloxy)-1-thio-D-galactopyranoside; digalactosyldiglyceride; 6-(5-cholesten-3-yloxy)hexyl-6-amino-6-deoxy-1-thio-D-galactopyranoside; 6-(5-cholesten-3-yloxy)hexyl-6-amino-6-deoxyl-1-thio-a-D-mannopyranoside; 12-(((7'-diethylaminocoumarin-3-yl) carbonyl)methylamino)octadecanoic acid; N-[12-(((7'-diethylaminocoumarin-3-yl)carbonyl)methylamino) octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine; and/or any combinations thereof.

In some embodiments, the biocompatible flexible liposome nanoparticle can include a lipid that can act as a substrate, which can be cleaved and/or destabilized by a site relevant enzyme (i.e., an enzyme present at a targeted site) to provide site-relevant delivery of a therapeutic agent encapsulated and/or conjugated to the nanoparticle at the targeted site. The enzyme cleavable or destabilizable lipid can include, for example, a glycerophospholid with an sn-2 ester bond, which can be cleaved by a phospholipase, such as secreted phospholipase A2 (sPLA2), to destabilize the lipid membrane of the nanoparticle to release a therapeutic agent. An example of glycerophospholipid with an sn-2 ester bond is 1,2-Distearoyl-sn-glycero-3-phosphocholine (DSPC).

In some embodiments, the biocompatible flexible liposome nanoparticle can include a membrane that is formed using reverse phase evaporation extrusion techniques from at least about 10%, about 20%, about 30%, about 40%, about 50%, or more of DSPC and one or more other lipids, such as DSPE or DHPE that is conjugated to a targeting peptide and In other embodiments, a biocompatible flexible liposome nanoparticle can include a pro-coagulant liposome. For example, a pro-coagulant liposome can have a high surface presentation of anionic phosphatidylserine (PS) lipid. The PS-rich surface of the liposome can facilitate intrinsic coagulation mechanisms in the subject in applications where such coagulation is advantageous, such as for slowing bleeding in the treatment of vascular injuries. In some embodiments, the biocompatible flexible liposome nanoparticle can include a non-coagulant liposome. For example, the bulk of the lipid in the biocompatible flexible liposome nanoparticle can include a non-coagulant lipid, such as DSPC.

Other examples of biocompatible, biodegradable polymers that can be used to form the nanoparticles are poly (lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly (dioxanone)s, poly(alkylene alkylate)s, copolymers of polyethylene glycol and poly(lactide)s or poly(lactide-co-glycolide)s, biodegradable polyurethanes, and blends and/or copolymers thereof.

Other examples of materials that may be used to form the nanoparticles can include chitosan, poly(ethylene oxide), poly(lactic acid), poly(acrylic acid), poly(vinyl alcohol), poly(urethane), poly(N-isopropyl acrylamide), poly(vinyl pyrrolidone) (PVP), poly(methacrylic acid), poly(p-styrene carboxylic acid), poly(p-styrenesulfonic acid), poly(vinylsulfonicacid), poly(ethyleneimine), poly(vinylamine), poly(anhydride), poly(L-lysine), poly(L-glutamic acid), poly(gamma-glutamic acid), poly(carprolactone), polylactide, poly(ethylene), poly(propylene), poly(glycolide), poly(lactide-co-glycolide), poly(amide), poly(hydroxylacid), poly(sulfone), poly(amine), poly(saccharide), poly(HEMA), poly(anhydride), gelatin, glycosaminoglycans (GAG), poly(hyaluronic acid), poly(sodium alginate), alginate, albumin, hyaluronan, agarose, polyhydroxybutyrate (PHB), copolymers thereof, and blends thereof.

The flexible nanoparticles can have a maximum length or diameter of about 100 nm to about 10 m and a substantially spherical, discoidal, and/or ellipsoidal shape. The physical size and shape as well as mechanical properties of the nanoparticles can be engineered to mimic those of natural platelets that are important in hemostasis. In some embodiments, the flexible nanoparticles can have an about 2 to about 5 m diameter discoidal shape and an about 10 to about 50 kPa mechanical elastic modulus that mimics the size, shape, and elastic modulus of platelets and facilitates upon administration to the vasculature of a subject their margination to the vascular wall and their bio-interactions.

In an embodiment, oblate ellipsoid nanoparticles having a diameter of about 2 to about 5 m and a mechanical modulus of about 10 to about 50 kPa can be prepared by initially forming a polymer template. The polymer template can then be used to build a protein/polymer shell using a cross-linked layer-by-layer assembly. The polymer template can subsequently be removed using solvents to leave behind soft, flexible, proteinaceous discoid particles having a diameter about 2 to about 5 m and a mechanical elastic modulus of about 10 to about 50 kPa. The particles can then be surface-modified with the site targeted peptides (e.g., VBPs, CBPs, and GBPs) at a surface density effective to promote maximum particle adhesion to targeted sites (e.g., vWF and collagen exposed surfaces) at low-to-high sheer stresses and promote aggregation of active platelets even at low (less about 50,000 µl) platelet concentrations.

In some embodiments, the synthetic platelets described herein can include a biocompatible, biodegradable, flexible nanoparticle core and a plurality of at least three different peptides, e.g., VBPs, CBPs, and GBPs, bound to, conjugated to, and/or decorated on the a surface defined by the flexible nanoparticle core. Such a synthetic platelet can adhere to a vascular surface, vascular disease site, and/or vascular injury site with exposed von Willebrand factor and collagen, thereby promoting arrest and aggregation of active platelets and the delivery of the therapeutic agents encapsulated by and/or conjugated to the nanoparticle onto sites of the synthetic platelet adhesion.

In some embodiments, the VBP peptide for vWF binding can include a recombinant GPIbα fragment (rGPIbα) containing the vWF binding sites (residues 1 to 302) or a short chain vWF-binding peptide. The GPIbα fragment can be expressed in CHO cells and isolated, adapting methods described. The short vWF-binding peptide can include the amino acid sequence of TRYLRIHPQSWVHQI (SEQ ID NO: 1). A peptide having an amino acid sequence of SEQ ID NO: 1 can be synthesized using fluorenylmethyloxycarbonyl chloride (FMoc)-based solid phase chemistry on Knorr resin, and characterized using mass spectroscopy. Each vWF molecule has only one binding region for this peptide, and hence vascular injury sites presenting multiple vWF binding sites for multiple copies of this peptide decorated on the nanoparticle surface, provide a mechanism for enhanced adhesion of the nanoparticles with increasing shear.

In some embodiments, the CBP can include a peptide that comprises a short seven-repeat of the tripeptide GPO (i.e., [GPO]$_7$, SEQ ID NO: 2) with a helicogenic affinity to fibrillar collagen. The GPO trimer is based on amino acid repeats found in the native collagen structure. It has been reported that the activation of platelets usually caused by interaction with collagen through GPVI and GPIa/IIa, can also potentially occur when platelets interact with collagen-derived peptides. This can be a potential problem regarding decorating synthetic particle surfaces with collagen-derived peptides for binding of collagen, because in vivo the constructs can potentially interact with quiescent blood platelets and systemically activate them, posing thromboembolic risks. However, interaction of platelet receptors with collagen and the subsequent platelet activation mechanisms are dependent upon receptor clustering induced by multimeric long chain triple-helical fibrillar collagen and not by short collagen-mimetic peptide repeats. In fact, it has been shown that GPO-trimer repeats as high as a 30-mer (10 repeats) only partially interact with platelet GPIa/IIa and GPVI integrins and are incapable of activating platelets; yet they can effectively bind to fibrillar collagen via helicogenic interaction. Hence, this small CBP can promote adhesion to fibrillar collagen, but cannot activate quiescent platelets due to absence of long triple-helical conformation. The CBP like the VBP can also be synthesized using FMoc-based solid phase chemistry on Knorr resin, and characterized using mass spectroscopy.

In some embodiments, the GBP can include an RGD amino acid sequence motif that promotes active platelet aggregation. The RGD motif containing GBP may contain a single repeat of the RGD motif or may contain multiple repeats of the RGD motif, such as, for example, 2, or 5, or 10 or more repeats of the RGD motif. One of skill in the art will understand that conservative substitutions of particular amino acid residues of the RGD motif containing GBPs may be used so long as the RGD motif containing GBP retains the ability to bind comparably as the native RGD motif. One of skill in the art will also understand that conservative substitutions of particular amino acid residues flanking the RGD motif so long as the RGD motif containing GBP retains the ability to bind comparably as the native RGD motif.

In some embodiments, the GBP can include a cyclic RGD (cRGD) peptide having the amino acid sequence of cyclo-CNPRGDY(OEt)RC (SEQ ID NO: 3). A cyclic peptide having SEQ ID NO: 3 can have high selectivity and affinity to GPIIb-IIIa on activated platelets but do not bind or activate quiescent platelets nor interact with other RGD-binding integrins.

In other embodiments, the GBP can include a peptide having the amino acid sequence of GSSSGRGDSPA (SEQ ID NO: 4). The GBP like the VBP and CBP can be synthesized using FMoc-based solid phase chemistry on Knorr resin, and characterized using mass spectroscopy.

In some embodiments, the synthetic platelets described herein can include a biocompatible, biodegradable, flexible nanoparticle core and a plurality of GBPs and active platelet p-selectin binding peptides bound to, conjugated to, and/or decorated on the a surface defined by the flexible nanoparticle core. In some embodiments, the synthetic platelet can adhere to an active platelet rich thrombus site, thereby promoting the delivery of the therapeutic agents (e.g., fibrinolytic agents) encapsulated by the nanoparticle onto active platelet rich thrombus sites.

In some embodiments, the active platelet p-selectin binding peptide can include the amino acid sequence of DAEWVDVS (SEQ ID NO: 5). The p-selectin binding peptide can be synthesized using FMoc-based solid phase chemistry on Knorr resin, and characterized using mass spectroscopy.

In some embodiments, the synthetic platelets described herein can include a biocompatible, biodegradable, flexible nanoparticle core and a plurality of brain injury site-targeting peptides bound to, conjugated to, and/or decorated on the a surface defined by the flexible nanoparticle core. In some embodiments, the synthetic platelet can adhere to a brain injury site, thereby promoting the delivery of the therapeutic agent (e.g., a neuroprotective agent) encapsulated by the nanoparticle onto sites of the brain injury.

In some embodiments, the brain injury site-binding peptide can include a peptide sequence having specific binding capability to extracellular matrix domins (or perineuronal nets or (PNNs)) rich in chondroitin sulfate proteoglycans (CSPGs) that are upregulated at traumatic brain injury sites (TBI). In some embodiments, the brain injury site-binding peptide can include the amino acid sequence of CAQK (SEQ ID NO: 6). The brain injury site-binding peptide can be synthesized using FMoc-based solid phase chemistry on Knorr resin, and characterized using mass spectroscopy.

Advantageously, the site targeted peptides can each include about 5 to about 30 amino acids. By limiting the size of the peptides to about 5 to about 30 amino acids, the site targeted peptides can be spatially or topographically arranged on the flexible nanoparticle surface such that the site targeted peptides do not spatially mask each other and are able to adhere to a targeted site (e.g., vascular surface, vascular disease site, and/or vascular injury site with exposed vWF and collagen) and promote arrest and aggregation of active platelets and the delivery of the therapeutic agents encapsulated by the nanoparticle onto sites of the synthetic platelet adhesion The site-targeted peptides (e.g., VBPs, CBPs, GBPs, p-selectin binding peptides, and brain injury site-targeted peptides) can be conjugated to the nanoparticle surface by reacting the peptides through their N-termini to the carboxyl termini of a heterobifunctional PEG, such as maleimide-PEG-COOH. The PEG-peptide conjugates or PEGylated peptides can then be conjugated to the nanoparticle using known conjugation techniques.

The PEG molecules can have a variety of lengths and molecular weights, including, for example, PEG 200, PEG 1000, PEG 1500, PEG 4600, PEG 10,000, or combinations thereof. In other embodiments, the site-targeted peptides can be conjugated to the nanoparticle surface with PEG acrylate, or PEG diacrylate, molecules of a variety of molecular weights.

In one example, the site targeted peptides can be reacted with maleimide-PEG-COOH to form Mal-PEG-peptide conjugates. SA/PAH nanoparticles with albumin as the outermost layer can then be treated with dithiothreitol (DTT) to introduce a high density of sulfhydryl (—SH) groups on the surface. The Mal-PEG-peptides can then be incubated with the DTT-treated nanoparticles, such that the MAL termini can react with the free —SH groups to form particles decorated with various peptides presented on the particle surface via PEG linkers.

In another example, the site targeted peptides can be conjugated to a poly(ethylene glycol) terminated distearyl phosphatidyl ethanolamine (i.e. DSPE-PEG) lipid molecule via amide, thioether or 'click' chemistry to form DSPE-PEG-peptide conjugates. Resultant conjugates can then be self-assembled with distearyl phosphatidyl choline (DSPC) and cholesterol into unilamellar liposomal nanoparticle vesicles such that the outer leaflet is decorated with homo- or hetero-multivalent peptide conjugate motifs.

The ratio of VPBs to CPBs provided on the nanoparticle surface can be about 70:30 to about 30:70 and be adjusted accordingly to maximize adhesion under low-to-high shear conditions. In some embodiments, the ratio of VPB:CPB:GBP can be about 1:1:2 to 1:2:1 to 2:1:1. In some embodiments, the ratio of GBP: p-selectin binding proteins can be about 1:1. It will be appreciated, that other ratios can be used to enhance the nanoparticle adherence and activated platelet aggregation as well as therapeutic agent delivery.

The site-relevant enzymes can include any endogenous enzyme found at or near a targeted site in a subject capable of destabilizing nanoparticles described herein allowing for release of a therapeutic agent encapsulated therein. For example, the site-relevant enzyme can include a bleeding site-relevant enzyme, such as phospholipases or thrombin. In some embodiments, the site-relevant enzyme is a thrombus-relevant enzyme, such as phospholipase-$A_2$ ($PLA_2$). By way of example, a nanoparticle described herein may be composed, at least in part, by the lipid DSPC. DSPC is a known substrate for the site-relevant enzyme, secreted phospholipase $A_2$ (sPLA2) produced from activated platelets and inflammatory cells in athero-thrombotic milieu, which can cleave the sn-2 ester bonds in glycerophospholipids, thereby destabilizing nanoparticles and release of an encapsulated and/or conjugated to therapeutic agent.

A bioactive agent, diagnostic agent, and/or therapeutic agent can be encapsulated in and/or conjugated to the synthetic platelet so that the synthetic platelet acts as a delivery vehicle wherein the synthetic platelet promotes delivery of the agent to sites of the synthetic platelet adhesion and wherein the agent is release at the site targeted via a site-relevant enxyme. Selection of a bioactive agent, diagnostic agent, and/or therapeutic agent to be encapsulated within and/or conjugated to the synthetic platelet is dependent upon the use of the synthetic platelet and/or the condition being treated and the site and route of administration.

Bioactive agents encapsulated by and/or conjugated to the synthetic platelet can include any substance capable of exerting a biological effect in vitro and/or in vivo. Examples of bioactive agents can include, but are not limited to, biologically active ligands, small molecules, DNA fragments, DNA plasmids, interfering RNA molecules, such as siRNAs, oligonucleotides, and DNA encoding for shRNA. Diagnostic agents can include any substance that may be used for imaging a region of interest (ROI) in a subject and/or diagnosing the presence or absence of a disease or diseased tissue in a subject. Therapeutic agents can refer to any therapeutic or prophylactic agent used in the treatment (including the prevention, diagnosis, alleviation, or cure) of a malady, affliction, condition, disease or injury in a subject. It will be appreciated that the nanoparticle membrane can additionally or optionally include proteins, carbohydrates, polymers, surfactants, and/or other membrane stabilizing materials, any one or combination of which may be natural, synthetic, or semisynthetic.

Therapeutic agents encapsulated by and/or conjugated to a nanoparticle described herein can include, but are not limited to, anti-fibrinolytic agents, fibrin crosslinking agents, coagulation-promoting agents and factors, wound healing agents, anti-infective agents, anti-viral agents, anti-fungal agents, amoebicidal agents, trichomonocidal agents, immunomodulatory agents, anti-inflammatory agents, anti-fibrinolytic agents, anti-oxidants, neuroprotective agents, anticholinergic agents, anti-neoplastic agents, anti-hypertensive agents, analgesic agents, and combinations thereof. Preferably the therapeutic agent is substantially evenly dispersed throughout the core.

In some embodiments, the therapeutic agent is an anti-fibrinolytic agent. Any suitable anti-fibrinolytic agent can be used. Anti-fibrinolytic agents can strengthen clotting in a subject. Anti-fibrinolytic agents can include thrombolytic antagonists (e.g., amiocaproic acid (amicar) and tranexamic acid (amstat or TXA)), antithrombotics (e.g., anagrelide, argatroban, cilstazol, daltroban, defibrotide, enoxaparin, fraxiparine, indobufen, lamoparan, ozagrel, picotamide, plafibride, tedelparin, ticlopidine and triflusal), and anticoagulant antagonists (eg., protamine and vitamine Kl). In some embodiments, the anti-fibrinolytic agent is tranexamic acid. Coagulation factors can include recombinant coagulation factors, such as, but not limited to FXIIIa, FVIIa, FVIII and the recombinant FVIIa product (NovoSeven).

In other embodiments, the therapeutic agent is a fibrinolytic agent. Any suitable fibrinolytic agent can be used. Fibrinolytic agents are compounds that dissolve blood clots by activating plasminogen to plasmin. Plasmin formation and/or activation leads to the degradation of fibrin to accomplish fibrinolysis, and thereby clot dissolution. For example, the fibrinolytic agent can be tissue plasminogen activator (tPA), streptokinase (SK), or urokinase (UK). In certain embodiments, the fibrinolytic agent is streptokinase (SK). In some embodiments, the fibrinolytic agent is a tissue plasminogen activator. Examples of tissue plasminogen activators include Alteplase (a recombinant form of tPA), Retaplase (a smaller derivative of recombinant tPA), and Tenecteplase, which has a longer half-life and greater binding affinity for fibrin. Additional fibrinolytic agents can include, but are not limited to, anticoagulants (acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin), antiplatelet agents (aspirin, a dextran, dipyridamole (persantin), heparin, sulfinpyranone (anturane) and ticlopidine (ticlid)).

In some embodiments the therapeutic agent is an anti-infective agent. Anti-infective agents can facilitate wound bed protection and wound healing (i.e. increased epithelialization). An anti-infective agent can include an antibiotic agent. Examples of antibiotic include, but are not limited to, penicillins such as penicillin and amoxicillin, cephalosporins such as cephalexin (Keflex), macrolides such as erythromycin (E-Mycin), clarithromycin (Biaxin), and azithromycin (Zithromax), fluoroquinolones such as ciprofloxacin (Cipro), levofloxacin (Levaquin), and ofloxacin (Floxin), sulfonamides such as co-trimoxazole (Bactrim) and trimethoprim (Proloprim), tetracyclines such as tetracycline (Sumycin, Panmycin) and doxycycline (Vibramycin), and aminoglycosides such as gentamicin (Garamycin) and tobramycin (Tobrex).

In an exemplary embodiment, the anti-infective agent is gentamicin. A synthetic platelet including gentamicin can be administered to provide wound protection and decrease inflammation by limiting bacterial growth and migration of inflammatory markers and improving re-epithelialization, improving wound healing and decrease scar formation.

In some embodiments, the therapeutic agent is an anti-inflammatory agent. Examples of anti-inflammatory agents can include, but are not limited to, adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal antiinflammatory drugs (e.g., aspirin, ibuprofen, diclofenac, and COX-2 inhibitors), and leukotreine antagonists (e.g., montelukast, methyl xanthines, zafirlukast, and zileuton).

In some embodiments, the therapeutic agent is a neuroprotective agent. A neuroprotective agent can include a brain-derived neurotrophic factor (BDNF), a glial cell line-derived neurotrophic factor (GDNF), a nerve growth factor (NGF), and/or a ciliary neurotrophic factor (CNTF). In some embodiments, the neuroprotective agent includes the Cerebrolysin, which is a peptidergic cocktail including brain-derived neurotrophic factor (BDNF), glial cell line-derived neurotrophic factor (GDNF), nerve growth factor (NGF), and ciliary neurotrophic factor (CNTF).

Additional therapeutic agents, which may be included in a synthetic platelet, can include, but are not limited to, beta blockers, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin type 2 antagonists and cytokine blockers/inhibitors, and HDAC inhibitors.

In some embodiments of the synthetic platelets provided herein, the weight/weight (w/w) percent of the therapeutic agent encapsulated in the synthetic platelet is about 5%. In some embodiments, the w/w percent of the fibrinolytic agent in and/or conjugated to the encapsulated active agent nanoparticles is about 2-10%.

In some embodiments, the synthetic platelets including a therapeutic agent described herein can be provided in a pharmaceutical composition. Such a pharmaceutical composition may consist of a synthetic platelet encapsulating one or more therapeutic agents alone, in a form suitable for administration to a subject, or the pharmaceutical composition may comprise a synthetic platelet encapsulating one or more therapeutic agents and one or more pharmaceutically acceptable carriers, one or more additional ingredients, one or more pharmaceutically acceptable therapeutic agents, bioactive agents, diagnostic agents, or some combination of these that is not encapsulated by the synthetic platelet. The therapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the therapeutic agent may be combined and which, following the combination, can be used to administer the therapeutic agent to a subject.

As used herein, the term "physiologically acceptable" ester or salt means an ester or salt form of the therapeutic agent which is compatible with any other ingredients of the pharmaceutical composition, which is not deleterious to the subject to which the composition is to be administered.

The compositions comprising a synthetic platelet may be formulated and administered to a subject, preferably a human subject, to facilitate the delivery of a therapeutic agent to a targeted site in the subject. Therefore, the application further relates to methods of treating a subject in need thereof through the administration of the synthetic platelets encapsulating and/or conjugated to therapeutic agents described herein. For example, a subject may be in need of therapeutic treatment for a vascular injury, traumatic brain injury, reducing or slowing blood loss, and/or treatment for vascular occlusive condition.

The methods of treatment using the synthetic platelets described herein include administering a therapeutically effective amount of a synthetic platelet to a subject in need thereof. Determination of a therapeutically effective amount is within the capability of those skilled in the art. The exact formulation, route of administration and dosage can be chosen by the individual physician in view of the patient's condition. In some embodiments, synthetic platelets described herein including a therapeutic agent (e.g., a fibrinolytic agent or an anti-fibrinolytic agent) are therapeutically effective in the subject without inhibiting hemostasis.

In some embodiments, synthetic platelets encapsulating a therapeutic agent described herein can be administered to a subject for the treatment of a vascular injury in the subject, wherein the synthetic platelet can adhere to a vascular surface, vascular disease site, and/or vascular injury site with exposed von Willebrand factor and collagen, thereby promoting arrest and aggregation of active platelets and the delivery of the therapeutic agent encapsulated by the synthetic platelet onto sites of the synthetic platelet adhesion. In some embodiments, the synthetic platelets encapsulating a therapeutic agent described herein can enhance primary hemostasis (platelet-mediated clot formation), and also amplify secondary hemostasis (fibrin amplification and clot stabilization) and/or prevent clot lysis and dissolution (i.e. anti-fibrinolytic benefit).

It should be understood, that the methods of treatment by the delivery of a synthetic platelet include the treatment of subjects that have, or have been diagnosed with, a vascular injury or occlusive condition, as well as prophylactic treatment uses in subjects not yet having, or having been diagnosed with a vascular injury or occlusive condition. For example, the methods of treatment by the delivery of a synthetic platelet can include the treatment of subjects that are already bleeding, as well as prophylactic treatment uses in subjects not yet bleeding. In a preferred embodiment the subject is an animal. In a more preferred embodiment the subject is a human.

In some embodiments, the therapeutic agent encapsulated by and/or conjugated to a synthetic platelet described herein for use in a method of treating a vascular injury can include, but is not limited to, an anti-fibrinolytic agent, a fibrin crosslinking agent, a coagulation-promoting agent, a wound healing agent, an anti-infective agent, an immunomodulatory agent, an anti-inflammatory agent and combinations thereof.

Another aspect of the application relates to administration, such as for example intravenous administration, of the synthetic platelets described herein to a subject with a vascular injury in order to diminish the bleeding time, blood loss amount, blood loss rate, and/or increase hemostasis and survival in the subject. It is a further aspect of the application that the synthetic platelets provide a nanostructure that binds with a vascular injury site as well as activated platelets and enhances their rate of aggregation to aid in stopping bleeding and particularly hemorrhage from traumatic injury, medical bleeding, and non-compressible hemorrhage. In addition the synthetic platelet can deliver a therapeutic agent to the targeted vascular injury site of the subject to aid in treating the vascular injury.

In some embodiments, the subject can have or be at increased risk of thrombocytopenia. The thrombocytopenia can be caused by or result from dehydration, leukemia, myelodysplastic syndrome, aplastic anemia, liver failure, sepsis, leptospirosis, congenital amegakaryocytic thrombocytopenia, thrombocytopenia absent radius syndrome, fanconi anemia, Bernard-Soulier syndrome, May-Hegglin anomaly, grey platelet syndrome, Alport syndrome, Wiskott-Aldrich syndrome, idiopathic thrombocytopenic purpura, thrombotic thrombocytopenia purpura, hemolytic-uremic syndrome, disseminated intravascular coagulation, paroxysmal nocturnal hemoglobinuria, antiphospholipid syndrome, systemic lupus erythematosus, post-transfusion purpura, neonatal alloimmune thrombocytopenia, hypersplenism, dengue fever, Gaucher's disease, zika virus, medication-induced thrombocytopenia, niacin toxicity, Lyme disease, and thrombocytapheresis.

In other embodiments, the synthetic platelets described herein can be used to treat a bleeding disorder. In one embodiment, the bleeding disorder is hemophilia. In a further embodiment, the hemophilia is hemophilia A. In yet another embodiment the hemophilia is hemophilia B. In one embodiment, the hemophilia is hemophilia A. In another embodiment, the hemophilia is acquired hemophilia A with inhibitory auto antibodies to FVIII. In one embodiment, the hemophilia is congenital hemophilia B with inhibitors. In another embodiment, the hemophilia is acquired hemophilia B with inhibitory auto antibodies to FIX.

In other embodiments, the bleeding disorder is a non-hemophilia bleeding disorder. In one embodiment, the bleeding disorder is blood loss from trauma. In another embodiment, the bleeding disorder is FVII deficiency. In one embodiment, the bleeding disorder is FV deficiency. In another embodiment, the bleeding disorder is FX deficiency. In one embodiment, the bleeding disorder is FXI deficiency. In one embodiment, the bleeding disorder is FXIII deficiency. In one embodiment, the bleeding disorder is fibrinogen deficiency. In one embodiment, the bleeding disorder is prothrombin deficiency. In another embodiment, the bleeding disorder is dilutional coagulopathy. In a further embodiment, the bleeding disorder is thrombocytopenia. In yet another embodiment, the bleeding disorder is blood loss from high-risk surgeries. In another embodiment, the bleeding disorder is intracerebral hemorrhage. In one embodiment, the bleeding disorder is von Willebrand disease. In a further embodiment, the bleeding disorder is von Willebrand disease with inhibitors to von Willebrand factor.

In other embodiments, the bleeding disorder is a congenital platelet function defect, including, but not limited to, platelet storage pool disorder, Glanzmann's thrombasthenia, or Bernard-Soulier syndrome. In one embodiment, the bleeding disorder is an acquired platelet function defect. In one embodiment, the bleeding disorder is a congenital deficiency of Factor II, Factor V, Factor VII, Factor X, or Factor XI. In one embodiment, the bleeding disorder is neonatal and pediatric coagulopathies. In one embodiment, the bleeding disorder is a platelet function disorder. In another embodiment, the bleeding disorder is heparin-induced thrombocytopenia. In one embodiment, the bleeding disorder is disseminated intravascular coagulation.

In other embodiments, the non-hemophilia bleeding disorder is blood loss from trauma. In another embodiment, the non-hemophilia bleeding disorder is FVII deficiency. In one embodiment, the non-hemophilia bleeding disorder is FV deficiency. In another embodiment, the non-hemophilia bleeding disorder is FX deficiency. In one embodiment, the non-hemophilia bleeding disorder is FXI deficiency. In one embodiment, the non-hemophilia bleeding disorder is FXIII deficiency. In one embodiment, the non-hemophilia bleeding disorder is fibrinogen deficiency. In one embodiment, the non-hemophilia bleeding disorder is prothrombin deficiency. In another embodiment, the non-hemophilia bleeding disorder is dilutional coagulopathy. In a further embodiment, the non-hemophilia bleeding disorder is thrombocytopenia. In yet another embodiment, the non-hemophilia bleeding disorder is blood loss from high-risk surgeries. In another embodiment, the non-hemophilia bleeding disorder is intracerebral hemorrhage. In one embodiment, the non-hemophilia bleeding disorder is von Willebrand disease. In a further embodiment, the non-hemophilia bleeding disorder is von Willebrand disease with inhibitors to von Willebrand factor.

In one embodiment, the non-hemophilia bleeding disorder is a congenital platelet function defect, including, but not limited to, platelet storage pool disorder, Glanzmann's thrombasthenia, or Bernard-Soulier syndrome. In one embodiment, the non-hemophilia bleeding disorder is an acquired platelet function defect. In one embodiment, the non-hemophilia bleeding disorder is a congenital deficiency of Factor II, Factor V, Factor VII, Factor X, or Factor XI. In one embodiment, the non-hemophilia bleeding disorder is neonatal and pediatric coagulopathies. In one embodiment, the non-hemophilia bleeding disorder is a platelet function disorder. In another embodiment, the non-hemophilia bleeding disorder is heparin-induced thrombocytopenia. In one embodiment, the non-hemophilia bleeding disorder is disseminated intravascular coagulation. In other embodiments, the non-hemophilia bleeding disorder is any disorder known to one of skill in the art.

Another aspect of the invention relates to a method of treating a vascular occlusive condition in a subject. The method includes administering to the subject a synthetic platelet comprising a biocompatible flexible nanoparticle and a therapeutic agent, wherein the therapeutic agent is encapsulated by and/or conjugated to the nanoparticle.

A synthetic platelet administered to a subject for the treatment of a vascular occlusive condition includes a plurality of active platelet GPIIb-IIIa-binding peptides (GBPs) and active platelet p-selectin binding peptides conjugated to the surface. The synthetic platelet adheres to an active platelet rich thrombus site by virtue of active anchorage of the synthetic platelet to the site and promotes delivery of the therapeutic agent onto sites of the active platelet rich thrombus.

In some embodiments, the subject has been characterized as being in need of having a blood clot dissolved. A blood clot (e.g., thrombus) is the product of hemostasis resulting from platelet aggregation within a fibrin clot, and while useful in cases of injury, it is pathological in instances of thrombosis. Blood clots can occur in a variety of medical conditions, many of which are life threatening. For example, blood clots can occur in deep vein thrombosis, where they can embolize to flow through the heart and into the lungs where they form a pulmonary embolism. Blood clots can also form an arterial thrombus, causing a heart attack, stroke, or peripheral vascular disease, depending on whether the thrombus forms in the coronary arteries, arteries of the brain, or arteries of the leg, respectively. Blood clots can also form in abdominal aortic aneurysms.

In some embodiments, synthetic platelets including a therapeutic agent can be administered to a subject to inhibit thrombosis formation in a subject prone to or suffering from cardiovascular disease. The cardiovascular disease can include, for example, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular graft surgery, stent placements and insertion of endovascular devices and prostheses.

In some embodiments, the compositions or pharmaceutical compositions including a synthetic platelets a therapeutic agent described herein can be used in methods of treating disease states in mammals which have disorders related to coagulation, such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries and/or vasculature. Further, these compositions are useful for the treatment or prophylaxis of those diseases which involve a number of thrombotic or thromboembolic events.

The term, "thrombotic or thromboembolic event," includes any disorder that involves a blockage or partial blockage of an artery or vein with a thrombosis or thromboembolism, all of which can be treated by the compositions described herein. A "thrombosis" is the formation of a clot (or thrombus) inside a blood vessel that can obstruct the flow of blood through the circulatory system. A "thromboembolism" involves formation in a blood vessel of a clot (thrombus) that breaks loose and is carried by the blood stream to lodge in another vessel area. The clot may lodge in a vessel in the lungs (pulmonary embolism), brain (stroke), gastrointestinal tract, kidneys, or leg. Thromboembolism is an important cause of morbidity (disease) and mortality (death), especially in adults.

A thrombotic or thromboembolic event occurs when a clot forms and lodges within a blood vessel. The clot may fully or partially block the blood vessel causing a thrombotic disorder such as a heart attack or stroke. Examples of thrombotic or thromboembolic events include thrombotic disorders such as acute myocardial infarction, unstable angina, ischemic stroke, acute coronary syndrome, pulmonary embolism, transient ischemic attack, thrombosis (e.g., deep vein thrombosis, thrombotic occlusion and re-occlusion and peripheral vascular thrombosis) and thromboembolism. A thrombotic or thromboembolic event also includes first or subsequent thrombotic stroke, acute myocardial infarction, which occurs subsequent to a coronary intervention procedure, or thrombolytic therapy.

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

In some embodiments, the compositions described herein are useful in treating thromboembolic stroke, ischemic or hemorrhagic stroke, systemic embolism, stroke prevention in atrial fibrillation (SPAF), non-valvular atrial fibrillation, venous thromboembolism (VTE), prevention of VTE in knee or hip surgery, prevention of VTE in acute medically ill patients, and secondary prevention in acute coronary syndrome (ACS). In some embodiments, the compositions are for treatment of embolic stroke, thrombotic stroke, venous thrombosis, deep venous thrombosis, acute coronary syndrome, or myocardial infarction.

In some embodiments, the compositions are for prevention of stroke in atrial fibrillation patients; prevention of thrombosis in medically ill patients; prevention and treatment of deep vein thrombosis; prevention of arterial thrombosis in acute coronary syndrome patients; and/or secondary prevention of myocardial infarction, stroke or other thrombotic events in patients who have had a prior event.

In some embodiments, the patient has atrial fibrillation. In some embodiments, the patient is a patient with non-valvular atrial fibrillation. In some embodiments, the patient has atrial flutter.

In one embodiment, a synthetic platelet composition described herein can be administered about 6 hours to 24 hours after thrombolysis has occurred, about 12 hours to 24 hours after thrombolysis has occurred, or about 20 hours to 24 hours after thrombolysis has occurred. In another aspect, the compound is administered multiple times. The number of doses administered will depend on the type and severity of the thrombotic or thromboembolic condition to be treated. This determination can be made by one skilled in the art and is within the scope of the invention.

In one embodiment, the compound may be administered on an ongoing basis to treat or prevent angina, myocardial infarction, stroke, pulmonary embolism, transient ischemic attack, coronary ischemic syndrome, Syndrome X, heart failure, diabetes, disorders in which a narrowing of at least one coronary artery occurs, thrombosis including catheter thrombosis, deep vein thrombosis, arterial vessel thrombosis, and peripheral vascular thrombosis, or thrombotic occlusion and re-occlusion, including re-occlusion subsequent to a coronary intervention procedure, or in connection with heart surgery or vascular surgery.

In some embodiments, the therapeutic agent encapsulated by a synthetic platelet described herein for use in a method of treating a vascular occlusive condition can include, but is not limited to, a fibrinolytic agent, a plasminogen activating agent, an anticoagulant agent, an anti-inflammatory agent, an anti-oxidant, and combinations thereof. In some embodiments, the therapeutic agent encapsulated by a synthetic platelet described herein for use in a method of treating a vascular occlusive condition is a fibrinolytic agent. In certain embodiments, the fibrinolytic agent is streptokinase (SK).

Another aspect of the invention relates to a method of treating a traumatic brain injury (TBI) in a subject. The method includes administering to the subject a synthetic platelet comprising a biocompatible flexible nanoparticle and a therapeutic agent, wherein the therapeutic agent is encapsulated by and/or conjugated to the nanoparticle.

A synthetic platelet administered to a subject for the treatment of a TBI includes a plurality of brain injury site-targeting peptides conjugated to the surface. The synthetic platelet adheres to a brain injury site by virtue of active anchorage of the synthetic platelet to the site and promotes delivery of the therapeutic agent onto sites of the brain injury. In an exemplary embodiment, the brain injury site-targeting peptides have the amino acid sequence CAQK (SEQ ID NO: 6).

In some embodiments, the synthetic platelets including the therapeutic agents are administered at an amount effective to reduce intracerebral microvascular thrombosis and/or decrease cerebral injury size.

The therapeutic agent described herein for use in a method of treating a TBI can include, but are not limited to, a neuroprotective therapeutic agent, an anti-oxidant, an anti-inflammatory agent, an immunosuppressive calcineurin inhibitor, a NOS inhibitor, a sigma-1 modulator, an AMPA antagonist, a $Ca^{2+}$ channel blocker and combinations thereof.

In some embodiments, the therapeutic agent is a neuroprotective therapeutic agent. Any neuroprotective agent can be used. Examples of neuroprotective agents include, but are not limited to, brain-derived neurotrophic factor (BDNF), glial cell line-derived neurotrophic factor (GDNF), nerve growth factor (NGF), and ciliary neurotrophic factor (CNTF). In some embodiments, the neuroprotective agent includes the Cerebrolysin, which is a peptidergic cocktail including brain-derived neurotrophic factor (BDNF), glial cell line-derived neurotrophic factor (GDNF), nerve growth factor (NGF), and ciliary neurotrophic factor (CNTF).

The embodiments described herein should in no way be construed to be limited to the synthetic platelets described herein, but rather should be construed to encompass the use of additional synthetic platelets or secondary therapeutic agent, both known and unknown, that are effective in the treatment of a vascular injury or occlusive condition.

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for hypertrophy, vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

In various embodiments, a synthetic platelet described herein in combination with a second therapeutic agent may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, a synthetic platelet described herein and one or more other therapies are cyclically administered. Cycling therapy involves the administration of a first therapy (e.g., a synthetic platelet) for a period of time, followed by the administration of a second therapy (e.g., a second synthetic platelet or another therapeutic agent not encapsulated in a synthetic platelet) for a period of time, optionally, followed by the administration of a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

The dosages of a pharmaceutical composition disclosed herein may be adjusted when combined to achieve desired effects. On the other hand, dosages of the pharmaceutical composition and various therapeutic agents may be independently optimized and combined to achieve a synergistic result wherein the pathology is reduced more than it would be if either were used alone.

The formulations of the pharmaceutical compositions described herein may be prepared by any method known or hereafter developed in the art of pharmacology. In general, such preparatory methods include the step of bringing a synthetic platelet into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions, which are suitable for ethical administration to humans, it will be understood by the skilled artisan that such compositions are generally for administration to animals of all sorts. Modification of pharmaceutical compositions for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, animals including commercially relevant animals such as cattle, pigs, horses, sheep, cats, and dogs, birds including commercially relevant birds such as chickens, ducks, geese, and turkeys.

Pharmaceutical compositions that are useful in the methods described herein may be administered, prepared, packaged, and/or sold in formulations for parenteral, oral, rectal, vaginal, topical, transdermal, pulmonary, intranasal, buccal, ophthalmic, or another route of administration.

The compositions described herein may be administered via numerous routes, including, but not limited to, parenteral, oral, rectal, vaginal, topical, transdermal, pulmonary, intranasal, buccal, or ophthalmic administration routes. The route(s) of administration will be readily apparent to the skilled artisan and will depend upon any number of factors including the type and severity of the disorder being treated, the type and age of the veterinary or human patient being treated, and the like.

Parenteral administration of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition on or through a surgical incision, by application of the composition on or through a tissue-penetrating non-surgical wound, and the like. In particular, parenteral administration is contemplated to include, but is not limited to, cutaneous, subcutaneous, intraperitoneal, intramuscular, intrasternal injection, intravenous, and intra-arterial.

Formulations of a pharmaceutical composition suitable for parenteral administration comprise the therapeutic agent combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles. Such formulations may further comprise one or more additional ingredients including, but not limited to, suspending, stabilizing, or dispersing agents. In one embodiment of a formulation for parenteral administration, the therapeutic agent is provided in dry (i.e., powder or granular) form for reconstitution with a suitable vehicle (e.g., sterile pyrogen free water) prior to parenteral administration of the reconstituted composition.

Pharmaceutical compositions that are useful in the methods described herein may be administered systemically in oral solid formulations, ophthalmic, suppository, aerosol, topical or other similar formulations. In addition to the synthetic platelet, such pharmaceutical compositions may contain pharmaceutically acceptable carriers and other ingredients known to enhance and facilitate administration.

The pharmaceutical compositions described herein may also be formulated so as to provide slow, prolonged or controlled release. In general, a controlled-release preparation is a pharmaceutical composition capable of releasing the synthetic platelet at a desired or required rate to maintain constant activity for a desired or required period of time.

A pharmaceutical composition described herein may be prepared, packaged, or sold in bulk, as a single unit dose, or as a plurality of single unit doses. As used herein, a "unit dose" is discrete amount of the pharmaceutical composition comprising a predetermined amount of the activity. The amount of the activity is generally equal to the dosage, which would be administered to a subject or a convenient fraction of such a dosage such as, for example, one-half or one-third of such a dosage.

The relative amounts of the ingredients in a pharmaceutical composition of the invention will vary, depending upon the identity, size, and condition of the subject treated and further depending upon the route by which the composition is to be administered. By way of a non-limiting example, the composition may comprise between 0.1% and 100% (w/w) of the synthetic platelets.

One of skill in the art will recognize that the amount of the synthetic platelets in these formulations can vary widely, and will be selected primarily based on fluid volumes, viscosities, body weight, particular therapeutic agent encapsulated and the like in accordance with the particular mode of administration selected and the subject's needs. In some embodiments, the synthetic platelet compositions described herein may be administered to deliver a dose of between 1 ng/kg/day and 100 mg/kg/day. In one embodiment, a dose can be administered that results in a concentration of the synthetic platelets between 1 µM and 10 µM in a mammal. While the precise dosage administered will vary depending upon any number of factors, including but not limited to, the type of animal, the site targeted, the type of vascular injury or occlusive condition treated, the amount of bleeding being treated, the type of wound being treated, the age of the animal and the route of administration. Preferably, the dosage of the synthetic platelet will vary from about 1 µg to about 50 mg per kilogram of body weight of the animal.

More preferably, the dosage will vary from about 10 µg to about 15 mg per kilogram of body weight of the animal. Even more preferably, the dosage will vary from about 100 µg to about 10 mg per kilogram of weight of the animal. In some embodiments, dosing of a subject can be readily calculated based on the drug loading efficacy (EE) of nanoparticles described herein loaded with one or more therapeutic agents.

The pharmaceutical compositions may be prepared, packaged, or sold in the form of a sterile injectable aqueous or oily suspension or solution. This suspension or solution may be formulated according to the known art, and may comprise, in addition to the therapeutic agent, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical composition may be administered to an animal as needed. The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

EXAMPLES

The application is further described in detail by reference to the following examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Past approaches on mimicking platelet's hemostasis-relevant functions on synthetic platforms have mainly focused on amplifying platelet's 'aggregation' functionality by decorating synthetic particle surfaces with aggregation-promoting biomolecules like Fibrinogen (Fg) or Fg-derived peptide sequences. For example, synthetic particle platforms like liposomes, albumin spheres and synthetic polymeric particles have been surface-decorated with platelet membrane-derived glycoproteins, Fg, Fg-derived Arginine-Glycine-Aspartic Acid (RGD) peptides and Fg-derived H12 dodecapeptides. All of these are essentially various designs of 'super-fibrinogen' particles that can amplify the aggregation of active platelets due to their increased surface-valency of platelet-bridging motifs (i.e., Fg or Fg-derived peptides), compared to hexavalent Fg itself. However, in natural primary hemostasis, platelet aggregation is preceded by stable platelet adhesion at the injury site under blood flow, as shown in FIG. 1.

Platelet adhesion is mediated by shear-dependent binding of the GPIbα extracellular domain of the platelet surface glycoprotein GPIb/IX/V complex with von Willebrand factor (vWF) secreted from the injured endothelium, augmented by binding of platelet surface glycoproteins GPIa/IIa and GPVI to sub-endothelial collagen. The vWF-binding helps in the initial arrest and rolling of platelets at the injury site, while collagen binding stabilizes the adhered platelets under the hemodynamic flow environment. These adhesion mechanisms result in platelet activation signaling, ultimately leading to a ligand-binding conformational change of the platelet surface integrin GPIIb-IIIa that then binds to Fg to promote aggregation of the activated platelets to form the primary hemostatic plug.

In this example, we show bioengineering of synthetic constructs where vWF-binding and collagen-binding ligand motifs are integrated on the same particle (FIG. 2), and investigate their platelet-mimetic adhesive capabilities under physiologically relevant flow environment (wall shear stresses) in vitro, using a parallel plate flow chamber (PPFC). For vWF-binding, we have investigated a small synthetic peptide with amino acid sequence TRYL-RIHPQSWVHQI (SEQ ID NO: 1), that is derived from the C2 domain (residues 2303-2332) of the coagulation factor FVIII which is known to form complex with vWF prior to thrombin or factor Xa catalyzed activation in the coagulation cascade. We have compared the vWF-binding of liposomes surface-decorated with this vWF-binding peptide (VBP) to liposomes surface-decorated with the previously reported recombinant GPIbα fragment. For collagen binding, we have investigated a short 7-repeat of the Glycine(G)-Proline (P)-Hydroxyproline(O) tri-peptide (i.e., -[GPO]$_7$-), with helicogenic affinity to fibrillar collagen. This small collagen-binding peptide (CBP) can promote adhesion to fibrillar collagen, but cannot activate quiescent platelets due to absence of long triple-helical conformation. We have demonstrated that that the vWF-binding constructs undergo enhanced adhesion under increasing wall shear, while the collagen-binding constructs undergo stable adhesion in an apparent shear-independent fashion. Furthermore, we have integrated simultaneous vWF-binding and collagen-binding motifs on the same liposome platform and have investigated their adhesion capability to a vWF/collagen mixed surface under flow, in vitro. In such heteromultivalent liposome surface decoration, we have demonstrated that the platelet-mimetic dual adhesion mechanisms (simultaneous vWF-binding and collagen-binding) can be successfully achieved provided the vWF-binding and the collagen-binding ligand motifs do not spatially interfere each other while conjugated onto the liposome surface. Altogether, by surface engineering of liposomes via decoration of specific ligands, we demonstrate efficient molecular mimicry of platelet's dual adhesion mechanisms. This approach can be potentially adapted to various particle platforms to optimize the design of a platelet-mimetic synthetic bioconjugate construct.

Materials

Cholesterol, Dimethyl Sulfoxide (DMSO) and collagen were purchased from Sigma Aldrich (St. Louis, Mo., USA). The lipids Distearyl Phosphatidyl Choline (DSPC), 2000 M W Polyethylene glycol-modified Distearyl Phosphatidyl Ethanolamine (DSPE-PEG$_{2000}$), and Carboxy-terminated Polyethylene glycol-modified DSPE (DSPE-PEG$_{2000}$-COOH) were purchased from Avanti Polar Lipids (Alabaster, Ala., USA). Human vWF (FXIII free) was purchased from Hematologic Technologies Incorporation (Essex Jn, Vt., USA). The Parallel Plate Flow Chamber (PPFC) system was purchased from Glycotech (Gaithersburg, Md., USA).

Ligand Motifs vWF-Binding Motifs

For vWF binding, a recombinant GPIbα fragment (rGPIbα) containing the vWF binding sites (residues 1 to 302) or a short chain vWF-binding peptide (VBP) was used. The GPIbα fragment was expressed in CHO cells and isolated, adapting methods described by Murata et al. The VBP, TRYLRIHPQSWVHQI, was synthesized using Fluorenylmethyloxycarbonyl chloride (FMoc)-based solid phase chemistry on Knorr resin, and characterized using mass spectroscopy. Each vWF molecule has only one binding region for this peptide, and hence we rationalized that pre-coated vWF surface or shear-enhanced multimerization of vWF on collagen-coated surface will present multiple binding sites for multiple copies of this peptide decorated on the liposome surface, thereby providing a mechanism for enhanced adhesion of the liposomes with increasing shear.

Collagen-Binding Motifs

The CBP, [GPO]7, was also synthesized using FMoc-based solid phase chemistry on Knorr resin, and characterized using mass spectroscopy. The GPO trimer is based on amino acid repeats found in the native collagen structure. It has been reported that the activation of platelets usually caused by interaction with collagen through GPVI and GPIa/IIa, can also potentially occur when platelets interact with collagen-derived peptides. This can be a potential problem regarding decorating synthetic particle surfaces with collagen-derived peptides for binding of collagen, because in vivo the constructs can potentially interact with quiescent blood platelets and systemically activate them, posing thromboembolic risks. However, it has been reported that interaction of platelet receptors with collagen and the subsequent platelet activation mechanisms are dependent upon receptor clustering induced by multimeric long chain triple-helical fibrillar collagen and not by short collagen-mimetic peptide repeats. In fact, it has been shown that GPO-trimer repeats as high as a 30-mer (10 repeats) only partially interact with platelet GPIa/IIa and GPVI integrins and are incapable of activating platelets; yet they can effectively bind to fibrillar collagen via helicogenic interaction. Hence, we rationalized that our 7-mer short chain monomeric CBP will not activate quiescent platelets in circulation but can still allow binding of CBP-decorated liposomes to collagen covered surface, under flow.

The mass spectrometric characterization data of the peptides are available in the Supporting Information. Also, the inability of both VBP and CBP to activate platelets was confirmed by aggregometry, and this data is also available in the Supporting Information.

Ligand-Modified Liposomal Construct Fabrication

The rGPIbα, VBP or CBP were conjugated to DSPE-PEG-COOH using carbodiimide-mediated amidation chemistry to form DSPE-PEG-ligand molecules, utilizing previously reported methods. To fluorescently label the liposomes, DSPE-Fluorescein (green fluorescence, λmax~530 nm) was synthesized by reacting the free amine (—NH2) termini of DSPE with NHS-Fluorescein at basic pH. Specific proportions of the DSPE-PEG-rGPIbα, DSPE-PEG-VBP or DSPE-PEGCBP were combined with unmodified DSPE-PEG, DSPC, cholesterol, and DSPE-Fluorescein to fabricate peptide-decorated green fluorescent liposomal constructs, using the standard reverse phase evaporation and extrusion technique. The liposome size distribution, characterized using dynamic light scattering (DLS), was found to be ~150 nm (c.f. Supporting Information).

Parallel Plate Flow Chamber (PPFC)

The PPFC setup is appropriate for biomolecular interaction analysis under a dynamic shear flow environment. In the PPFC, by maintaining Renyold's number in the 'laminar' range (~10$^5$), the wall shear stress can be modulated as a function of flow rate (Q) by:

$$\tau_w = \frac{6\mu Q}{bh^2} \quad (1)$$

where μ=fluid viscosity, b=width of the chamber, and h=distance between plates. For our experiments, b/h was >20 and Q was maintained to provide $\tau_w$ in the range of 5-55 dynes/cm2, which covers a substantial range of physiological shear in blood flow. Distinct circular areas on glass slides were coated with collagen, vWF or 50:50 mixture of vWF:collagen (test surfaces) and Bovine Serum Albumin (BSA, negative control surface with no adhesion specificity). The coated slides were vacuum-sealed into the PPFC for subsequent experiments.

Platelet-Mimetic Adhesion Studies Under Flow In Vitro

For studying platelet-mimetic vWF-adhesive functionality, 5 mol % DSPE-PEG-rGPIbα or DSPE-PEG-VBP was combined with DSPC (49 mol %), cholesterol (40 mol %), DSPE-PEG (5 mol %), and DSPE-Fluorescein (1 mol %) to form the final liposomal construct. The fluorescein labeled (green fluorescent, λmax=530 nm) liposomes, at a concentration of 10 M total lipid, were allowed to flow through the PPFC in a closed loop over vWF-coated and BSA-coated surface under various flow rates to produce wall shear stresses from 5-55 dynes/cm$^2$ for 30 mins. After 30 minutes, flow of just PBS was maintained in an open loop for an additional 15 minutes in order to remove any loosely bound constructs and gain insight on the adhesion stability and retention of the constructs on the test and control surfaces. The slides were imaged at various time points (5, 15, 30, and 45 mins) of flow in the PPFC, using an inverted epifluorescence microscope (Carl Zeiss Axio Observer D1) with a photometrics chilled CCD camera (Axiocam MRM) and a 63× objective. Images were collected using Axiovision™ software with fixed exposure times of 400 ms. From each image, extent of adhesion and retention was quantified by measuring surface-averaged fluorescence intensity using the Axiovision software. Statistical analysis of fluorescence intensity was performed using ANOVA and significance was considered as p<0.05. FIG. 3A shows a schematic view of the PPFC experimental set-up and the expected interaction of the vWF-binding liposomal constructs with the test and control surface regions. In an additional experimental design, we aimed to investigate if soluble vWF could adhere to collagen and multimerize under high shear stress, and then induce adhesion of VBP decorated liposomes. This is inspired by the natural physiological mechanism where soluble vWF adheres to exposed sub-endothelial collagen, multimerizes under shear and subsequently allows adhesion of platelets via interaction with platelet surface GPIbα. For this, green fluorescent VBP-modified liposomes and soluble FVIII-free human vWF were introduced into the PPFC and allowed to flow over collagen-coated surface or albumin-coated surface under high shear stress of 55 dynes/cm$^2$ for 5-30 min and the adhesion of the liposomes over time was imaged with epifluorescence microscopy using the microscope set-up described previously.

For studying platelet-mimetic collagen-adhesive functionality, 5 mol % DSPE-PEG-CBP was combined with DSPC (49 mol %), cholesterol (40 mol %), DSPE-PEG (5 mol %), and DSPEFluorescein (1 mol %) to form the final liposomal construct. These fluorescently labeled liposomes were allowed to flow through the PPFC over collagen-coated and BSA-coated surfaces in the same way as VBP-decorated liposomes, i.e., 30 min in closed loop followed by 15 min open loop circulation of just PBS. Imaging at various time points and image analysis were carried out as before. FIG. 5A shows a schematic view of the PPFC experimental set-up and the expected interaction of the CBP-decorated liposomes with the test and control surfaces.

For studying cumulative effects of simultaneous vWF and collagen-binding, 2.5 mol % DSPEPEG-rGPIbα or DSPE-PEG-VBP and 2.5 mol % of CBP were combined with DSPC (49 mol %), cholesterol (40 mol %), DSPE-PEG (5 mol %), and DSPE-Fluorescein (1 mol %) to form the final heteromultivalently decorated liposomal constructs. These fluorescently labeled liposomes were allowed to flow in the PPFC over a surface coated with 50:50 vWF:collagen (mixed coating) under 5-55 dyn/cm$^2$ shear stress, and the imaging and image analysis were carried out as before.

For all adhesion studies, besides testing the interaction of ligand-modified liposomes on negative control albumin surfaces, additional control studies were also carried out by testing unmodified (no surface decoration) liposomes on vWF-coated, collagen-coated or mixed-coated surfaces.

Results

Platelet-Mimetic vWF Adhesion of Ligand-Decorated Liposomes Under Flow In-Vitro

Figure 3C:
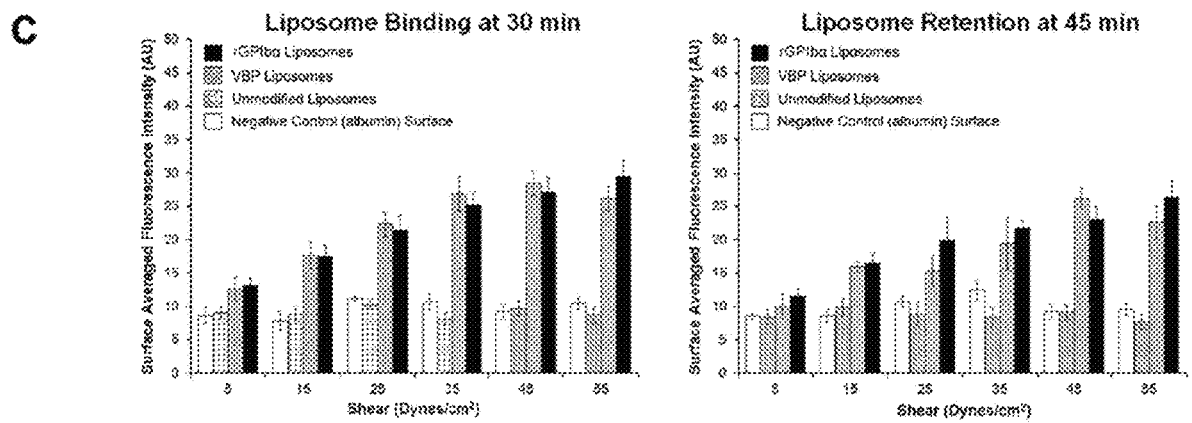
FIGS. 3(A-C) illustrate representative results from PPFC studies using rGPIbα- or VBP-decorated liposomal constructs allowed to flow over vWF-coated surface versus albumin surface. (A) schematic of experimental set-up; (B) the ligand-modified liposomes showed minimal adhesion or retention on albumin surface and the unmodified liposomes showed minimal adhesion or retention on vWF surface, whereas the rGPIbα-modified and the VBP-modified liposomes both showed significant adhesion and retention on vWF surface under flow; (C) quantitative analysis of the adhesion (at 30 min) and retention (at 45 min) data using surface-averaged fluorescence intensity shows that both rGPIbα-modified and VBP-modified liposomes undergo increasing adhesion and retention on vWF surface under increasing shear, mimicking the vWF-binding of platelets.

FIG. 3B shows a representative set of fluorescence images from PPFC experiments using rGPIbα-decorated liposomes and VBP-decorated liposomes on vWF-coated surfaces versus albumin-coated surfaces under flow. Although images were taken at six shear values between 5-55 dynes/cm$^2$ and at four time points during flow between 5-45 mins for each of the liposomal constructs, representative fluorescent images are shown at only two shear values (5 and 35 dynes/cm$^2$) and two time points (30 and 45 minutes) for convenience. FIG. 3C shows the quantitative analysis of surface-averaged fluorescence intensity values from the adhesion of the various liposomal constructs on vWF-coated surfaces over the entire shear stress range at 30 minutes and 45 minutes. Statistical analysis of fluorescence intensity values shows that both rGPIbα-decorated and VBP-decorated liposomal constructs undergo increased adhesion on the vWF-coated surfaces with increasing shear, while on albumin-coated surfaces both types of constructs showed only minimal adhesion irrespective of shear stress values. In addition, the unmodified liposomes showed minimal adhesion to vWF at all shear stress ranges.

Figure 4:
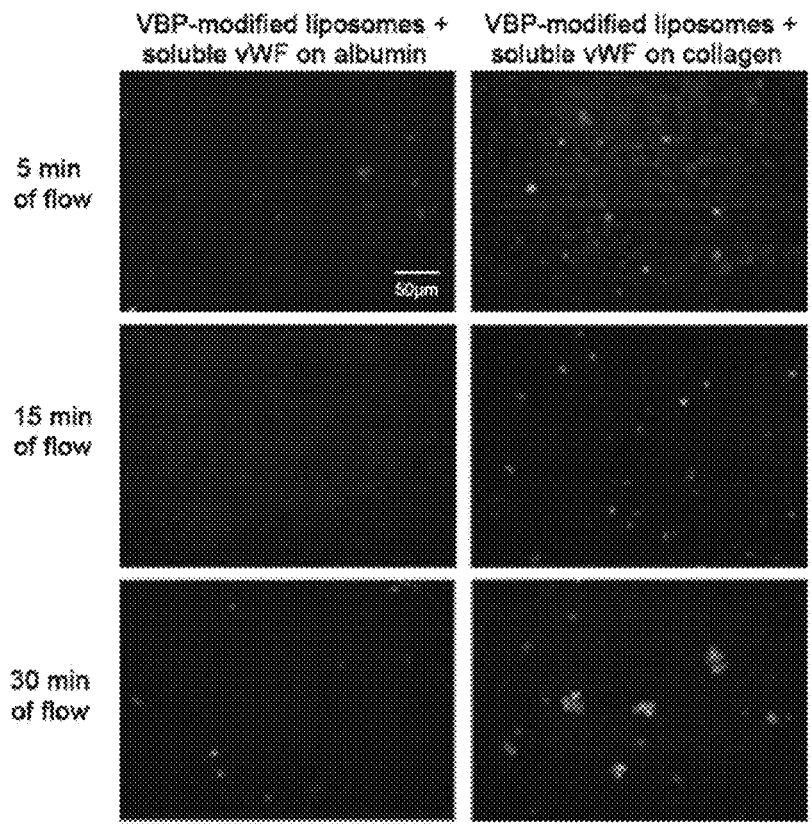
FIG. 4 illustrates representative fluorescent micrographs from PPFC experiments where VBP-modified liposomes were allowed to flow with soluble vWF over collagen surface versus albumin surface under high shear (55 dynes/cm$^2$). Soluble vWF cannot adhere and multimerize on albumin surface, but can adhere and multimerize on collagen surface; consequently with time (5 min to 30 min of flow) the soluble vWF formed larger multimerized areas on collagen surface, allowing higher extent of adhesion of green fluorescent VBP-modified liposomes. Adhesion of VBP modified liposomes on the albumin surface was minimum since there was no vWF multimerization on albumin.

FIG. 4 shows representative fluorescent images from the additional experimental design involving flow of soluble vWF and VBP-modified liposomes over collagen or albumin surface under high shear stress. Representative results are shown for a shear stress value of 55 dynes/cm$^2$ for three time-points of 5 min, 15 min and 30 min of flow. As evident from the results, green fluorescent VBP-modified liposomes are able to adhere when introduced along with soluble vWF to flow over a collagen-coated surface, but not on an albumin-coated surface. Furthermore, the VBP-modified liposomes seemed to undergo enhanced amount of adhesion (larger fluorescent 'patch' areas) with time, under the high shear value.

Figure 5C:
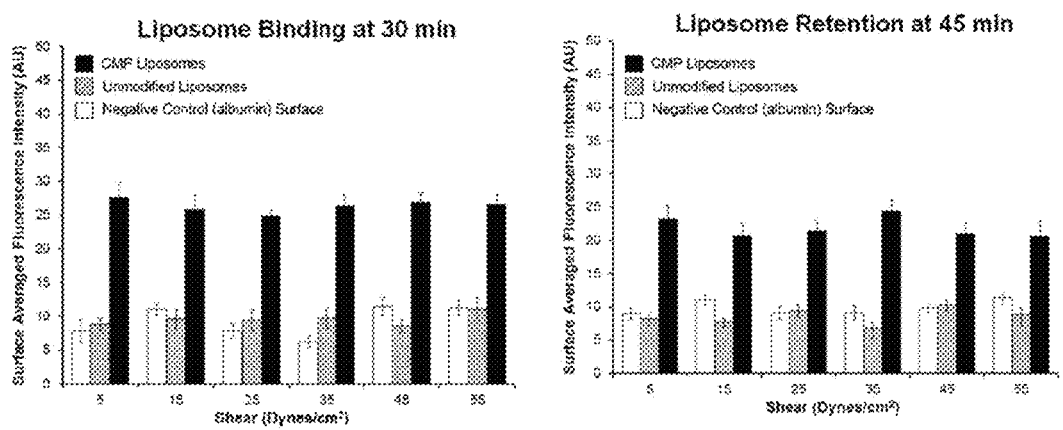
FIGS. 5(A-C) illustrate representative results from PPFC studies using CBP-decorated liposomal constructs allowed to flow over collagen-coated surface versus albumin surface. (A) schematic of experimental set-up; (B) the ligand-modified liposomes showed minimal adhesion or retention on albumin surface and the unmodified liposomes showed minimal adhesion or retention on collagen surface, whereas the CBP-modified liposomes showed significant adhesion and retention on collagen surface under flow; (C) quantitative analysis of the adhesion (at 30 min) and retention (at 45 min) data using surface-averaged fluorescence intensity shows that the CBP modified liposomes undergo enhanced adhesion and retention on the collagen surface in a shear independent fashion.

Platelet-Mimetic Collagen Adhesion of Ligand-Decorated Liposomes Under Flow In-Vitro FIG. 5B shows a representative set of fluorescence images from PPFC experiments using CBP decorated liposomes on collagen-coated surfaces versus albumin-coated surfaces under flow. As before, the representative images are shown at only two shear values (5 and 35 dynes/cm$^2$) and two time points (30 and 45 minutes) for convenience. FIG. 5C shows quantitative analysis of the surface-averaged fluorescence intensity values from the adhesion of the various liposomal constructs on collagen-coated surfaces over the entire shear stress range at 30 min and 45 min. Statistical analysis of fluorescence intensity measurements shows the CBP-decorated liposomal constructs undergo significant adhesion to collagen-coated surfaces under flow with no apparent shear-dependent effect, but minimal adhesion to albumin surfaces. In addition, the unmodified constructs showed minimal adhesion on collagen surfaces.

Combining vWF-Adhesion and Collagen Adhesion on the Surface of Liposomes In Vitro FIG. 6A shows representative set of fluorescence images for adhesion of liposomes surface decorated with both rGPIbα and CBP (2.5 mol % each), or both VBP and CBP (2.5 mol % each), onto a mixed coated (vWF:collagen 50:50) surface under flow in the PPFC. The adhesion of unmodified liposomes on these mixed coated surfaces and the adhesion of the ligand-modified liposomes on the negative control (albumin) surfaces are also shown in the figure for comparison. As before, the representative images are shown at only two shear values (5 and 35 dynes/cm$^2$) and two time points (30 and 45 minutes) for convenience. FIG. 6B shows the quantitative analyses of the fluorescence intensity data from the adhesion of the various heteromultivalent liposomal constructs over the entire shear stress range, compared with the adhesion data for liposomes bearing rGPIbα-decorations only, VBP-decorations only and CBP decorations only, all on mixed coated (vWF: collagen 50:50) surfaces. As evident from the fluorescent images, as well as, the quantitative data, liposomes bearing both rGPIbα and CMP showed enhanced adhesion on the mixed coated surface with increasing shear, but this was not statistically different from liposomes bearing rGPIbα modification alone. In comparison, liposomes bearing both VBP and CBP not only showed enhanced adhesion to the mixed coated surface under increasing shear, but the levels of adhesion were significantly higher than liposomes bearing VBP decoration or CBP decoration alone.

Our results indicate that the shear-dependent enhancement in adhesion of the rGPIbα-decorated or VBP-decorated liposomal constructs were due to specific interactions of the ligands to the vWF surface, since the same liposomes showed only minimum adhesion on albumin surfaces. Furthermore, the results from experiments with VBP-decorated liposomes and soluble vWF under flow on collagen surfaces suggest that possible multimerization of the soluble vWF with time on the collagen surface under high shear allows increased adhesion of VBP-decorated liposomes on the vWF-rich areas, as indicated by formation of larger fluorescent patches with time. Altogether, these results demonstrate successful mimicry of shear-dependent platelet adhesion to vWF using surface-engineered liposomes. The results from interaction of CBP-decorated liposomes on collagen-coated surface indicate that the adhesion is mostly shear-independent and is due to specific helicogenic interaction of the CBP with collagen. Hence, these data establish successful mimicry of the collagen-binding property of platelets with CBP-decorated liposomes. Analysis of the results from experiments with liposomes simultaneously bearing vWF-binding and collagen-binding motifs suggest that when decorated simultaneously on the liposomal surface, the larger rGPIbα motif (~300 amino acid residues) possibly masks the much smaller CBP motif (~21 residues), thereby preventing the combination effect of simultaneous vWF-binding and collagen-binding by the liposomes. The resultant adhesion seems to happen principally due to only rGPIbα-vWF interaction in a shear-dependent fashion. In contrast, when VBP (~15 amino acid residues) is used in conjunction with CBP for liposome surface decoration, these two small peptides possibly do not mask each other's specific interactions and therefore a combined effect of vWF-binding and collagen-binding becomes evident in the enhanced adhesion of the heteromultivalent liposomal constructs on the mixed coated surfaces under flow. Hence we demonstrate that by decorating a synthetic particle (liposome) surface with ligands binding simultaneously to vWF and collagen, and ensuring that the decorated ligands do not spatially mask each other, we can successfully mimic the hemostatically relevant dual adhesion mechanisms of platelets.

The functional biomimetic design of a platelet-mimetic synthetic construct should incorporate both the 'adhesion' functionalities and the 'aggregation' functionalities of natural platelets. We envision that platelet-mimetic hemostatic efficacy of synthetic constructs can be further enhanced if the 'aggregation'-promoting component and 'adhesion'-promoting component can be combined on the same particle. Therefore, in subsequent studies, we will combine the adhesion-promoting VBP and CBP motifs along with aggregation-promoting Fg-mimetic RGD peptide motifs on the same liposome, and investigate whether these functionally integrated constructs can themselves adhere to vWF/collagen surfaces under flow and promote recruitment and aggregation of platelets at the sites of liposome adhesion.

It is to be noted that the model particle used in our studies were spherical unilamellar liposomes about 150 nm in diameter. Several recent mathematical modeling and experimental studies have demonstrated that there exist significant correlations between the shape and size of particles to their location in hemodynamically relevant flow patterns. For natural platelets, their hemostatic functions at the vessel wall depend upon their ability of 'margination' to the wall injury site through RBCs and other blood components. This hemodynamic migration is significantly influenced by platelet's shape and size. Based on such observations, we can show an additional component of synthetic platelet design will optimization of particle geometry (size and shape) that can facilitate enhanced wall-margination of the particles. An ideal biomimetic design of a synthetic platelet can be achieved by integration of margination favoring optimal physical parameters (size and shape) with adhesion- and aggregation-promoting optimal biological parameters (chemistry and density of ligand modifications). Also, these design components and resultant insight can provide novel avenues to target such particles as efficient drug delivery vehicles to vascular disease sites with exposed vWF or collagen.

Example 2

We describe in this example the development and experimental results from integrating platelet-mimetic adhesion- and aggregation-promoting functionalities on a single particle, by decorating the surface of 150 nm diameter liposomes simultaneously with three peptides, a vWF-binding peptide (VBP), a collagen-binding peptide (CBP) and an active platelet GPIIb-IIIa-binding peptide (cRGD). We have previously demonstrated in Example 1 that liposomes bearing VBP and CBP motifs undergo platelet-mimetic adhesion under flow on vWF and collagen-coated surfaces in vitro at low-to-high shear, in parallel plate flow chamber (PPFC) experiments. Here, we demonstrate that cRGD-modified liposomes pre-adhered to a surface can enhance the aggregation of ADP-activated platelets onto them, even at a low platelet concentrations. Subsequently, we demonstrate that liposomes bearing all three peptides (VBP, CBP and cRGD), when introduced in PPFC flow along with low concentration of ADP-activated platelets over a vWF/collagen mixed coated surface, are able to adhere to the surface under high shear and promote arrest and aggregation of active platelets onto sites of liposome adhesion.

Materials and Methods

Materials

Phosphate Buffered Saline (PBS), 3.8% w/v sodium citrate, parformaldehyde (PFA), Avidin, Bovine Serum Albumin (BSA), and ethanol were purchased from Thermo Fisher Scientific (Pittsburgh, Pa., USA). Cholesterol, Dimethyl Sulfoxide (DMSO), and collagen were purchased from Sigma Aldrich (St. Louis, Mo., USA). Fluorescently labeled monoclonal antibody, AlexaFluor® 647-anti-CD62P (staining activated platelet P-selectin), was purchased from BioLegend (San Diego, Calif., USA). The lipids Distearyl Phosphatidyl Choline (DSPC), Distearyl Phosphatidyl Ethanolamine (DSPE), Polyethylene Glycol-modified DSPE (DSPE-PEG2000), Carboxy-polyethylene Glycol-modified DSPE (DSPE-PEG2000-COOH), and Biotinylated Polyethylene Glycol-modified DSPE (DSPE-PEG2000-Biotin) were purchased from Avanti Polar Lipids (Alabaster, Ala., USA). ClearOx® and N-Hydroxysuccinimide-modified Fluorescein (NHS-Fluorescein) was purchased from Invitrogen Corporation (Carlsbad, Calif., USA). Human vWF (FXIII free) was purchased from Hematologic Technologies Incorporation (Essex Jn, Vt., USA). The Parallel Plate Flow Chamber (PPFC) system for dynamic flow studies was purchased from Glycotech (Gaithersburg, Md., USA). The peptide sequences used were TRYLRIHPQSWVHQI (VBP), (SEQ ID NO: 1), [GPO]$_7$ (CBP) (SEQ ID NO: 2), and cyclo-CNPRGDY(OEt)RC (cRGD) (SEQ ID NO: 3). The VBP, CBP and the linear precursor of the cRGD peptide were synthesized using Fluorenylmethyloxycarbonyl chloride (FMoc)-based solid phase chemistry on Knorr resin and characterized using mass spectroscopy. The linear precursor of cRGD was subjected to sulfhydril oxidation of Cysteine termini using ClearOx® reagent, to achieve disulphide-based cyclization.

Preparation of Platelet Suspensions

Venous blood from healthy, medication-free, adult donors was drawn into 3.8% w/v sodium citrate anticoagulant at a 9:1 ratio (by volume), in compliance with CWRU IRB-approved protocols. Platelet Rich Plasma (PRP) was obtained by centrifuging the human whole blood at 150 g for 15 min and platelet count was monitored using a Coulter Counter. In order to prepare thrombocytopenic condition-mimicking low platelet concentrations (LPC), a portion of PRP was further centrifuged at 2500 g for 25 mins, to obtain platelet-poor plasma (PPP). This PPP was then added volumetrically to PRP such that final platelet concentration was adjusted to ~20,000/μl, as monitored by Coulter Counter. These LPC suspensions were used immediately.

Fabrication of Surface-Modified Liposomes

Figure 7:
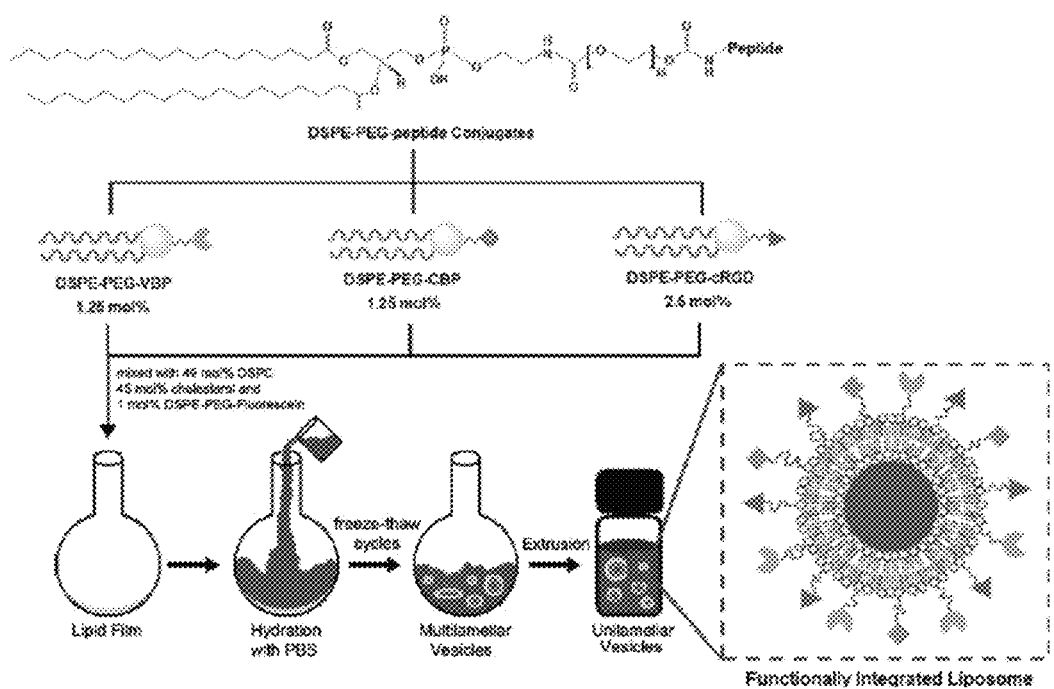
FIG. 7 is a schematic of methods to fabricate functionally integrated liposomes bearing VBP and CBP peptides for platelet-mimetic vWF and collagen adhesion under flow and cRGD peptides to promote arrest and aggregation of active platelets via interaction with integrin GPIIb/IIIa.

The VBP, CBP and cRGD peptides were conjugated via their N-termini to the carboxyl terminus of DSPE-PEG$_{2000}$-COOH via standard carbodiimide chemistry adapting previously reported methods, resulting in the various DSPE-PEG-peptide molecules. NHS-Fluorescein was reacted with DSPE-PEG$_{2000}$-COOH to form DSPE-PEG-fluorescein for fluorescent labeling of liposomes. DSPE-PEG-peptides were mixed at specific mol % with DSPC, cholesterol, DSPEPEG, DSPE-PEG-Biotin and DSPE-PEG-fluorescein as needed and such mixed lipid formulations were used towards fabricating liposomes via standard reverse phase evaporation and extrusion technique. The extrusions were carried out near the transition temperature of DSPC (~60° C.) through nanoporous (200 nm pore-size) polycarbonate membranes, resulting in unilamellar liposomal constructs of 150 nm average diameter. A general schematic of fabricating the 'functionally integrated' liposomes (simultaneously bearing all three peptides VBP, CBP and cRGD) is shown in FIG. 7.

In-Vitro Platelet Aggregation Studies

For studying whether the cRGD-modified liposomal constructs pre-adhered to a surface can induce aggregation of activated platelets even from low platelet concentrations, DSPC (49 mol %), cholesterol (45 mol %), DSPE-PEG (2.5 or 5 mol %), and DSPE-PEG-Biotin (1 mol %) was combined with or without DSPE-PEG-cRGD (2.5 mol %), to form cRGD-modified or unmodified biotinylated liposomal constructs. These non-fluorescent cRGD-modified or unmodified biotinylated liposomes were incubated with the avidin-coated glass coverslips for 1 hour and subsequently washed with PBS to remove any loosely-bound liposomes. This produced coverslips with a stable coating of cRGD-modified or unmodified liposomal constructs, as shown in the schematic of coverslips in the left columns of FIG. 8. LPC was obtained as described previously and incubated with the construct-coated coverslips for 1 hr in the absence or in presence of platelet agonist ADP, under gentle agitation. Post-incubation, the coverslips were gently washed with PBS to remove loosely-bound platelets from the construct-coated surface. Subsequently, the coverslips were stained with mouse anti-human Alexa Fluor® 647-anti-CD62P (red fluorescence, $\lambda$max~570 nm) that labels P-selectin on activated platelets. These stained coverslips were mounted onto glass slides and the fluorescence of active platelets aggregated onto the coverslips was imaged using inverted fluorescence microscopy. The working hypothesis behind these experiments was that coverslips coated with cRGD-modified liposomal constructs would induce GPIIb-IIIa-binding mediated enhanced aggregation of ADP-activated platelets, compared to the controls. In the absence of cRGD-modification on liposomes (unmodified liposome coating), a percentage of ADP-activated platelets may still undergo some clustering mediated by the fibrinogen present in the plasma of LPC suspension, but these platelet clusters will only aggregate minimally on the unmodified liposome surface since bare or PEGylated phospholipids (liposome membrane component) are known to prevent platelet adhesion and arrest 24. Platelet aggregation was quantified as the percentage of coverslip surface area covered by platelet fluorescence. All statistical analysis was performed using ANOVA and significance was considered as $p<0.05$.

In-Vitro Evaluation of Functionally Integrated Liposomal Constructs

Figure 9:
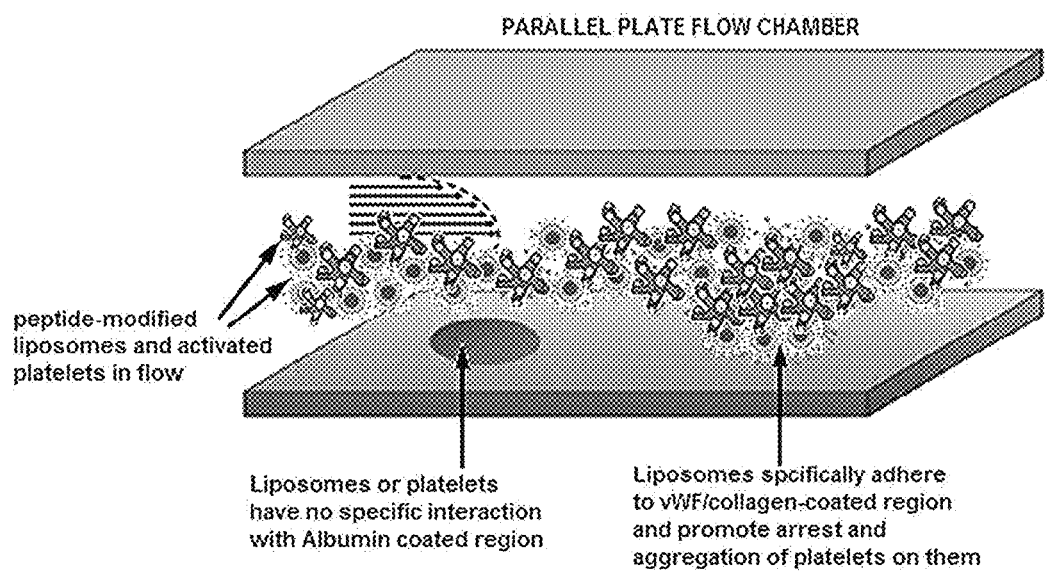
FIG. 9 is a schematic of the parallel plate flow chamber (PPFC) preparation with adjacent albumin-coated (negative control) and mixed (vWF/collagen)-coated areas and anticipated interaction of peptide (VBP and CBP)-modified liposomes with the surfaces under flow.

For developing functionally integrated liposomal constructs where the platelet-mimetic 'matrixadhesion' and 'aggregation' properties are combined on a single particle platform, DSPE-PEGVBP (1.25 mol %), DSPE-PEG-CBP (1.25 mol %), and DSPE-PEG-cRGD (2.5 mol %) were combined with DSPC (49 mol %), cholesterol (45 mol %), and DSPE-PEG-Fluorescein (1 mol %). Negative control liposomal constructs did not contain any lipid-peptide conjugate in their formulations, but instead contained 5 mol % of DSPE-PEG. Comparison liposomal formulations contained only 'adhesion' functionality (1.25 nol % DSPE-PEG-VBP and 1.25 mol % DSPEPEG-CMP together with 2.5 mol % DSPE-PEG, 49 mol % DSPC, 45 mol % cholesterol and 1 mol % DSPE-Fluorescein) or only 'aggregatory' functionality (2.5 mol % DSPE-PEG-cRGD together with 2.5 mol % DSPE-PEG, 49 mol % DSPC, 45 mol % cholesterol and 1 mol % DSPEFluorescein). For the experiments, glass slides were coated with adjacent circular regions of albumin (control surface with no specific adhesive interaction with any liposome formulation) and 50:50 vWF:collagen (vascular injury site mimicking protein surface with adhesive interaction with VBP- and CBP-decorated liposomes). The coated glass slides were vacuum sealed within the PPFC chamber, with the coated sides exposed to the flow (schematic shown in FIG. 9). Platelets in LPC were pre-incubated with ADP and pre-stained with red fluorescent AlexaFluor anti-CD62P. These LPC suspensions were allowed to flow through the PPFC along with various formulations of green fluorescent liposomes (unmodified, only adhesive peptide modified, only aggregatory peptide-modified or functionally integrated ones modified by all peptides), over the coated glass slides. The flow was maintained to produce wall shear stresses of 5-55 dynes/cm$^2$ for 30 minutes in a closed loop circulation. After 30 minutes, flow of just PBS was maintained for an additional 15 minutes in an open loop to remove any loosely bound constructs and platelets. The working hypothesis for this experimental design was that, liposomal constructs bearing all three peptides (VBP, CBP and cRGD) will be able to stably adhere to the vWF/collagen surface under low-to-high shear flow, recruit activated platelets in flow and promote aggregation of the activated platelets onto them at sites of liposome adhesion. Liposomal constructs bearing only 'adhesive' peptides (VBP and CBP only) or only 'aggregatory' peptide (cRGD only) will have much reduced capability of demonstrating platelet mimetic dual functions of promoting adhesion and arrest/aggregation of active platelets from flowing LPC suspensions. The slides were imaged at various time points (5, 15, 30, and 45 mins) of flow, using an inverted fluorescence microscope. For each image, liposome fluorescence (green) and activated platelet fluorescence (red) intensity were quantified using the Axiovision software. The co-localization of these two fluorescence colors was considered as a quantitative measure of liposomes adhering to the vWF/collagen surface under flow and then promoting arrest and aggregation of activated platelets onto themselves. This co-localization is qualitatively shown in pseudocolored yellow overlay in the results. The co-localization was quantified using Axiovision software, by acquiring the percentage of green pixels that also had red pixels superposed on them (at fixed pixel size) for every image and multiplying this percentage with the pixel-averaged green fluorescence intensity for that specific image. All statistical analyses were performed using ANOVA and significance was considered at $p<0.05$.

Figure 8:
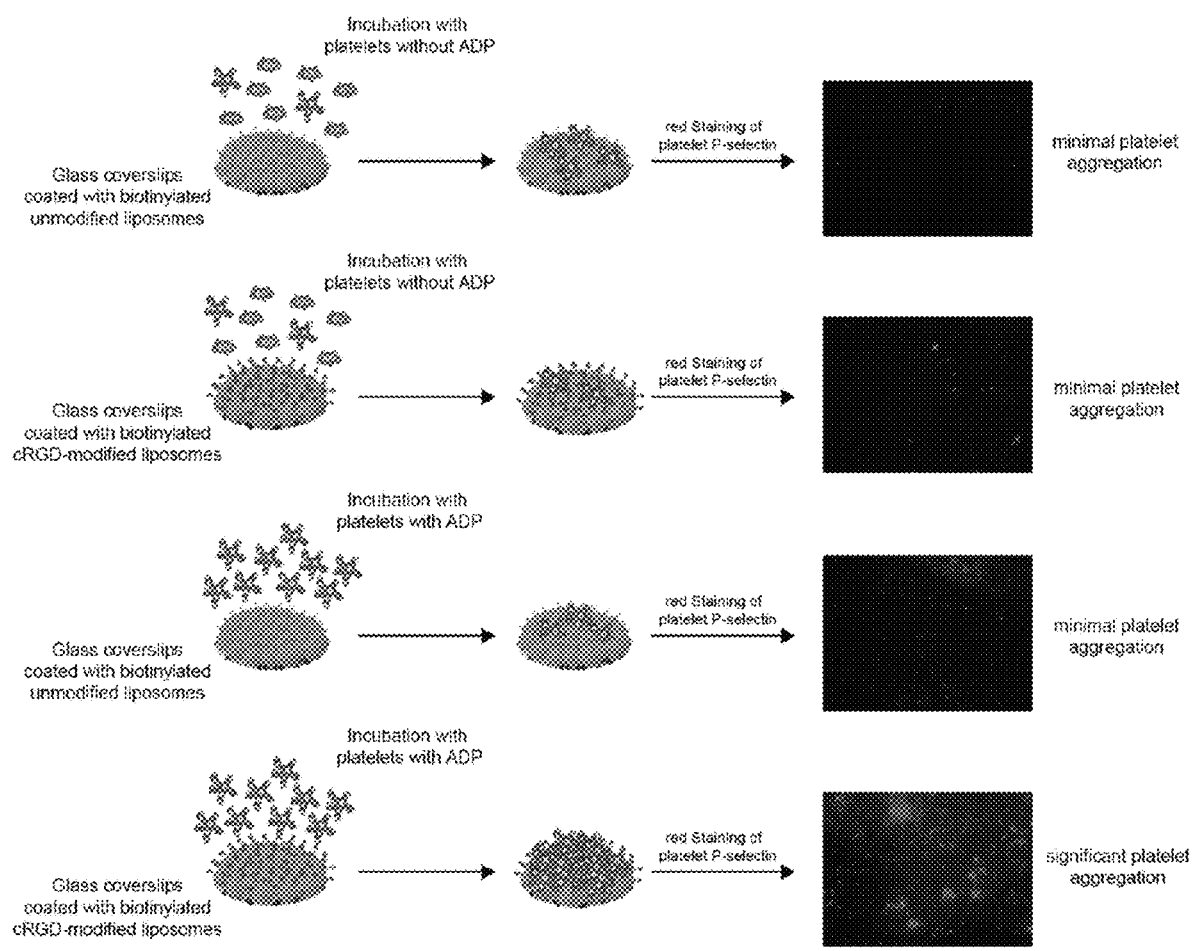
FIG. 8 is a schematic representation and representative fluorescent images from studies of platelet aggregation in absence or presence of ADP on unmodified versus cRGD-modified biotinylated liposomes pre-adhered as monolayer on avidin-coated coverslips. Only cRGD-modified liposomes show enhanced arrest and aggregation of platelets (red fluorescence) onto them in presence of ADP-induced activation. For imaging, platelets were stained with P-selectin specific AlexaFluor 647-anti-CD62P antibody and imaged using a Zeiss Axio Observer.D1 inverted fluorescence microscope fitted with a photometrics chilled CCD camera and a 63× objective.
Figure 10:
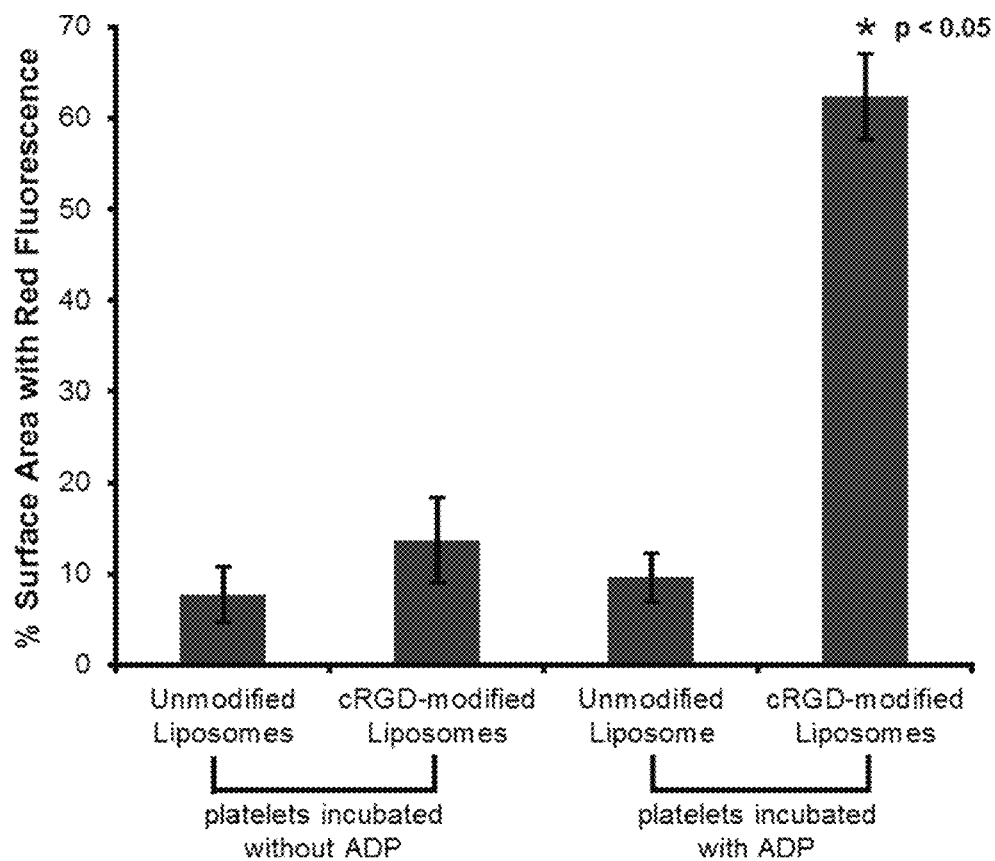
FIG. 10 illustrates quantitative analysis of platelet aggregation on avidin-coated coverslip-attached cRGD-modified versus unmodified biotinylated liposomal constructs, in absence or presence of ADP. cRGD-modified liposomes promote significant aggregation of ADP-activated platelets compared to the other conditions.

Results
Platelet Aggregation on Biotinylated cRGD-Modified Liposomes Coated on Avidin Surfaces The last column in FIG. 8 shows representative fluorescence images for platelet interaction with the coverslip-coated various liposome formulations in absence or presence of ADP-induced platelet activation. FIG. 10 shows the corresponding quantitative data from these studies. The images and the data indicate that in absence of ADP-induced activation, quiescent platelets hardly undergo any interaction with the liposome layer, irrespective of whether the liposomes were unmodified or cRGD-modified. This also suggests that the liposomes themselves, whether unmodified or cRGD-modified, do not themselves activate (and hence aggregate) quiescent platelets. In contrast, upon ADP-induced activation, platelets undergo significantly enhanced interaction with the cRGD-modified liposomes coated on the coverslip surface, resulting in high extent of platelet aggregation. The unmodified liposomes, in comparison, show only minimal aggregation of activated platelets onto them. This establishes that the cRGD-modified liposomal constructs adhered onto a surface are capable of promoting recruitment and aggregation of activated platelets onto them.

Figure 11:
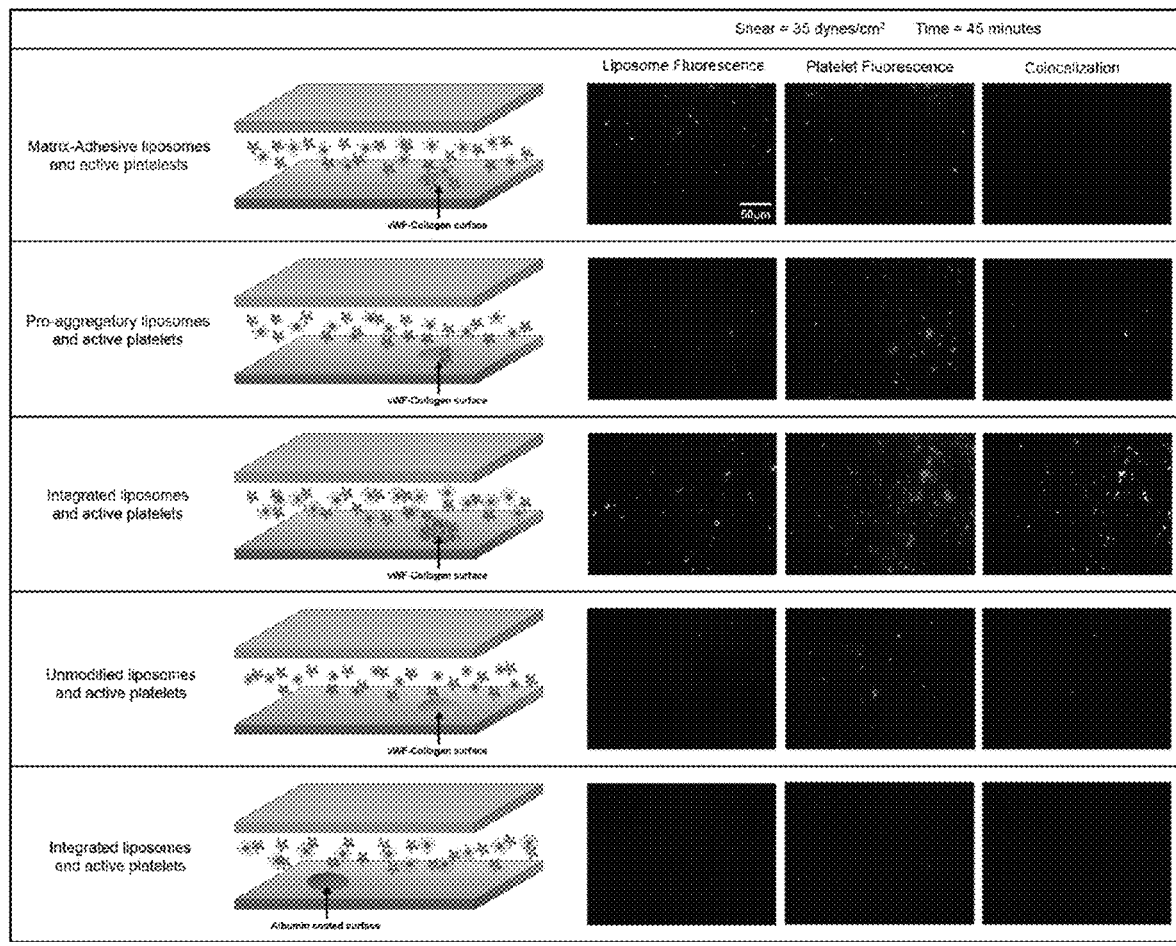
FIG. 11 illustrates experimental conditions and resultant representative fluorescence images of unmodified and various peptide-modified liposomal constructs with low concentrations of activated platelets under flow on albumin-coated and vWF/collagen-coated surface in the PPFC. Green fluorescence (from DSPE-PEG-Fluorescein) represents liposomal constructs adhered onto vWF/collagen, red fluorescence (from AlexaFluor647-anti-CD62P) represents activated platelets aggregated in the same field of view as the liposome adhesion images, and the yellow overlay represents co-localization of the green and red fluorescence signifying adhered liposome promoted aggregation of active platelets. Only images at the 45 minute time point for shear stress value of 35 dynes/cm² are shown here for convenience.
Figure 12:
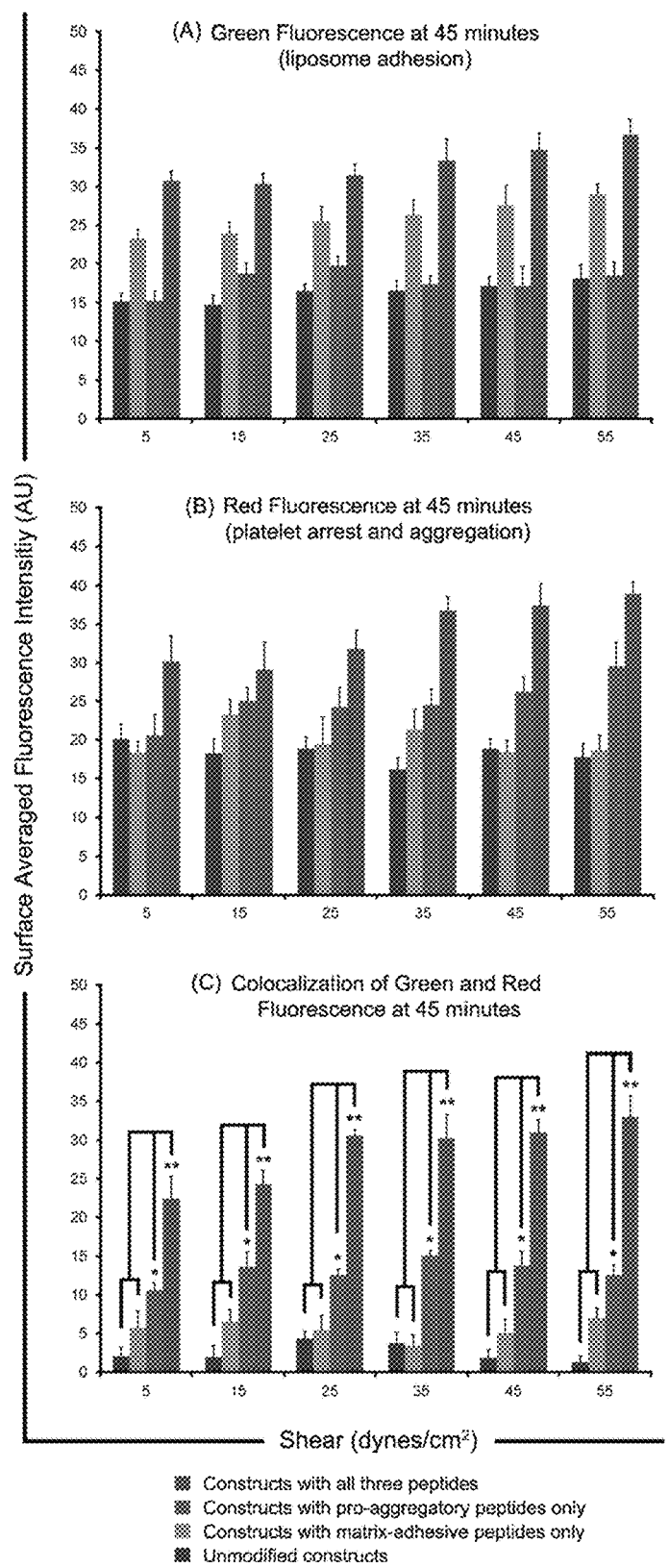
FIG. 12 illustrates a quantitative analysis of the fluorescence data of liposome adhesion, platelet aggregation, and co-localization, from PPFC experiments with unmodified and various peptide-modified liposomal constructs with low concentrations of activated platelets under flow on vWF-collagen surface. The data is shown for wall shear stress values of 5-55 dynes/cm² at the 45 minute time point. The results demonstrate that the functionally integrated liposomes (surface-modified simultaneously by VBP, CBP and RGD) have significantly enhanced capacity to adhere to the vWF/collagen surface under flow at the various shear stress values and promote significant arrest and aggregation of active platelets from flow onto themselves.

Evaluation of Functionally Integrated Liposomal Constructs in Promoting Arrest and Aggregation of Platelets on vWF/Collagen Surface Under Flow FIG. 11 shows representative set of fluorescence images and FIG. 12 shows the quantitative data from the PPFC studies evaluating the various liposomal constructs interacting with activated platelets while flowing over vWF/collagen-coated or albumin-coated surface in the PPFC set-up. In the images, the green fluorescence represents adhered liposomal constructs, the red fluorescence represents arrested and aggregated active platelets, and the yellow pseudocolor represents co-localization of the green liposomes and red fluorescent platelets in the same field of view on the vWF/collagen surface. As evident from the images in the fifth row of FIG. 11, the albumin surface hardly showed any adhesion of liposomes or arrest of platelets, and consequently the quantitative values of liposome or platelet fluorescence (and colocalization) from the albumin surfaces are not included in the quantitative data in FIG. 12. Although images were taken at six shear values between 5-55 dynes/cm$^2$ and at four time points between (5, 15, 30 and 45 min), representative fluorescent images are only shown at one shear value (35 dynes/cm$^2$) and one final time point (45 min) for convenience. The quantitative data in FIG. 12 is shown for this 45 min time point across all shear stress values studied.

From the images in FIG. 11 it is evident that liposomes bearing only aggregation promoting cRGD peptides are unable to undergo significant adhesion to the vWF/collagen surface and promote aggregation of activated platelets from the LPC condition onto them, even if they may cluster some active platelets in flow. This is suggested by the minimal green fluorescence and minimal yellow co-localization shown in the second row of images. The red fluorescence shown in this row indicates a certain extent of platelet arrest and aggregation and this is possibly due to the direct interaction of active platelets with the vWF/collagen surface and not mediated by liposomes. On the other hand, constructs bearing only adhesion promoting peptides (VBP and CBP) but no cRGD, can adhere stably to vWF/collagen surface under flow, but are unable to promote significant arrest and aggregation of activated platelets onto them from the flowing LPC suspension. This is suggested by the presence of considerable green fluorescence but minimal yellow co-localization in the first row of images. As before, the red fluorescence shown in this row does indicate a certain extent of platelet arrest and aggregation due to the direct interaction of active platelets with the vWF/collagen surface and not mediated by liposomes. Unmodified liposomes (no peptide modification) show insignificant adhesion to vWF/collagen surface (minimal green fluorescence) and consequently does not promote any arrest and aggregation of active platelets (minimal yellow fluorescence), as shown in the fourth row of images. As before, some platelet fluorescence (red) is seen here on the vWF/collagen surface due to direct interaction and arrest of active platelets on this surface. In contrast to these, functionally integrated liposomal constructs bearing all three peptides (VBP, CBP and cRGD) show high extent of green fluorescence, as well as, red fluorescence, with significant yellow overlay suggesting co-localization of the green fluorescent liposomes and the red fluorescent platelets on the vWF/collagen surface (third row of images in FIG. 11). This indicates the enhanced ability of these functionally integrated constructs to undergo stable adhesion to the vWF/collagen surface under flow and promote arrest and aggregation of activated platelets onto them, mimicking the primary hemostatic action of natural platelets.

The qualitative results indicated by the fluorescence images are further validated by the quantitative data analysis for liposome fluorescence, platelet fluorescence and co-localized fluorescence intensity shown in separate graphs in FIG. 12. From the graphs it is evident that the functionally integrated liposomes have significantly enhanced ability to adhere to the vWF/collagen surface and promote arrest and aggregation of activated platelets onto them (blue bars in the co-localization graph), compared to unmodified, pro-aggregatory or matrix-adhesive liposomes. The pro-aggregatory liposomes (modified by cRGD only) seemed to cause statistically higher aggregation compared to the unmodified and the matrix-adhesive liposomes (green bars compared to the brown and red bars in the co-localization graph), but this is probably an effect of the cRGD-modified liposomes causing clustering of active platelets in free flow and some of the heavier clusters migrating down and sticking to the vWF/collagen surface. However, this effect of pro-aggregatory liposomes is still statistically lower than the action of the functionally integrated liposomal constructs. These results establish that combining the platelet-mimetic key hemostatic functionalities of adhesion-promotion and aggregation-promotion on a single particle platform can lead to a more refined design of a synthetic hemostat.

In the native mechanism of platelet-mediated primary hemostasis in vascular injury, initially platelets adhere to injury site vWF via interaction between GPIbα of platelet surface receptor complex GPIb-IX-V. This adhesion is enhanced with increasing shear as vWF can multimerize under high shear, allowing larger extent of GPIbα interaction. The GPIba-vWF interaction is supplemented by additional binding interaction of platelet surface receptors GPVI and GPIa/IIa to fibrillar collagen that secures the 'rolling' vWF-adhered platelets and arrests them at the injury site. In our design these two mechanisms of platelet adhesion is mimicked by decoration of multiple copies of VBP and CBP on the liposome surface. Furthermore, in natural hemostasis, the arrested adhered platelets get activated and act as nucleation points for recruitment and aggregation of more active platelets via interaction between native ligand fibrinogen with the surface integrin GPIIb-IIIa on active platelets. In our design, to mimic and amplify this process the liposome surface was decorated by multiple copies of fibrinogen-mimetic cRGD peptides, which have high affinity and selectivity to active platelet GPIIb-IIIa. The results from in vitro PPFC studies with 'functionally integrated' liposomal constructs establish successful platelet-mimicry of our design. Although in our experiments the various peptides were presented on a liposome surface, they can be potentially conjugated to any other particle platform if needed. Also, in the experiments reported here, the total mol % of peptides on the liposome surface was kept at 5 mol % while maintaining the VBP:CBP:cRGD ratio at 1:1:2. This is an initial metric of peptide decoration composition to demonstrate the feasibility of our platelet-mimetic design approach.

Example 3

In this Example, we further describe a 'synthetic platelet' technology (SynthoPlate), whose design is based on mimicking platelets' primary hemostasis mechanisms of injury site-specific adhesion (to collagen and von Willebrand factor [VWF]) and aggregation (via fibrinogen [Fg]-mediated bridging of integrin glycoprotein [GP] IIb-IIIa on activated platelets). Integration of these platelet-mimetic dual functionalities was achieved via heteromultivalent surface decoration of biocompatible lipid vesicles with VWF-binding peptide (VBP), collagenbinding peptide (CBP), and active GPIIb-IIIa-binding Fg-mimetic peptide (FMP) (FIG. 13). We have previously shown that this integrative design results in superior hemostatic performance than 'adhesion-only' and 'aggregation-only' designs. Also, in platelets' hemostatic action, colocalization of coagulation factors on the surfaces of activated procoagulant platelets at the bleeding site results in amplification of thrombin and fibrin generation (secondary hemostasis). Thus, we hypothesized that SynthoPlate-mediated direct enhancement of platelet recruitment and aggregation at an injury site would, in effect, also enhance secondary hemostatic output at that site. Therefore, we focused here on characterizing the capabilities of SynthoPlate vesicles regarding primary and secondary hemostatic mechanisms in vitro, and subsequently evaluated the systemic safety and hemostatic efficacy of SynthoPlate in vivo in a mouse model of thrombocytopenia.

Materials and Methods

Materials 1,2-Distearoyl-sn-glycero-3-phosphocholine (DSPC), carboxypoly(ethylene glycol)-modified 1,2-Distearoyl-sn-glycero-3-phosphoethanolamine (DSPE-PEG2000-COOH) and Rhodamine B (RhB)-dihexadecanoyl-sn-glycero-3-phosphoethanolamine (DHPE-RhB) were from Avanti Polar Lipids (Alabaster, Ala., USA). The peptides TRYL-RIHPQSWVHQI (VBP), [GPO]7 (CBP) and cyclo-CN-PRGDY(OEt)RC (FMP) were custom-synthesized by Genscript (Piscataway, N.J., USA), conjugated to DSPE-PEG2000-COOH, and characterized by mass spectrometry. Phosphate-buffered saline (PBS), bovine serum albumin (BSA), sodium bicarbonate and fluorescent human Fg (Alexa Flu- or -647-labeled) were from Thermo Fisher (Waltham, Mass., USA). Cholesterol and rat tail type I collagen were from Sigma-Aldrich (Saint Louis, Mo., USA), ADP was from Bio/Data Corporation (Horsham, Pa., USA) and human VWF (FXIII-free) was from Hematologic Technologies (Essex Junction, Vt., USA). Citrated human whole blood was obtained from freshly donated stock from healthy donors at Case School of Medicine. The parallel-plate flow chamber (PPFC) system was from Glycotech (Gaithersburg, MD, USA). For mouse studies, MOPC-21, anti-CD41 and anti-CD42 antibodies were from Abcam (Cambridge, Mass., USA). For immunostaining, rat anti-mouse CD41 antibodies were from Bio-Rad (Hercules, Calif., USA), fluorescein isothiocyanate (FITC)-labeled don-key-anti-rat IgG was from Thermo Fisher, rat anti-mouse CD31 was from Biolegend (San Diego, Calif., USA) and goat anti-rat Alexa Fluor-633-IgG was from Thermo Fisher. For immunoblot studies, lysis buffer (RIPA) was from Sigma-Aldrich, protease inhibitors were from Roche Applied Science (Madison, Wis., USA), phosphatase inhibi-tors and aprotinin were from Sigma-Aldrich, corn trypsin inhibitor was from Hematologic Technologies, the Protein DC assay was from Bio-Rad, rabbit polyclonal Fg/fibrin antibody was from Life Span Biosciences (Seattle, Wash., USA), horseradish peroxidase (HRP)-conjugated secondary antibody was from Cell Signaling (Danvers, Mass., USA), super signal west Pico chemiluminiscent substrate was from Thermo Fisher, and antibodies against b-actin were from Santa Cruz Biotechnology (Santa Cruz, Calif., USA). All in vivo studies were carried out as per approved Institutional Animal Care and Use Committee protocols at Cleveland Clinic and the University of Pittsburgh.

Manufacture of SynthoPlate

Figure 13A:
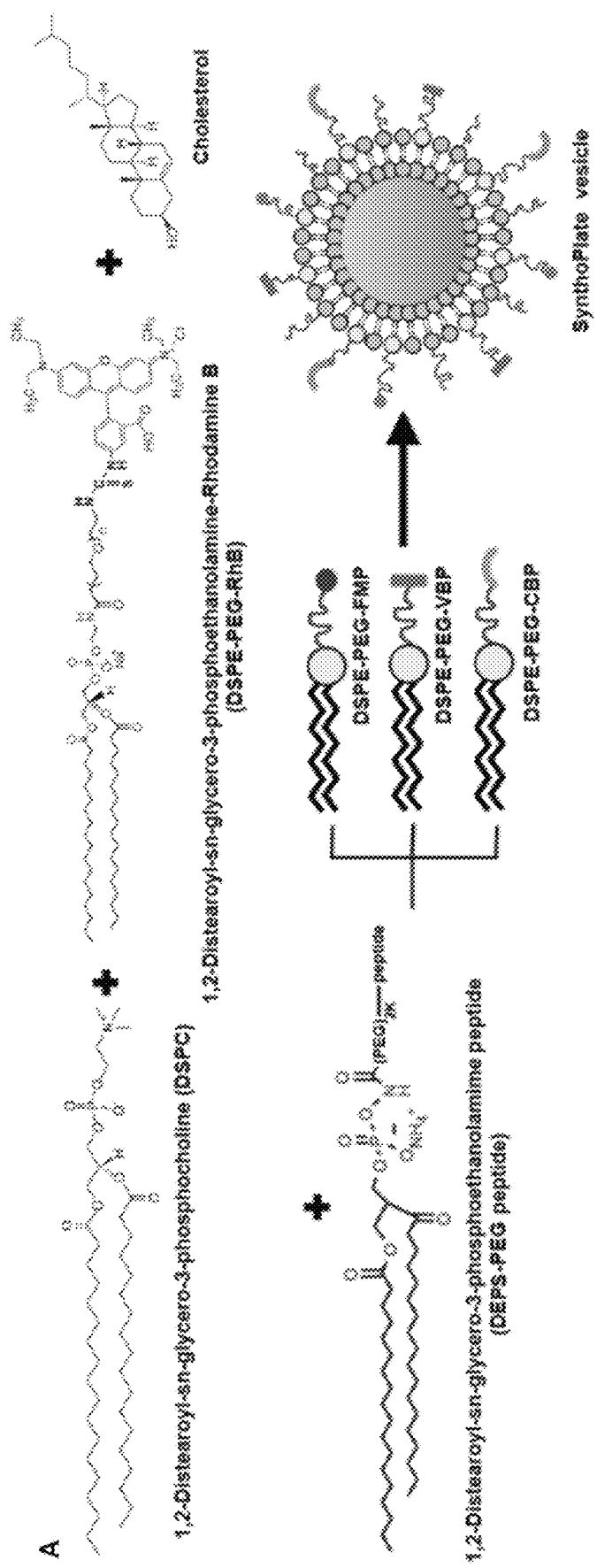
FIGS. 13(A-D) illustrate manufacture and characterization of SynthoPlate constructs. (A) Schematic representation of SynthoPlate manufacture, in which DSPC, DSPE-PEG peptides (DSPE-PEG-VBP, DSPE-PEG-CBP, and DSPE-PEG-FMP), cholesterol and lipid-Rhodamine B (RhB) were selfassembled at controlled concentrations with a reverse-phase evaporation and extrusion technique to form hetero-multivalently peptide-decorated vesicles. (B-D) Dynamic light scattering (B), scanning electron microscopy (C) and cryo-transmission electron microscopy (D) characterization of the SynthoPlate vesicles shows a narrow size distribution, with an average diameter of ~150 nm. Scale bars in (B) and (C): 200 nm. CBP, collagen-binding peptide; FMP), fibrinogen-mimetic peptide; VBP, von Willebrand factor-binding peptide.
Figure 13B:
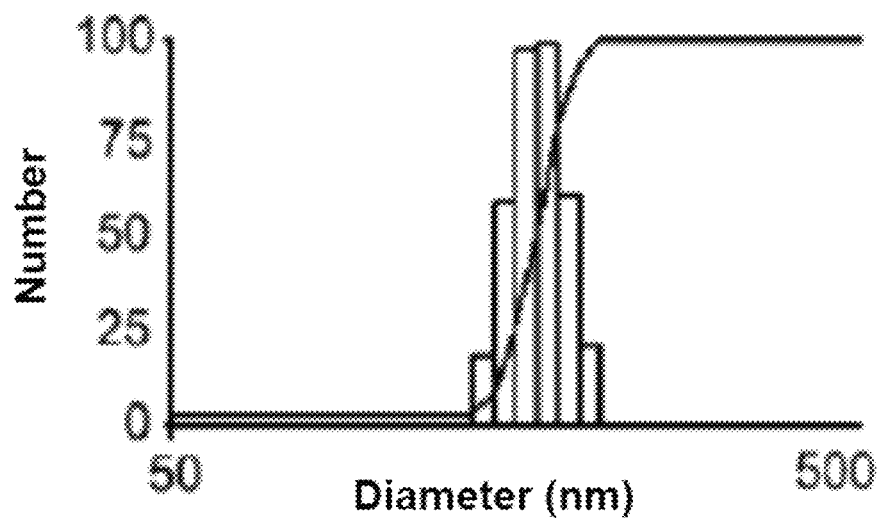
Figure 13C:
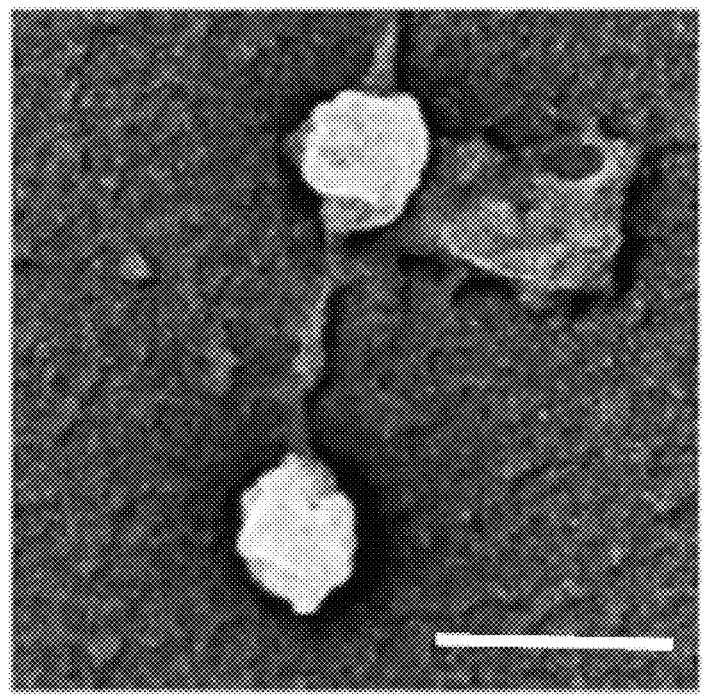

The SynthoPlate design utilizes a clinically relevant poly (ethylene glycol)-modified lipid vesicle platform, refined by heteromultivalent ligand decoration. For this, DSPC, cholesterol, DSPE-PEG-VBP, DSPE-PEG-CBP and DSPE-PEG-FMP were homogenously mixed at mole fractions of 0.50, 0.45, 0.0125, 0.0125 and 0.025, respectively, in 1:1 methanol/chloroform, and this lipid mixture was subjected to reverse-phase evaporation, PBS-based hydration, and subsequent extrusion through a 200-nm-pore membrane (Northern Lipids, Burnaby, BC, Canada) to yield heteromultivalently surface-decorated SynthoPlate vesicles (a schematic is shown in FIG. 13A). Dynamic light scattering, scanning electron microscopy and cryo-transmission electron microscopy characterization indicated vesicles ~150 nm in diameter (FIGS. 13B-D). On the basis of these parameters, the theoretical ligand density per vesicle is ~50,000. By use of a Malvern zetasizer, the zeta potential of SynthoPlate was found to be −24.9±8.00 mV, and that for control (unmodified) particles was found to be −25.2±9.77 mV.

In Vitro Studies of the SynthoPlate Effect on Platelet Aggregation

Turbidimetric experiments were carried out on platelet-rich plasma (PRP) with ADP as agonist, or on washed platelets (Plts) with collagen as agonist, by use of a Chrono-log Aggregometer (Chrono-log, Havertown, Pa., USA), to test the interaction of SynthoPlate with active versus resting platelets. Wild-type C57Bl-6 mice were anesthetized, and whole blood was drawn by venipuncture with 0.109 M sodium citrate. Modified Tyrode's buffer (0.7 v/v) was added, and PRP was separated by centrifugation (150×g, 20 min). The platelet concentration in PRP was adjusted to $2.50 \times 10^8$ mL$^{-1}$ with platelet-poor plasma (PPP). To prepare washed platelets, PRP was further centrifuged at 650×g for 6 min in the presence of 0.5 μM prostaglandin $E_1$(PGE1). The resultant platelet pellet was resuspended in PBS containing 0.109 M sodium citrate (9:1, v/v) and 0.5 μM PGE1, repelleted, and resuspended in PBS to a concentration of $2.50 \times 10^8$ mL$^{-1}$. Aggregometry studies were conducted at 37° C. with stirring at 1200 r.p.m. ADP-mediated aggregation was performed with 400 μL of PRP (labeled as 100% PRP in FIG. 14A), or PRP diluted 50% (v/v) with either PPP (50% PRP in FIG. 14A) or PPP containing SynthoPlate or PPP containing control particles with a particle concentration of $5.00 \times 10^{10}$ mL$^{-1}$. To further ensure that the effect of SynthoPlate (or control particles) was specifically on platelets, collagen-based aggregation studies were performed with washed platelets instead of PRP (labeled as 100% Plts or 50% Plts in FIG. 14B), and here particles were suspended in PBS instead of PPP. Aggregation was monitored with the addition of a final concentration of 1 mM $Ca^{2+}/Mg^{2+}$ and with or without the addition of platelet agonists (ADP at 2.5 µM and collagen at 1 µg mL-1). The 50% dilution of platelets was considered to be a thrombocytopenic (TCP) condition, as rationalized from the clinical definition. The same SynthoPlate and control particles were also used to characterize the particle-mediated recruitment and aggregation of active platelets on 'VWF+collagen'-coated surfaces under flow in the PPFC, imaged under fluorescence microscopy. For this, calcein-stained (green fluorescent) platelets suspended in plasma (50 000 $mL^{-1}$) were passed over 'VWF+collagen'-coated surfaces along with RhB-labeled (red fluorescence) SynthoPlate (or control) particles, ADP (2.5 µM), and soluble VWF (10 µg $mL^{-1}$), with an adaptation of previously published methodology. The flow was maintained at shear stress of 50 dyn $cm^{-2}$ (shear rate of >3000 $s^{-1}$, assuming plasma to be a Newtonian fluid with a constant viscosity of Synthoplate™ evaluation in thrombocytopenia 3 0.015 P) to ensure a hemostatically relevant interaction of VWF with collagen. The colocalization of active platelets and particles (red) on the surfaces was imaged with a Zeiss inverted fluorescence microscope (Thornwood, N.Y., USA).

In Vitro Studies of SynthoPlate Effects on Thrombin and Fibrin Generation

Experiments were carried out to first study whether SynthoPlate vesicles themselves spontaneously generate thrombin in human plasma (i.e., assessing systemic coagulation risk). PRP was obtained from freshly drawn citrated human whole blood by centrifugation (150×g, 15 min), and PPP was obtained by further centrifugation of PRP (2500×g, 20 min). The thrombin-cleavable fluorogenic substrate (p-tosyl-Gly-Pro-Arg)$_2$-Rhodamine-110 (Thermo Fisher) at a final concentration of 0.1 mM (in Tris buffer, pH 7.4, 22° C.) was incubated in the presence of 5% v/v 0.5 M $CaCl_2$ with the groups: 'PPP only', 'PRP only', 'PPP+SynthoPlate', 'PRP+SynthoPlate', 'PPP+tissue factor', 'PRP+tissue factor', 'PRP+SynthoPlate+tissue factor', 'PRP+ADP+tissue factor', and 'PRP+ADP+SynthoPlate+tissue factor'. The particle concentration, in the applicable groups, was 5.00 91010 $mL^{-1}$. The resultant thrombin activity was monitored with a Bio-Tek (Winooski, Vt., USA) plate reader (excitation/emission at 498/521 nm) for 40 min. Next, for fibrin generation/deposition studies, the PPFC set-up was used as before, with some modifications. Glass slides precoated with 'collagen+VWF' or BSA were sealed within the PPFC, and exposed to flow of fresh 100% PRP (platelet count of 250 000 $µL^{-1}$), or 50% PRP (platelet count diluted 50% with PPP to 125 000 $L^{-1}$), or 100% PPP and SynthoPlate (or control) particles, in the presence of fluorescent Fg (Alexa Fluor-647-Fg at 1.5 mg $mL^{-1}$ added at 3% v/v), with or without ADP. The 'control' particles had only proadhesive peptides (VBP and CBP only; no FMP) such that they can still bind to the 'VWF+collagen' substrate but cannot recruit and aggregate active platelets. The flow was maintained at 50 dyn $cm^{-2}$ for 15 min. In this set-up, SynthoPlatemediated recruitment and aggregation of active platelets on the 'VWF+collagen' surface was hypothesized to augment the availability of procoagulant active platelet membrane for facilitating secondary hemostatic mechanisms, leading to amplified generation and deposition of fibrin(ogen) during the 15-min time-window. This deposition was imaged with inverted fluorescence microscopy (emission, 665 nm). At 15 min, the flow was stopped, and the clots on the slides were incubated with streptokinase in PPP (20 µL per mL of PPP) for 60 min. The resultant lysed clots were analyzed with a fibrin D-dimer-specific spectrophotometric ELISA assay (Thermo Fisher) according to the manufacturer's instructions, and D-dimer levels were calculated from a standard calibration curve. The D-dimer analysis was to confirm that the clot fluorescence observed was indeed from fibrin generation and not just Fg.

Effects of SynthoPlate in Severely TCP Mice

Figure 16A:
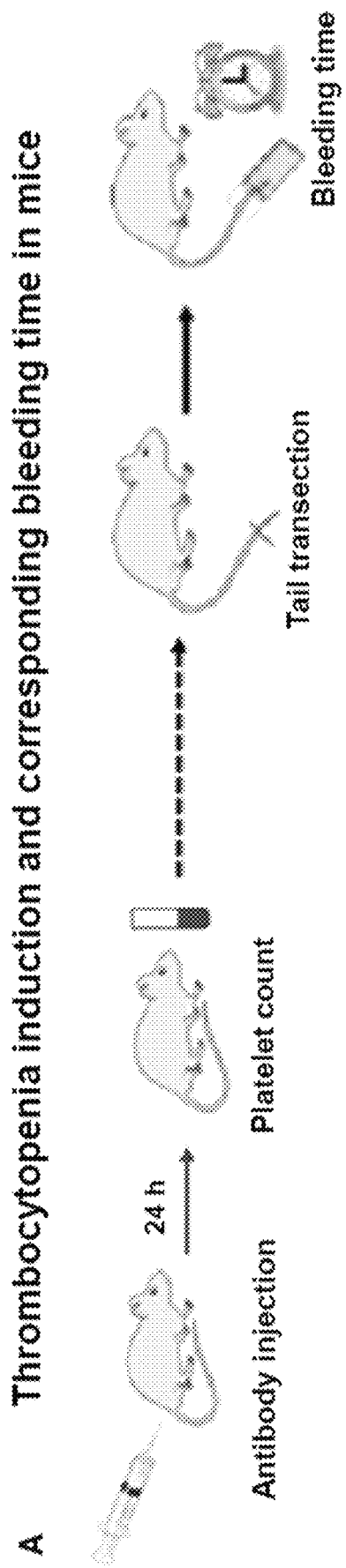
FIGS. 16(A-B) illustrate the development of thrombocytopenia model in mouse and evaluation of SynthoPlate capability in correcting tail transection bleeding time in thrombocytopenic mouse. (A) Experimental design for antibody-induced thrombocytopenia in mice and subsequent tail-bleeding studies, in which (A1) dose-dependent depletion of platelets resulted in (A2) a corresponding increase in bleeding time after tail transection (10 µg of antibody cocktail dose resulted in ~90% platelet depletion and a corresponding four-fold to five-fold increase in bleeding time as compared with normal mice). (B) Severely thrombocytopenic (TCP) mice injected with phosphate-buffered saline (PBS) or control (unmodified) particles at various doses show no improvement (reduction) in bleeding time, but TCP mice injected with SynthoPlate vesicles show a dose-dependent significant improvement in bleeding time, with the highest dose (1000 nL$^{-1}$, equivalent to the normal murine platelet count) reducing the bleeding time to ~150 s (close to the bleeding time of ~100 s for normal mice, shown for comparison); *P≤0.05, P≤0.01, and *P≤0.001. NS, not significant.

We adapted a model of passive immune thrombocytopenia in mice with platelet-specific antibodies. Wild-type C57/BL6 mice were injected intraperitoneally with a combination of anti-CD41 and anti-CD42 antibodies (1:1 ratio at 1-10 µg total) and, 24 h later, platelet counts were performed with an Advia 120 Hematology analyzer (Erlangen, Germany) (six mice per group). For bleeding time assessment, 24 h after administration of 10 µg of antibody, tails of TCP mice were transected 2 mm from the tip with a surgical blade, and immersed in 37° C. saline; the time needed for bleeding to stop was recorded (a schematic is shown in FIG. 16A). Next, similarly treated TCP mice were injected with 150 µL of various doses (100, 500 or 1000 $nL^{-1}$) of SynthoPlate or control (unmodified) particles via the jugular vein and, 2 h after particle injection, the mouse tails were transected as before to record the bleeding time. The 2-h-circulation time-period was chosen as a feasibility metric for evaluating the 'prophylactic window' of the SynthoPlate technology, and future studies will focus on expanding this window to longer circulation lifetimes. All tail-bleeding studies were performed in accordance with standardization parameters highlighted by the ISTH. After bleeding time studies, mice were killed, and 4-5-mm tail-pieces proximal to the transection site were cut, washed in PBS, fixed in paraformaldehyde for 24 h, and then cryoprotected in 30-60% sucrose and flash frozen in OCT compound (Tissue Tek, Torrance, Calif., USA). Cryoblocks were prepared in cryo-molds (Electron Microscopy Sciences, Hatfield, Pa., USA) over dry ice and 2-methylbutane, and 9-lm-thick sections were cut with a Leica CM1950 cryostat (Buffalo Grove, Ill., USA) and collected on superfrost glass slides (Thermo Fisher) for staining. For immunostaining, frozen sections were air-dried, rinsed in PBS, and blocked with 0.1% Tween-20 and 1% BSA. A sequential staining protocol was followed, in which sections were first incubated with rat anti-mouse CD41 antibodies overnight at 4° C., and then washed in PBS and incubated with an FITC-labeled donkey-anti-rat IgG for 2 h. After additional washes, sections were incubated with rat anti-mouse CD31 for 2 h, and then washed and labeled with goat anti-rat Alexa Fluor-633-IgG. Slides were mounted with Vectashield, and imaged under a Leica fluorescence microscope. In additional experiments, similar tail sections from TCP mice treated with SynthoPlate or control particles were collected directly into lysis buffer containing protease inhibitors, phosphatase inhibitors, corn trypsin inhibitor, and aprotinin. Tails were disrupted by sonication, and lysates were clarified by centrifugation at 12,000×g for 15 min at 4° C. The supernatant was collected, and protein was measured with the Protein DC assay. For immunoblotting, tail extracts were mixed with 5×SDS sample buffer containing β-mercaptoethanol, and heated at 95° C. for 5 min. Samples were resolved by 10% SDS-PAGE with 25 µg of protein in each lane, and transferred to poly(vinylidene difluoride) membranes. Membranes were probed overnight at 4° C. with a 1:5000 dilution of rabbit polyclonal Fg/fibrin antibody (Life Span Biosciences). Bound antibody was detected with an HRP-conjugated secondary antibody and super signal west Pico chemiluminescent substrate. The membrane was stripped in stripping buffer containing 15 g L$^{-1}$ glycine, 1 g L$^{-1}$ SDS, and 10 mL L$^{-1}$ Tween-20 (pH 2.2), blocked, and reprobed with antibodies against β-actin.

Assessing the Systemic Safety and Biodistribution of SynthoPlate During 2 h of Circulation For systemic safety analysis, wild-type or TCP mice were intravenously injected with SynthoPlate or control (unmodified) particles and, 2 h after particle injection, blood was collected via cardiac puncture in sodium citrate (0.109 M, 3.2%) and analyzed with an immunoturbidimetric agglutination assay for circulating fibrin D-dimer levels (STA-Liatest D-Di; Diagnostica Stago, Parsippany, N.J., USA), according to the manufacturer's instructions. In parallel experiments, mice were injected intravenously with 8 lg kg$^{-1}$ lipopolysaccharide (LPS) (positive control) or 120 μL of SynthoPlate or control particles (1000 nL$^{-1}$). At 30 min and 2 h after injection, blood was drawn from the facial vein directly into Tubes© 2016 International Society on Thrombosis and Haemostasis Synthoplate™ evaluation in thrombocytopenia 5 containing sodium citrate, corn trypsin inhibitor, and aprotinin, and centrifuged at room temperature for 10 min at 850×g; the plasma was then collected and analyzed with a double-antibody sandwich ELISA for prothrombin fragment 1+2, according to the manufacturer's instructions (Biosource, San Diego, Calif., USA).

For biodistribution studies, mice were injected intravenously with SynthoPlate, and killed after 2 h with overdose of anesthesia cocktail. Various organs were harvested, rinsed in PBS, and freeze-dried to obtain the dry weight The organs were homogenized at 4000 r.p.m. (BeadBug Microtube Homogenizer; Benchmark Scientific, (Edison, N.J., USA), and homogenates were shaken overnight at 750 r.p.m. and 37° C. with 1:1 methanol/chloroform solution to extract the RhB-labeled lipids. The resultant samples were centrifuged at 1000×g for 10 min, the supernatant containing RhB-labeled lipids was collected, and the fluorescence in the supernatant was determined with a Bio-Tek Plate reader (excitation, 550 nm; emission, 590 nm). The SynthoPlate percentage in various organs was determined by calculating the concentration (ng mL$^{-1}$) of particles in the supernatant from a calibration curve. In complementary studies, SynthoPlate particles were radiolabeled either by incorporating 3H-tagged cholesteryl ester in the vesicle membrane, or encapsulating indium chloride ($^{111}$InCl$_3$) in the vesicle core. Following tail-vein injection of these particles, mice were either killed for harvesting of organs and blood for scintillation counting of $^3$H-labeled particles, or wholebody imaged by single photon emission computed tomography for assessment of the $^{111}$InCl$_3$-labeled particle distribution.

Statistical Analysis

Where applicable, data were expressed as mean±standard deviation. Aggregometry results were analyzed by one-way ANOVA with Bonferroni post hoc testing for multiple comparisons by the use of SIGMASTAT 3.5. Thrombin and fibrin assay results were analyzed by one-way ANOVA and Tukey's test. For some in vivo results, analyses were also carried out with a two-tailed Student's t-test. A P-value of <0.05 was considered to be statistically significant.

Results

In Vitro Studies of SynthoPlate-Mediated Primary Hemostasis Mechanisms

Representative aggregometry data for PRP or washed platelets, along with corresponding histograms of percentage aggregation, are shown in FIG. 14. As is evident from FIG. 14A1, without platelet activation, SynthoPlate itself has no aggregatory effect on platelets, as the turbidimetric trace for this (brown) was same as that for resting (without ADP) platelets (indigo). This suggests that SynthoPlate will not activate resting platelets in the circulation. Upon agonist addition, platelet aggregation was observed in 100% PRP as well as in 100% platelets (green traces in FIG. 14A1, B1). This aggregation was significantly reduced when PRP was diluted by 50% v/v with PPP or platelets were diluted with saline (purple traces in FIG. 14A1, B1). This dilution effect was not rescued when control (unmodified) particles were added (red traces in FIG. 14A1, B1). In contrast, addition of SynthoPlate particles significantly rescued the aggregation (cyan traces in FIG. 14A1, 2B1). Statistical analyses (FIG. 14A2, B2) clearly show this ability of SynthoPlate to improve the aggregation of diluted platelets. Also, the SynthoPlate vesicles themselves did not show any aggregation in presence of platelet agonists and Ca$^{2+}$. Fluorescence microscopy studies in PPFC demonstrated that RhB-labeled (red fluorescent) SynthoPlate particles showed significant colocalization (yellow overlay) with calcein-stained (green fluorescent) active platelets on a 'VWF+collagen' surface, whereas unmodified, 'adhesion-only' and 'aggregation-only' particles showed minimal colocalization. These results are in accordance with our previously reported findings. Altogether, these studies indicate that: (i) SynthoPlate interacts specifically with activated platelets to augment their aggregation; and (ii) this aggregation can be enhanced selectively at the site of 'VWF+collagen' exposure (amplification of primary hemostasis) via SynthoPlate action.

In Vitro Studies of SynthoPlate-Mediated Thrombin Generation

Figure 15A:
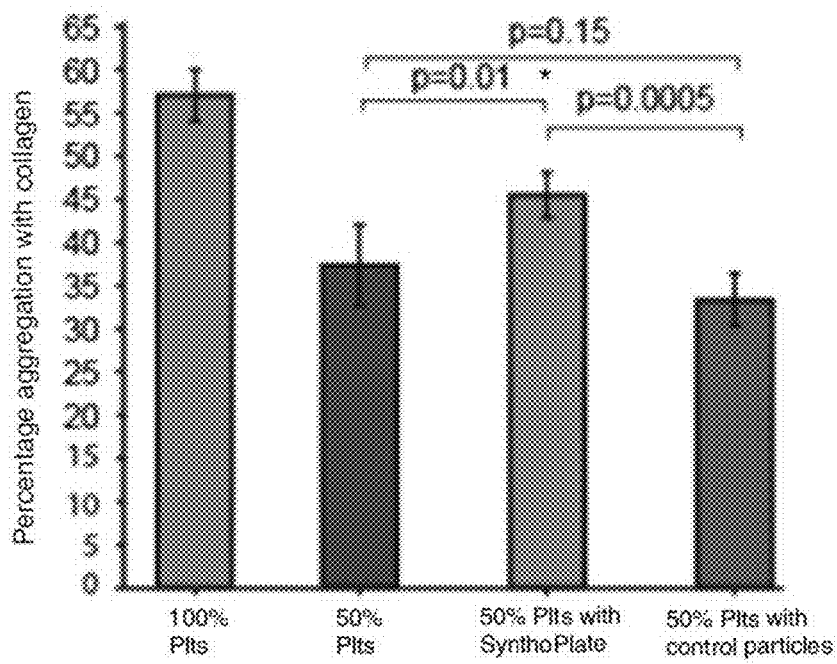
FIGS. 15(A-D) illustrate Effect of SynthoPlate on secondary hemostasis (thrombin generation and fibrin deposition). (A) A table showing the results from thrombin generation assays indicates that SynthoPlate itself does not have the ability to rapidly activate coagulation factors in plasma to generate thrombin, as adding only SynthoPlate to recalcified platelet-rich plasma (PRP) or platelet-poor plasma (PPP) without tissue factor (TF) or platelet agonist (e.g., ADP) has no accelerating effect on thrombin generation, and the thrombin generation is enhanced only upon TF and/or ADP addition to PRP or PPP, with SynthoPlate slightly enhancing this effect (possibly by recruitment and clustering of active platelets in suspension). (B, C) Representative fluorescence images at the 15-min time-point (B) and (C) surface-averaged fluorescence intensity values at the 5-min and 15-min time-points of fibrin(ogen) generation/deposition on 'von Willebrand factor (VWF)+collagen' surface (C) in the parallelplate flow chamber experiments show that resting platelets (without ADP) in 50% PRP (diluted with PPP) generate/deposit only minimal levels of fibrin(ogen) as they interact with the 'VWF+collagen' surface, and that this generation/deposition increases if platelet agonist is introduced into the flow (i.e., with ADP). Introducing SynthoPlate vesicles into the flow along with ADP-activated platelets in 50% PRP significantly enhances fibrin(ogen) generation/deposition during the 15-min flow period, as compared with flow with 'adhesion-only' particles (control) and even as compared with flow of 100% PRP (with ADP) without SynthoPlate. (D) D-dimer analysis of the generated/deposited clots on the 'VWF+collagen' surface confirms that the clots resulting from enhanced clot formation in the SynthoPlate-added group are indeed rich in fibrin, and that the process does not just involve fibrinogen binding to recruited active platelets.
Figure 15B:
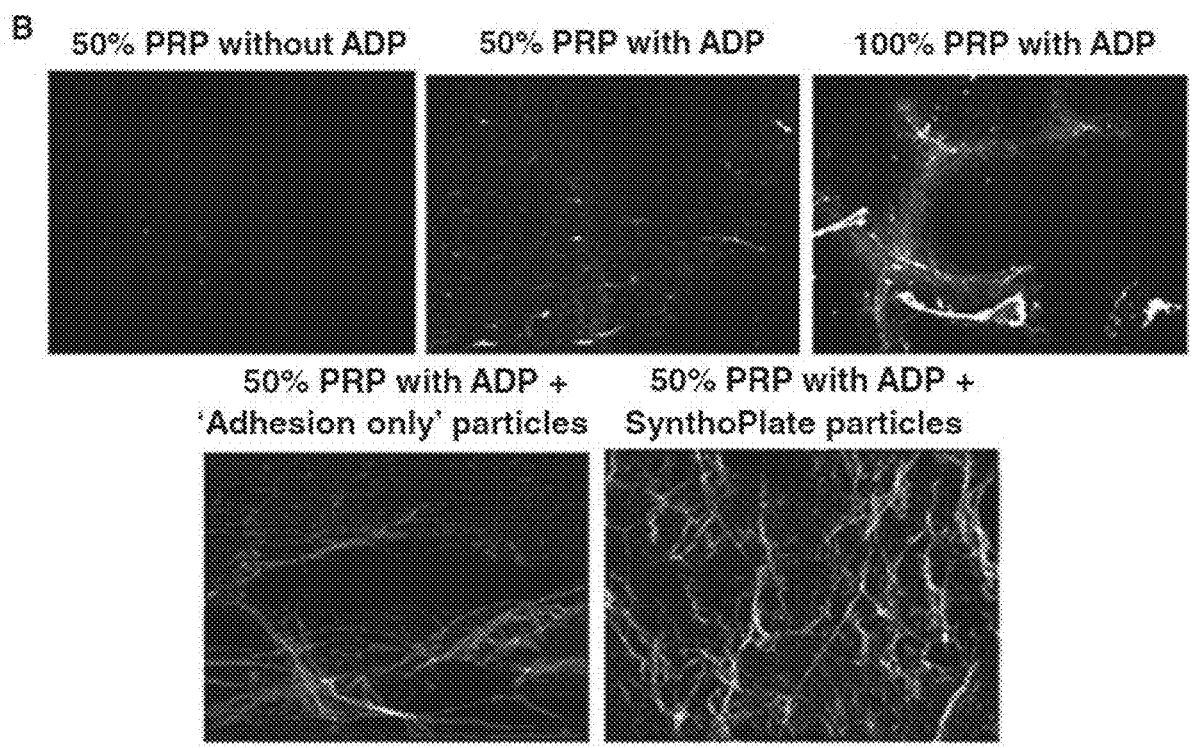
Figure 15C:
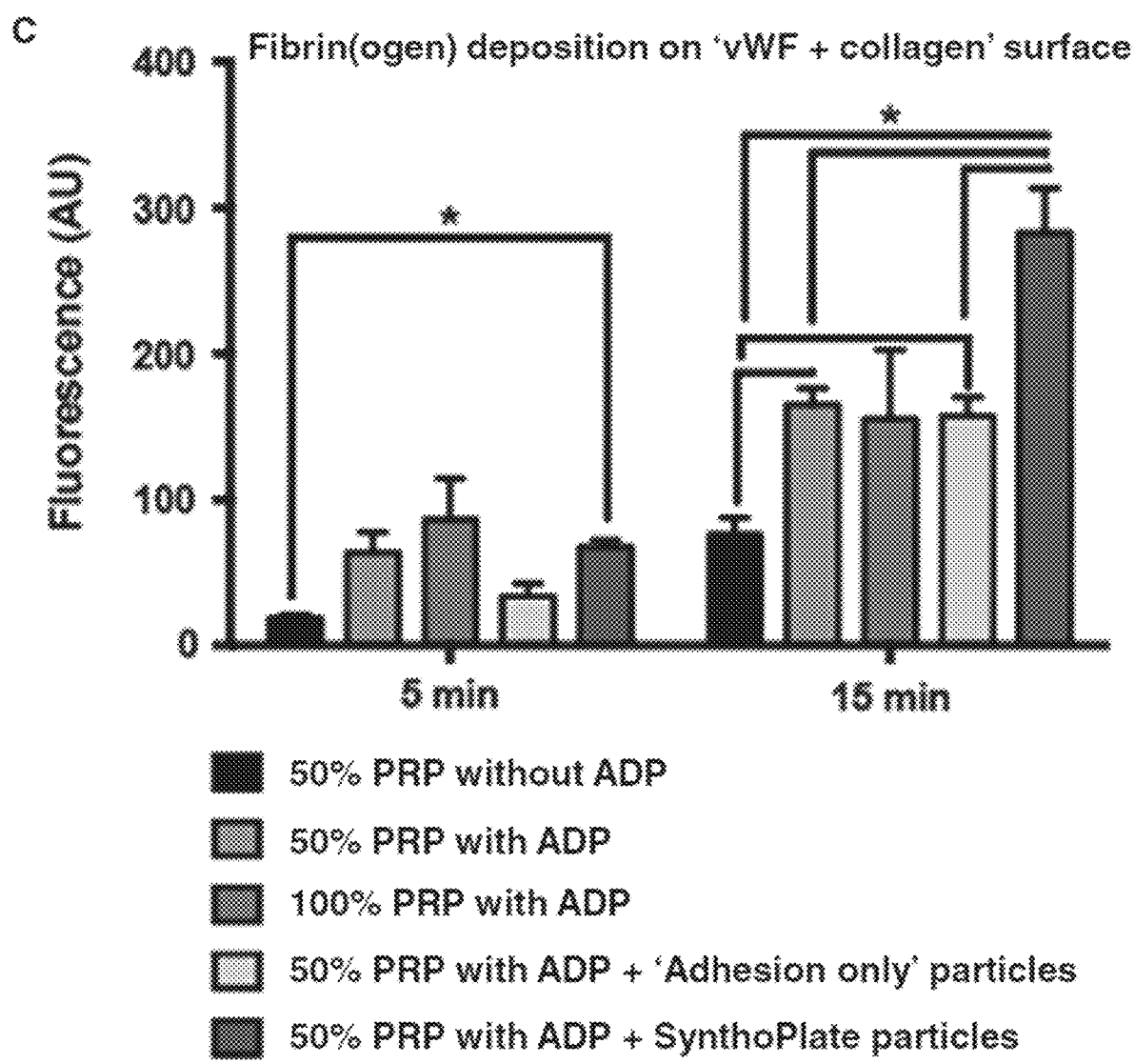
Figure 15D:
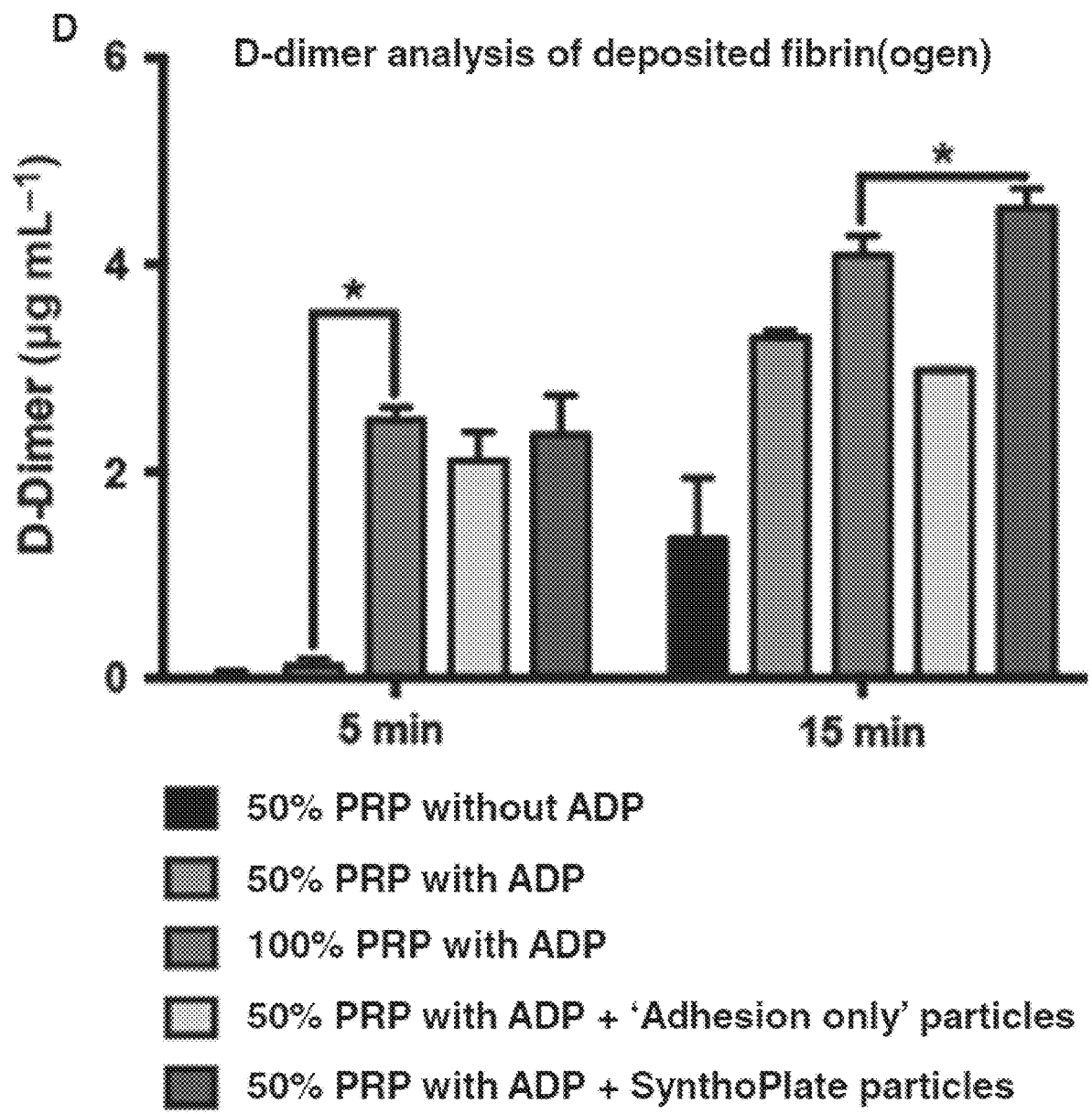

FIG. 15A shows the table for thrombin generation parameters obtained for the various groups studied. As is evident from the results, without tissue factor or platelet agonist (ADP), addition of SynthoPlate to recalcified PRP or PPP did not induce or accelerate rapid thrombin generation, and thrombin generation occurred with a much longer lag time, as is common for recalcified plasma. In the presence of tissue factor and/or ADP, thrombin generation was drastically accelerated in PRP (or PPP) even without SynthoPlate, and the reaction speed increased slightly when SynthoPlate was present. This indicates that SynthoPlate itself does not directly influence thrombin generation in plasma, but can possibly indirectly influence thrombin generation if it can recruit procoagulant active platelets at the site of injury and tissue factor exposure. This possibility was further confirmed by the results of the fibrin(ogen) generation/deposition study under flow (representative images and quantitative results are shown in FIG. 15B,C). In this case, during the 15-min time-window, the fluorescence of deposited fibrin(ogen) significantly increased when ADP-activated 50% PRP was passed with SynthoPlate over a 'VWF+ collagen' surface, as compared with the control conditions. The D-dimer ELISA studies further confirmed that the deposited clot in this group contained a significant amount of fibrin (FIG. 15D). All together, these studies confirm that SynthoPlate does not have any innate ability to stimulate coagulation in plasma (and therefore has a minimum systemic procoagulant risk), but can, 'in effect', augment coagulatory output at the injury site by enhancing the recruitment and aggregation of active platelets at the site.

Figure 2:
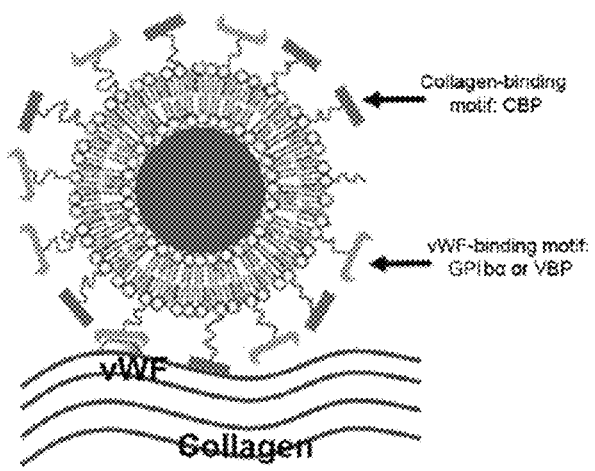
FIG. 2 is a design of heteromultivalent liposomes surface-modified with vWF-binding and collagen-binding ligand motifs that can mimic the adhesion mechanisms of platelets under flow.
Figure 16B:
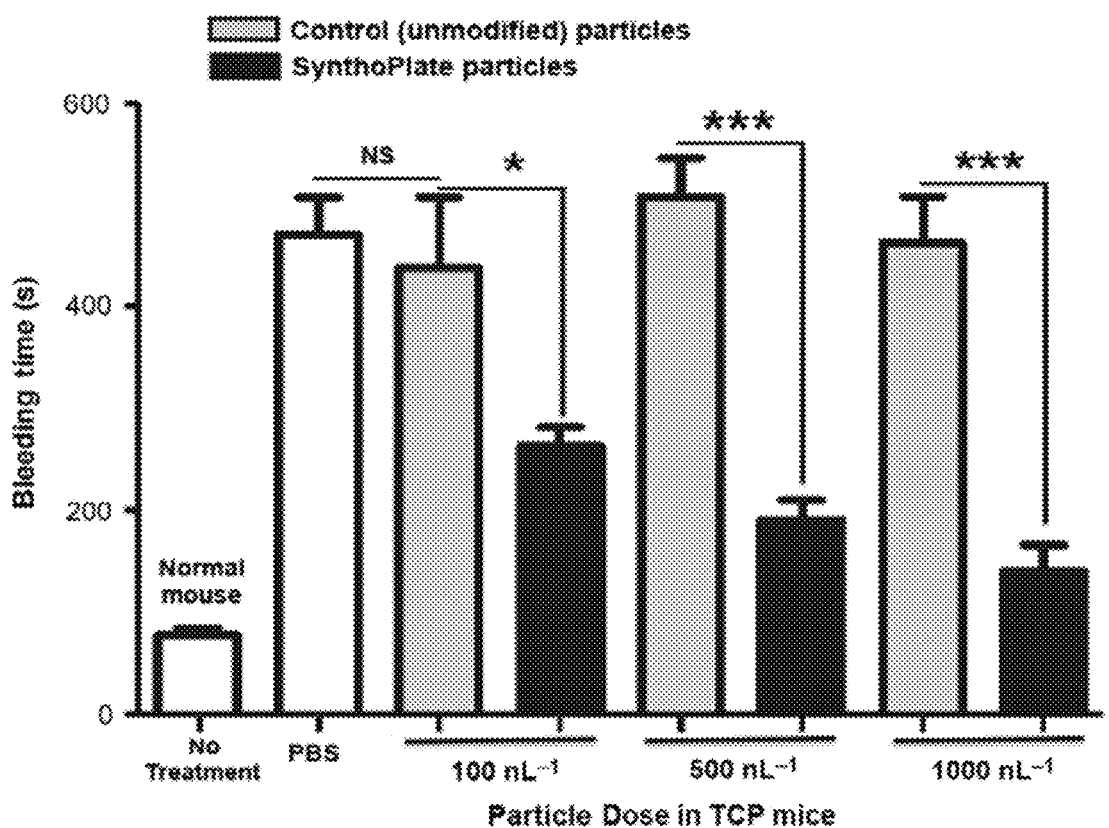
Figure 17A:
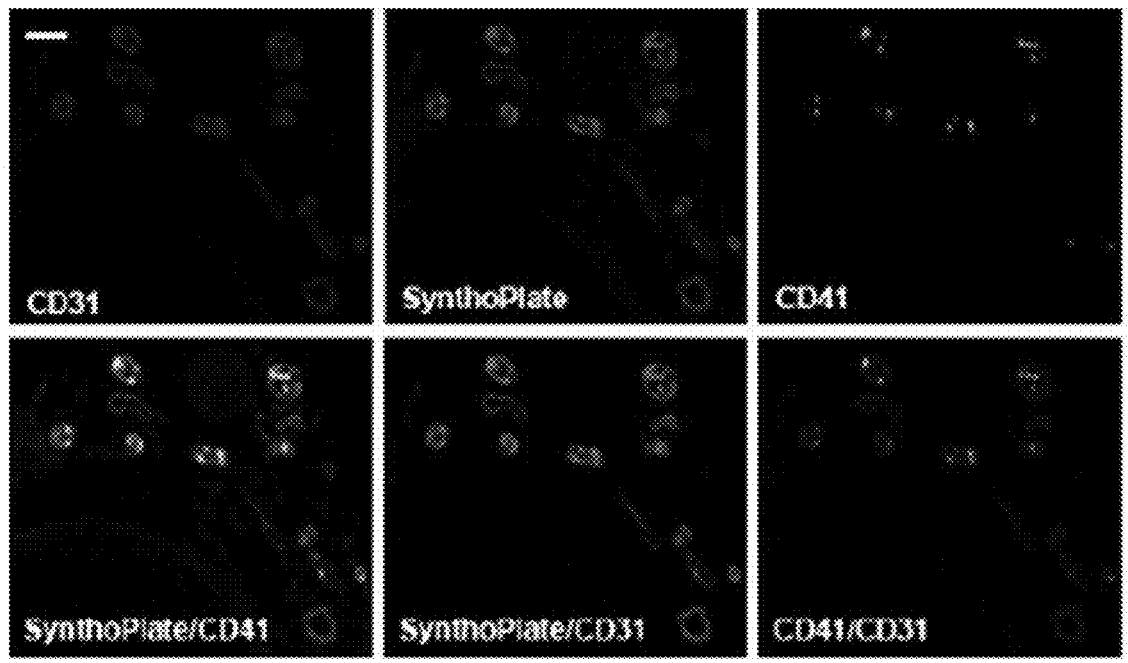
FIGS. 17(A-D) illustrate characterization of SynthoPlate-mediated hemostatic clot in transected tail of thrombocytopenic mouse. (A, B) Representative immunofluorescence microscopy images of tail tissue cryosections (transverse section) proximal to the hemostasized injury site, showing vascular endothelium (CD31), particles (Rhodamine B), platelets (CD41), and corresponding overlays, indicate that (A) tail tissues from SynthoPlate-injected mice have significant colocalization of endothelium, particles, and platelet fluorescence, whereas (B) those from control particle-injected mice show minimal colocalization. Representative scale bar: 25 µm. (C) The percentage of blood vessels showing significant colocalization of particle fluorescence and platelet fluorescence was significantly higher in SynthoPlate-injected thrombocytopenic (TCP) mice than in control (unmodified) particle-injected mice (***P≤0.001). (D) Immunoblot analysis of injured tail tissue from SynthoPlate-treated TCP mice shows a significantly higher amount of high molecular weight fibrin than in tail tissue from control particle-treated TCP mice.
Figure 17B:
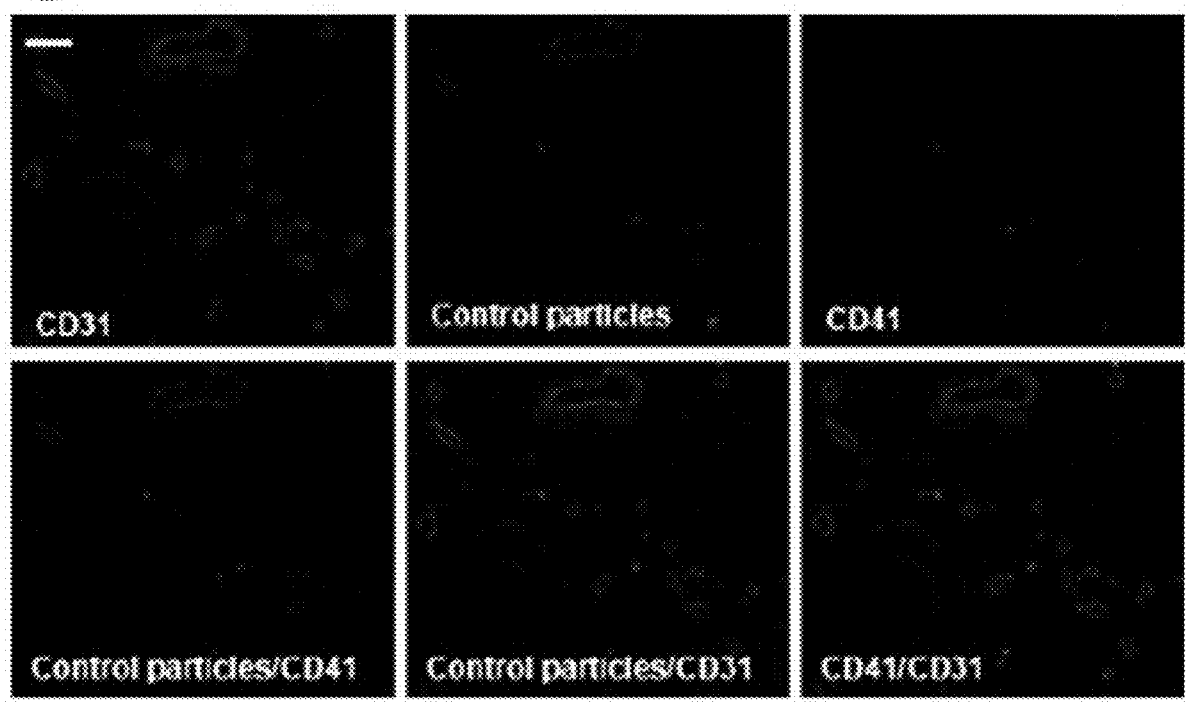
Figure 17C:
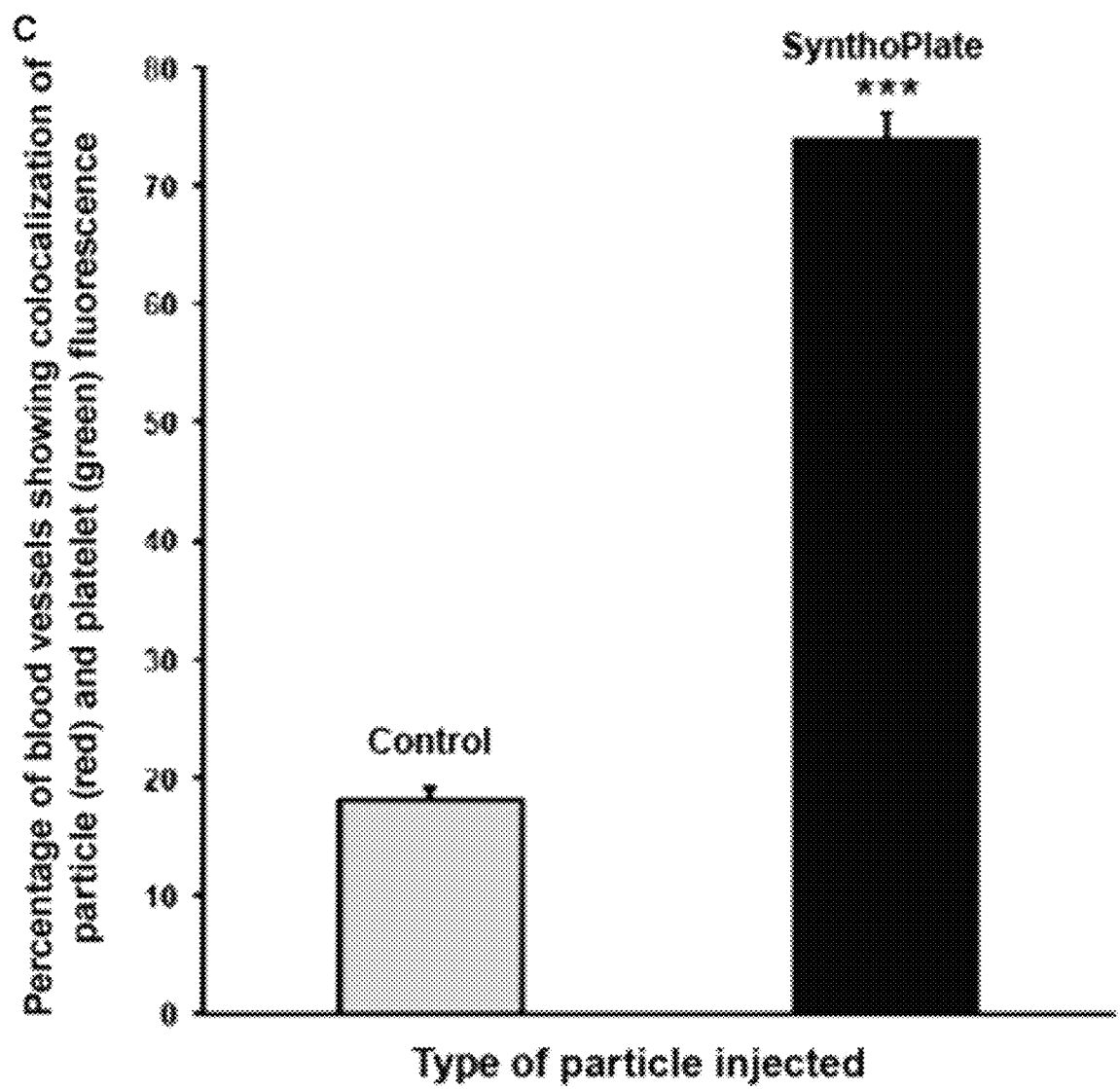
Figure 17D:
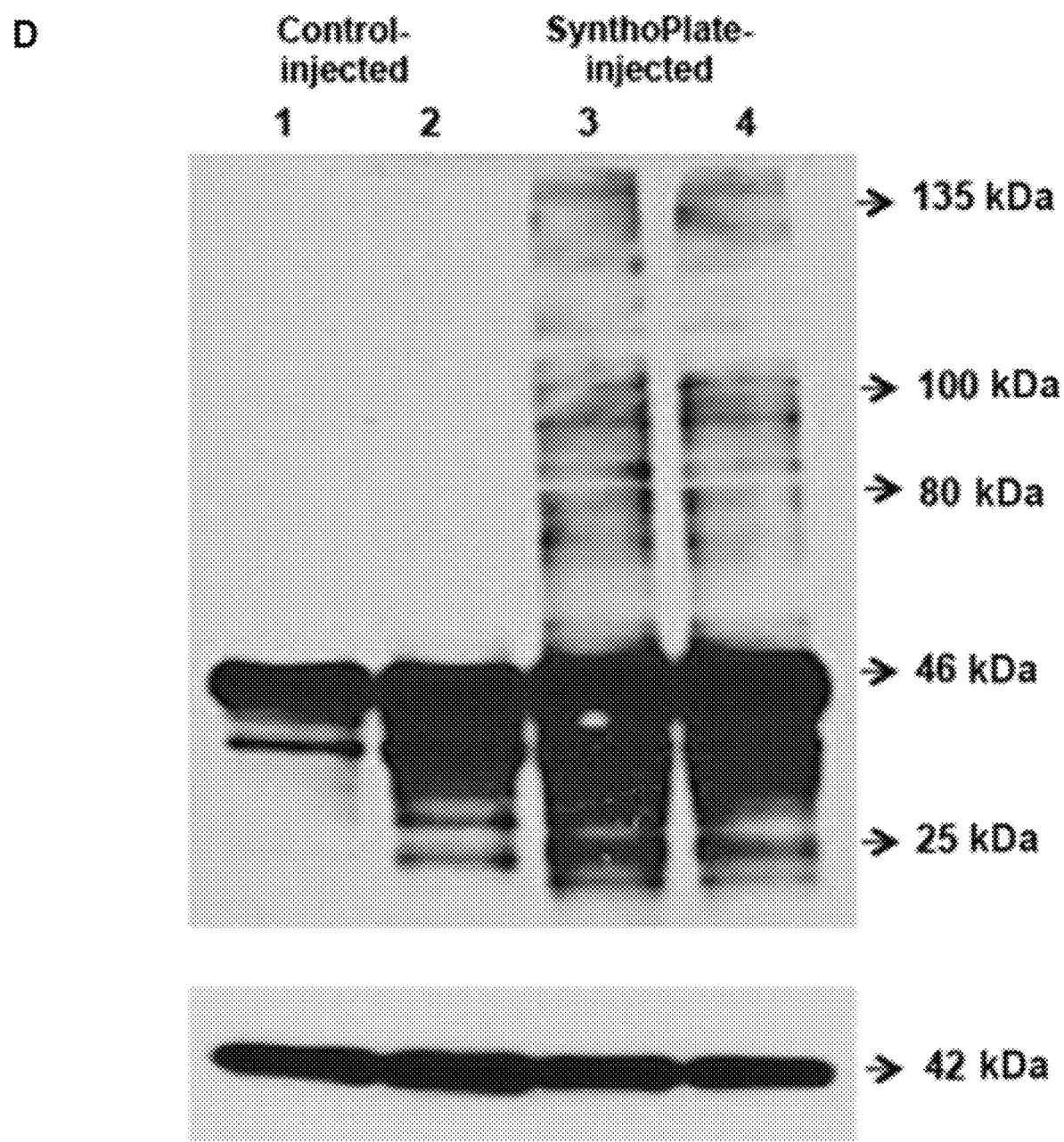

Severe Thrombocytopenia Induction in Mice and Effects of SynthoPlate on Tail Bleeding FIG. 16A1 shows the platelet count following antibody treatment, demonstrating that a total dose of 10 μg of antibody combination (5 μg each) resulted in a ~90% reduction in platelet count (severe thrombocytopenia). Injection of PBS or non-specific mouse IgG (MOPC-21) did not deplete platelets. The effect of platelet depletion on the hemostatic capacity of mice is shown in FIG. 16A2, where 10 lg of antibody injection (i.e., platelet depletion by ~90%) resulted in a four-fold to five-fold increase in tail-bleeding time. This severe thrombocytopenia condition was subsequently used to test the ability of prophylactically administered SynthoPlate to improve hemostasis. FIG. 16B shows the effect of SynthoPlate versus control particle treatment on tail-bleeding time in TCP mice. As is evident, PBS alone or control particles were unable to correct the prolonged bleeding time (400-500 s). In contrast, SynthoPlate was able to significantly correct the bleeding time in a dose-dependent manner. The highest dose of SynthoPlate (1000 $nL^{-1}$, equivalent to the murine native platelet concentration) reduced the bleeding time to ~150 s (>60% reduction as compared with controls), which is close to that of normal mice (~100 s, shown for comparison). These studies demonstrate that SynthoPlate could efficiently correct the hemostatic defect in thrombocytopenia. FIGS. 17A,B shows representative immunofluorescence images of cryosectioned tail tissue immediately proximal to the tail transection site, showing vascular endothelium (CD31 in blue), particle fluorescence (red), platelets (CD41 in green), and corresponding overlays, for SynthoPlate-treated versus control particle-treated TCP mice. FIG. 5C shows the percentage of the vasculature that demonstrated colocalization of CD41 (platelets) and SynthoPlate (or control) particles, determined from 24 representative images per injection group (six mice per group) by manual counting. These images clearly indicate that SynthoPlate has significantly greater ability than control (unmodified) particles to enhance the recruitment and aggregation of platelets in the injured vessels in TCP mice. FIG. 16D shows representative immunoblot data (for fibrin/Fg, and for 3-actin as a loading control) for tail tissue from SynthoPlate-treated versus control particle-treated TCP mice. Individual Fg a, b and c chains are not well resolved, but are seen as prominent bands of ~45-63 kDa. However, higher molecular weight bands, consistent with thrombin-cleaved cross-linked fibrin, are apparent in the SynthoPlate-treated mice (lanes 3 and 4), but are not present in control particle-treated mice (lanes 1 and 2). These results further indicate that, in TCP mice, SynthoPlate-mediated platelet recruitment and aggregation at the injury site (amplification of primary hemostasis) also enhance thrombin generation and fibrin deposition at the site (secondary hemostasis) to improve overall hemostatic capability.

Systemic Safety and Biodistribution of SynthoPlate During 2 h of Circulation

Figure 18A:
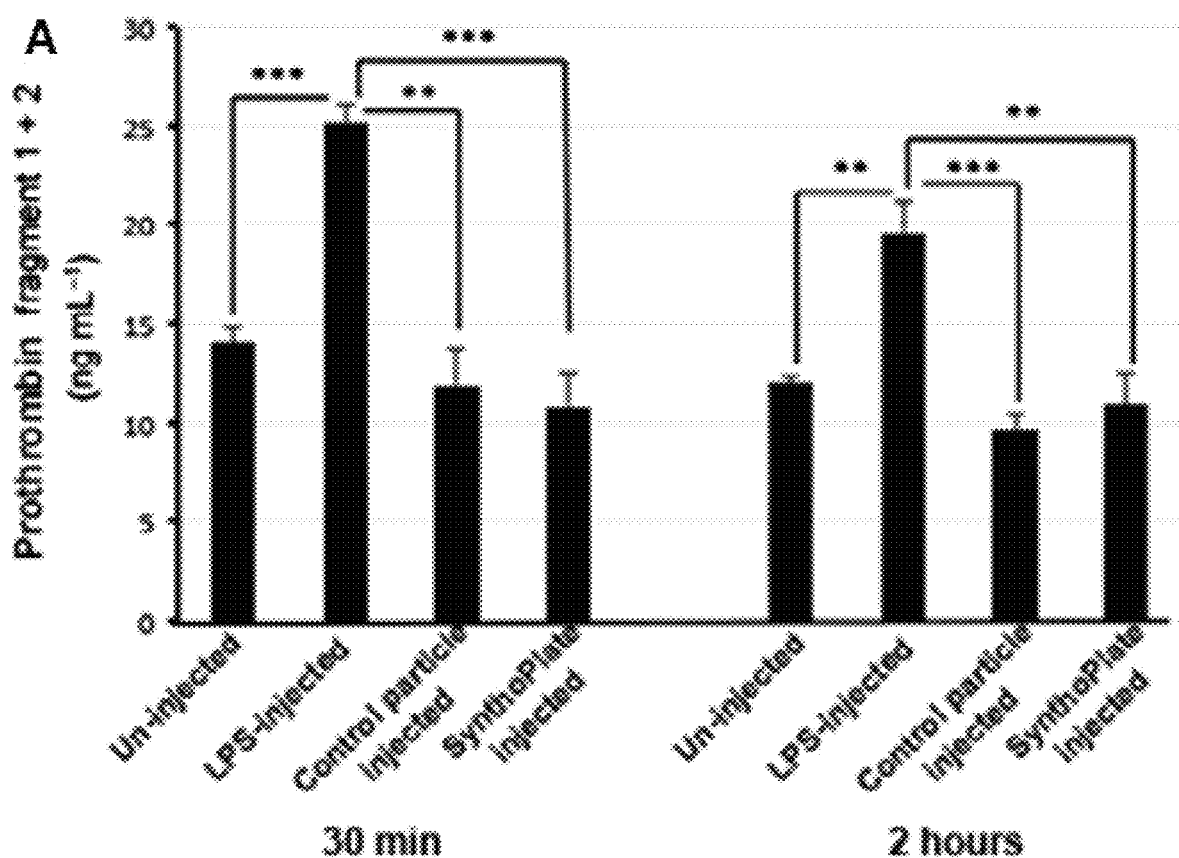
FIGS. 18(A-D) illustrate evaluation of systemic procoagulant risk and biodistribution of SynthoPlate in mice. (A, B) Prothrombin fragment 1+2 ELISA assay (A) and (B) Stago D-dimer assay in mice injected with SynthoPlate indicate that SynthoPlate vesicles do not trigger spontaneous formation of thrombin and fibrin in plasma (minimal systemic procoagulant risk). (C, D) Representative fluorescent images (6-diamidino-2-phenylindole-stained nuclei, red, Rhodamine B-labeled particles) of harvested tissue cryosections (C) and histogram showing systemic localization of SynthoPlate vesicles (D) in thrombocytopenic mice at the 2-h circulation time-point indicate that ~15% of the injected dose is cleared during the 2-h period, with the liver and spleen being the principal organs of vesicle clearance, with much reduced clearance in kidney, heart, and lungs. LPS, lipopolysaccharide.
Figure 18B:
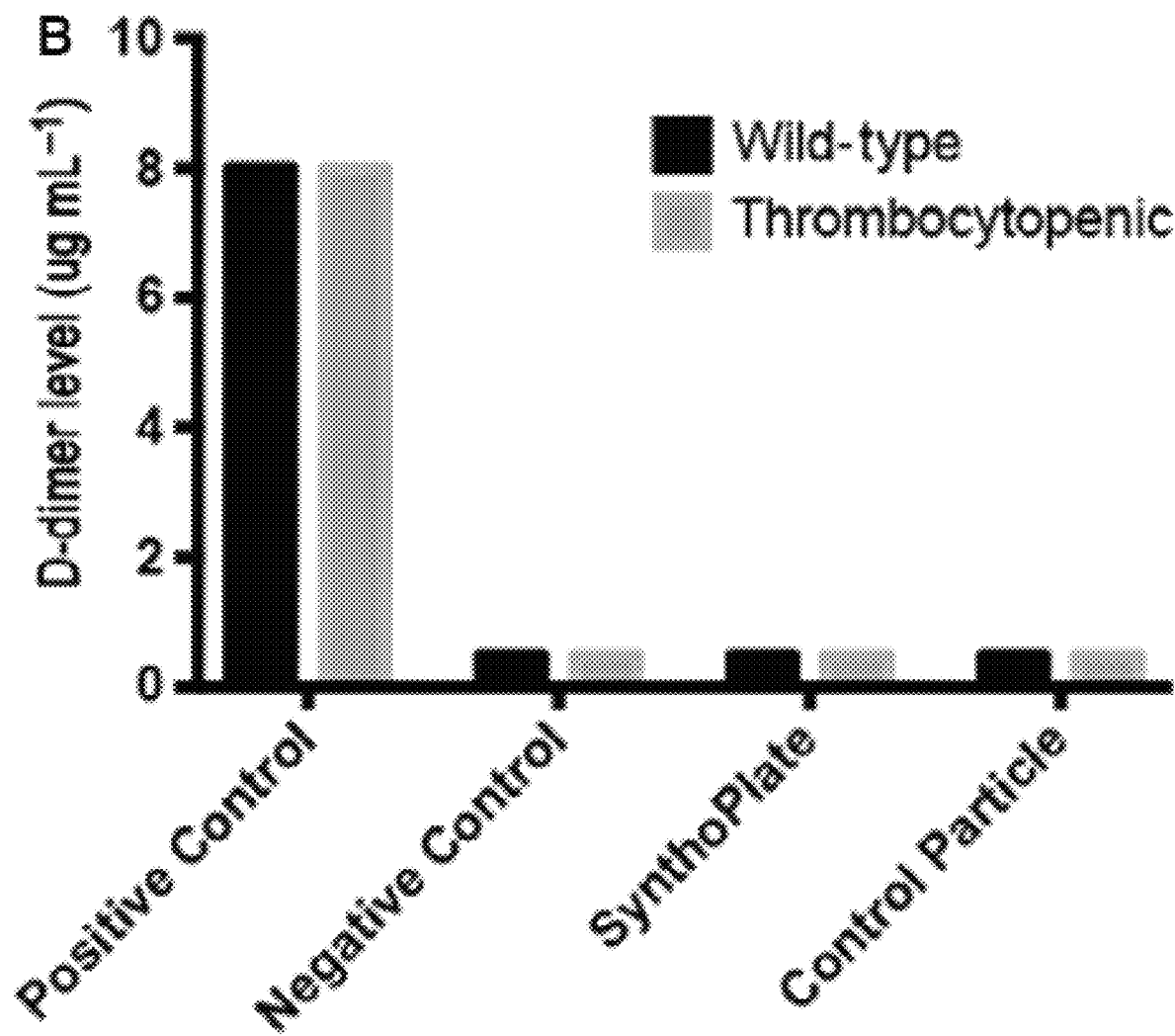
Figure 18C:
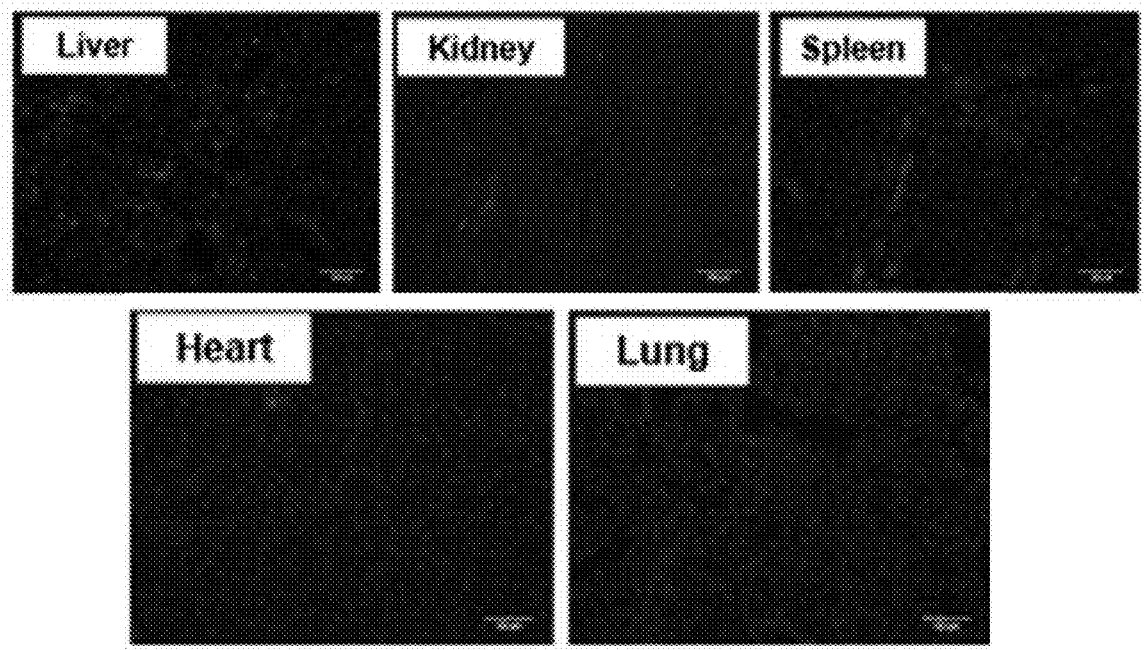
Figure 18D:
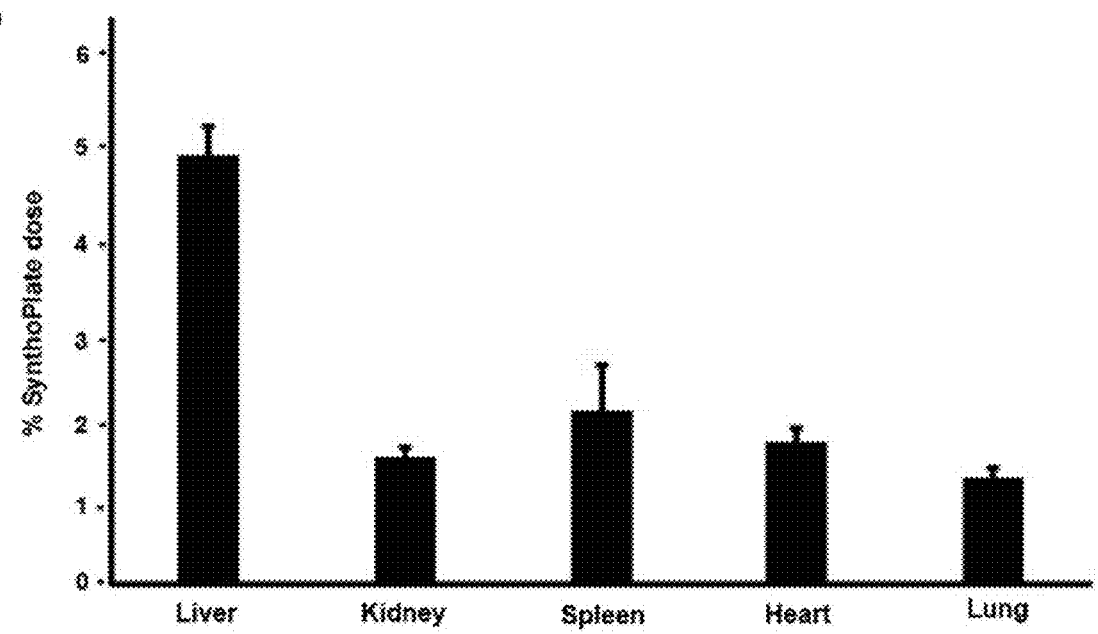
Figure 20A:
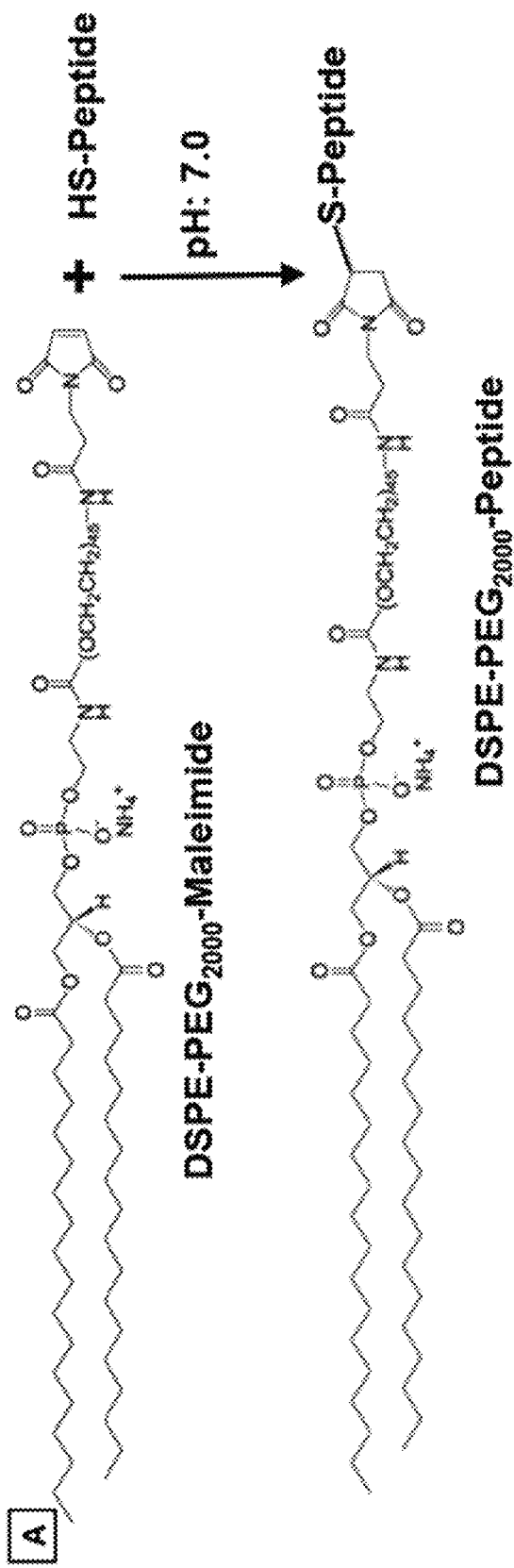
FIGS. 20(A-F) illustrate a reaction schematic and mass spectrometry of DSPE-PEG-peptide conjugates for (A) conjugating Cysteine-terminated peptides to DSPE-PEG2000-Maleimide via thioether linkage to form DSPE-PEG2000-peptide molecules; [B]-to-[F] shows representative mass spectrometry data for peptides, DSPE-PEG2000-Maleimide and final DSPE-PEG-peptide conjugates.
Figure 20B:
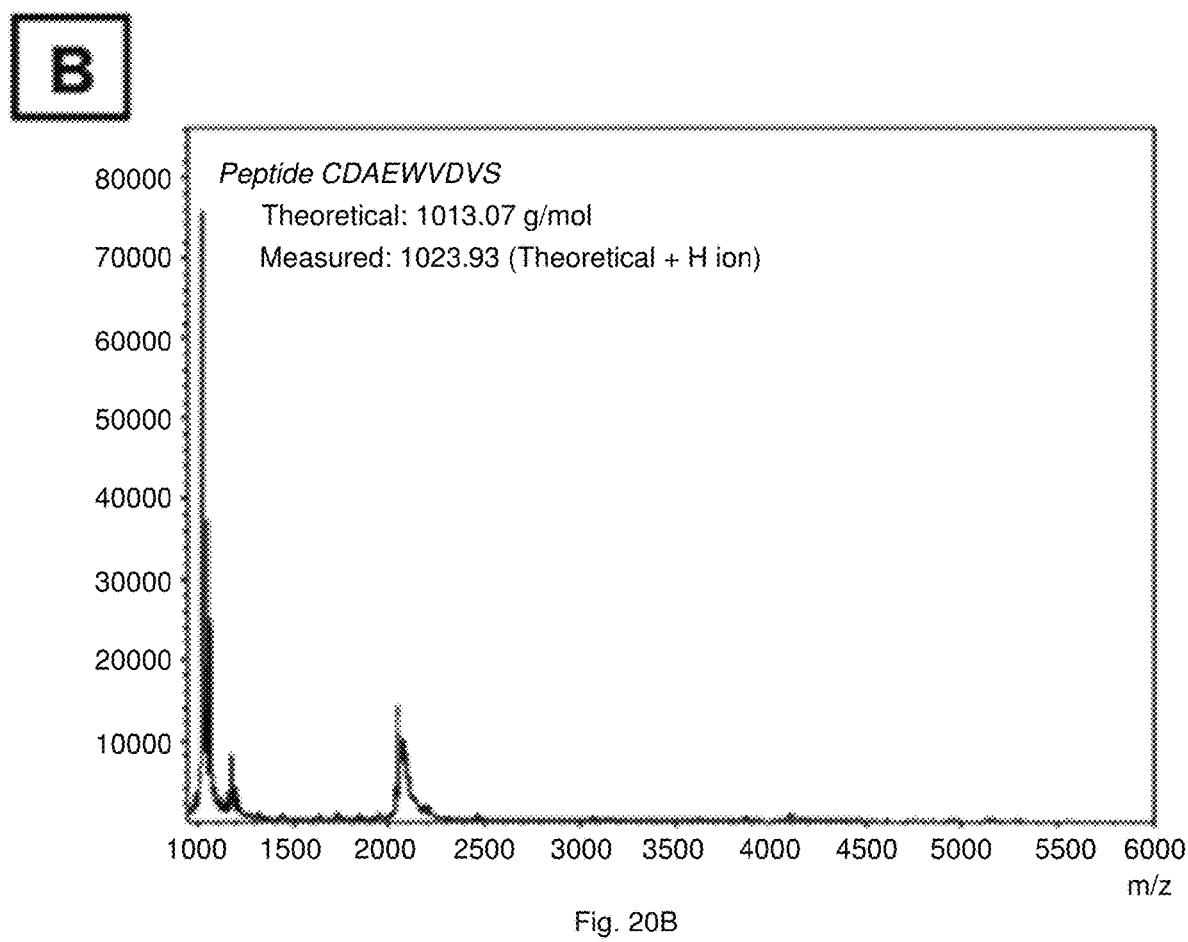
Figure 20C:
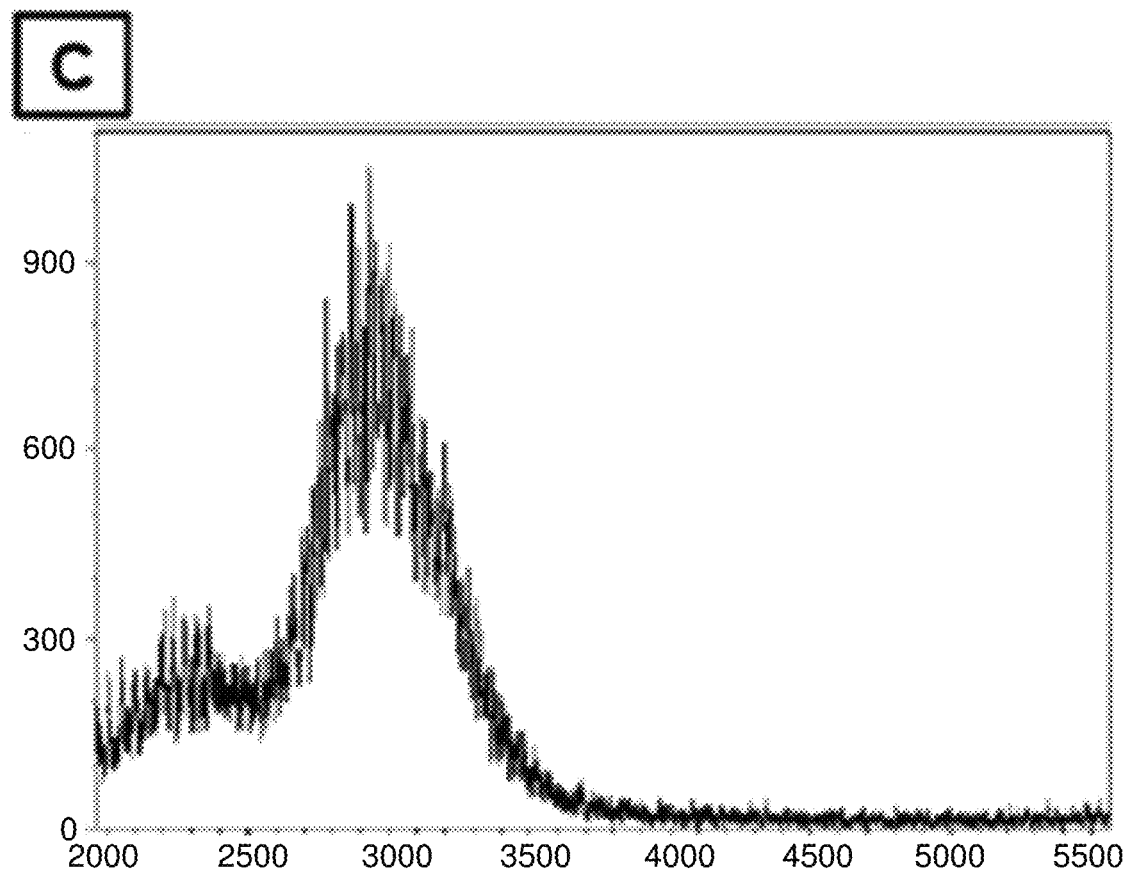
Figure 20D:
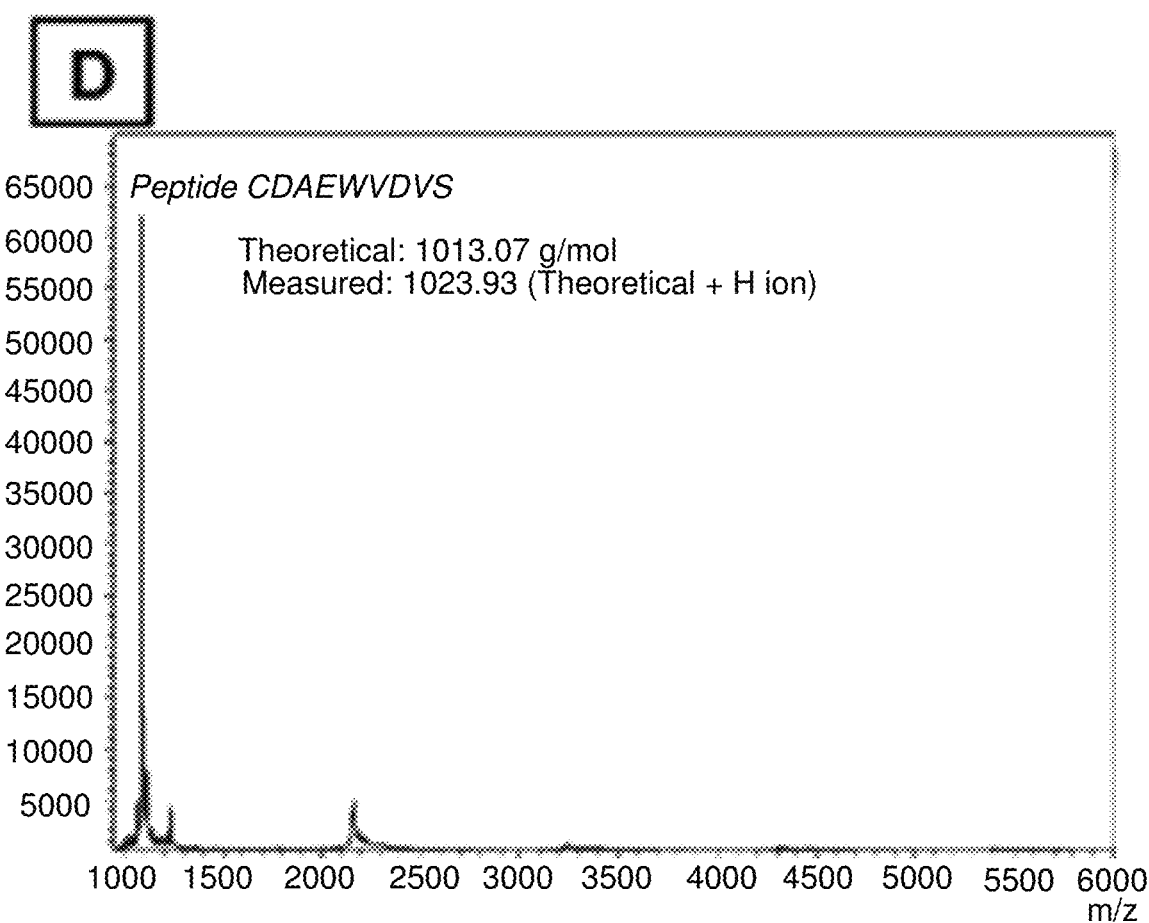
Figure 20E:
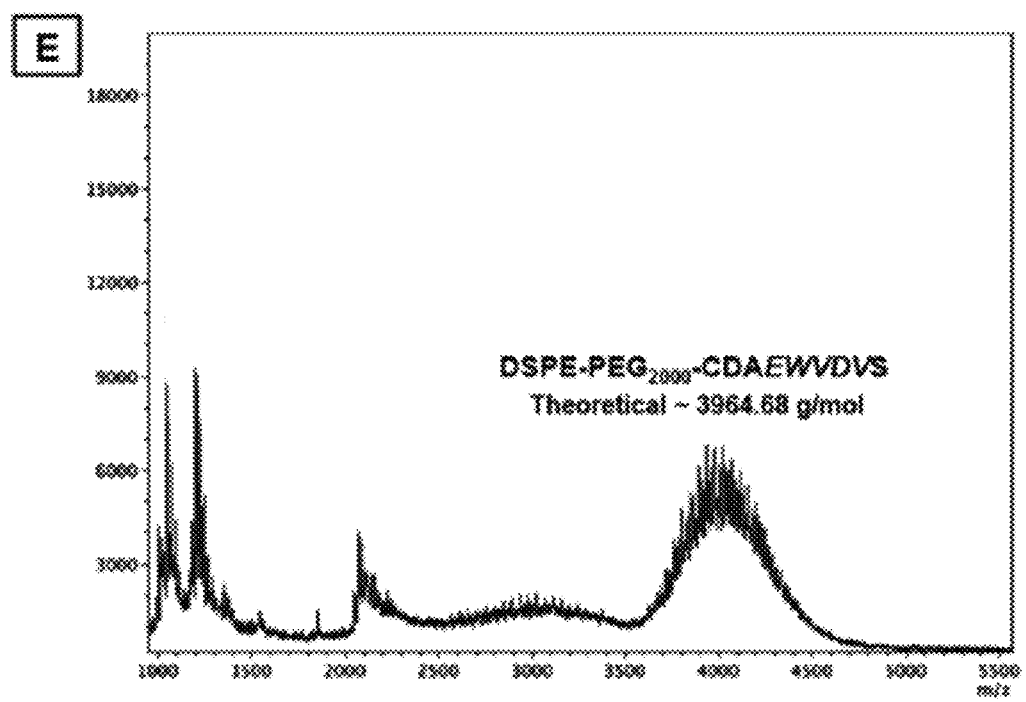
Figure 20F:
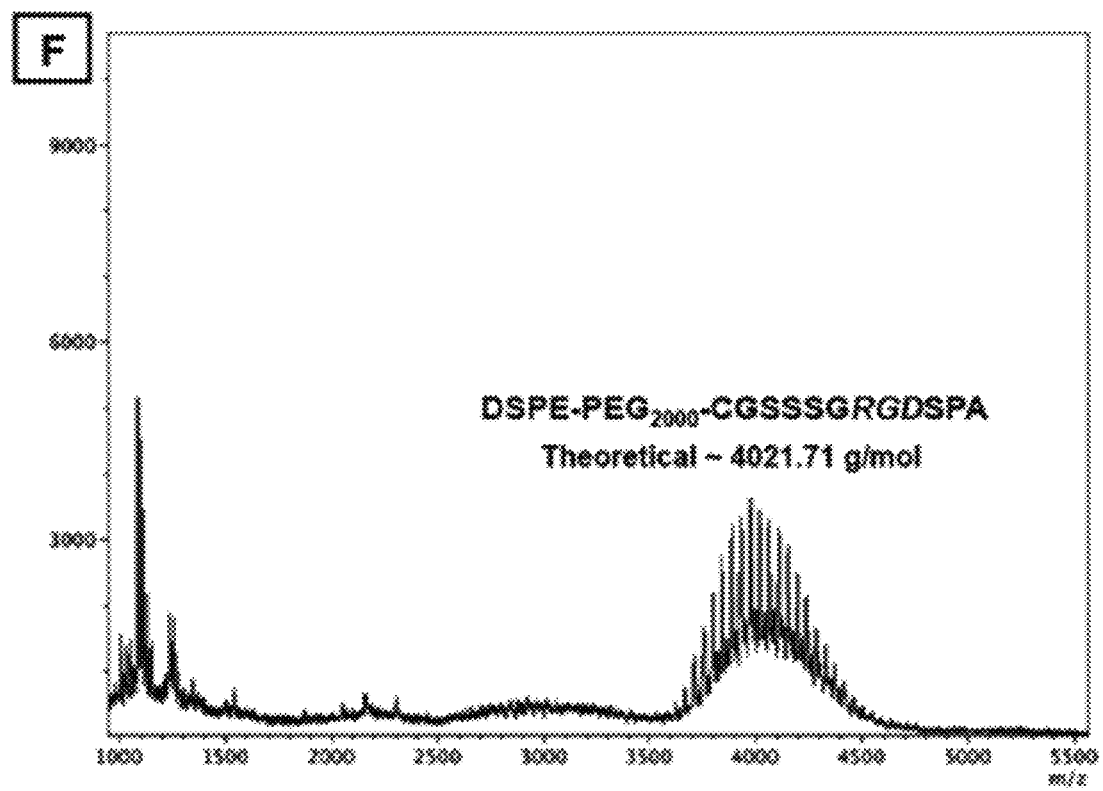
Figure 26:
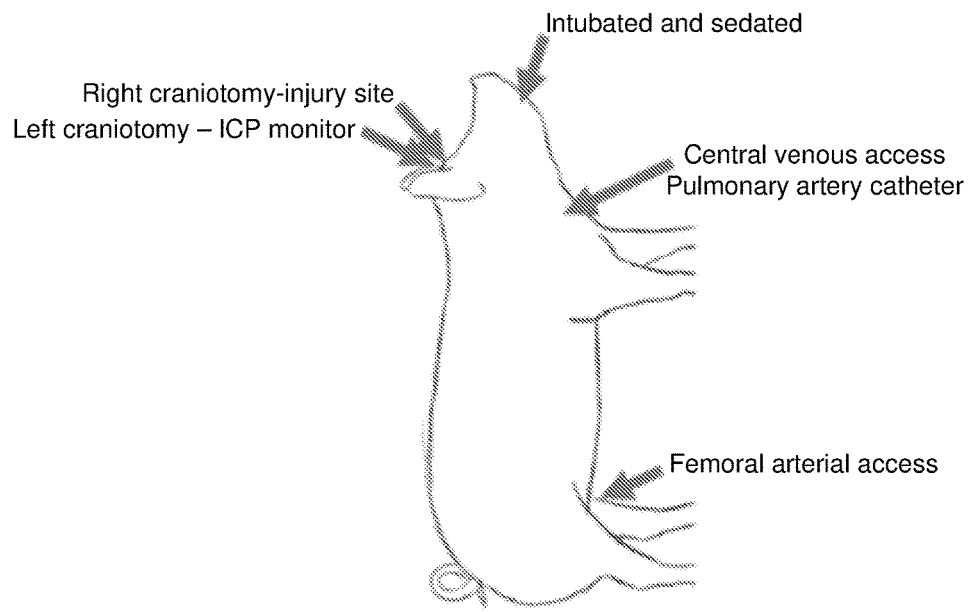
FIG. 26 illustrates a schematic illustration of a porcine traumatic brain injury (TBI)+hemorrhagic shock (HS) model.

FIG. 18A shows 30-min and 2-h time-point results for ELISA-based analysis of prothrombin fragment 1+2 in SynthoPlate-injected mice (untreated mice or LPS-injected mice as controls). SynthoPlate particles did not enhance prothrombin fragment levels, indicating their minimum procoagulant activity in plasma. This was further validated by the Stago D-dimer assay results shown in FIG. 6B, where neither control nor TCP mice were found to have enhanced levels of fibrin D-dimer in the systemic circulation at the 2-h time-point following SynthoPlate or control particle administration (as compared with manufacturer-supplied controls). These in vivo results, combined with those of previous in vitro assays, further establish that SynthoPlate does not have systemic prothrombotic and procoagulant effects. FIG. 18C shows representative cryosection fluorescence images of tissues from various clearance organs harvested from killed mice at the 2-h time-point, and FIG. 18D shows the percentage localization of SynthoPlate particles (based on RhB fluorescence) analyzed from homogenates of such organs. During the 2-h circulation period, only ~15% of the injected dose was cleared, mostly in the liver and spleen, and minimally in other organs. This suggests that the majority of the dose remained in the circulation to facilitate hemostasis in the event of injury. In fact, complementary studies using radiolabeled particles further indicate that SynthoPlate has a reasonably long circulation residence time. As SynthoPlate design utilizes polyethylene glycol-decorated lipid vesicles, this long circulation capability and low clearance are in good agreement with reports for similar nanoparticles (e.g., Stealth liposomes).

In this example, we show that the SynthoPlate vesicles themselves do not have systemic prothrombotic or procoagulant risks, but can amplify activated platelet-mediated primary and secondary hemostatic mechanisms selectively at a bleeding site, even at low platelet concentrations. Our in vivo studies further confirmed that prophylactic administration of SynthoPlate can dose-dependently improve hemostasis in a tail-bleeding model in severely thrombocytopenia (TCP) mice, with higher doses being capable of correcting bleeding times to levels comparable to that of normal mice. One should note that the starting platelet count in normal mice (~1 million per microliter) is significantly higher than that in normal human (~250 000 per microliter), and hence the severity of the TCP bleeding risk in mice is associated with the percentage platelet depletion and not the absolute number of remaining platelets. Also, as tail-bleeding studies may have some experimental heterogeneity, we have meticulously followed the ISTH standardization recommendations for this model to minimize errors and variabilities. Immunofluorescence microscopy and immunoblot analyses confirmed striking colocalization of murine platelets and SynthoPlate, as well as enhanced formation of fibrin in hemostatic foci of SynthoPlate-injected mice. In vivo, SynthoPlate vesicles showed reasonably long circulation periods, and were primarily cleared by the liver and spleen. The SynthoPlate technology may also find potential uses in the emergency treatment of traumatic hemorrhage, and as a targeted drug delivery platform in various platelet-relevant diseases.

Example 4

Intravascular administration of plasminogen activators is a clinically important thrombolytic strategy to treat occlusive vascular conditions. A major issue with this strategy is the systemic off-target drug action, which affects hemostatic capabilities and causes substantial hemorrhagic risks. This issue can be potentially resolved by designing technologies that allow thrombus-targeted delivery and site-specific action of thrombolytic drugs. To this end, leveraging a liposomal platform, we have developed platelet microparticle (PMP)-inspired nanovesicles (PMINs), that can protect encapsulated thrombolytic drugs in circulation to prevent off-target uptake and action, anchor actively onto thrombus via PMP-relevant molecular mechanisms and allow drug release via thrombus-relevant enzymatic trigger. Specifically, the PMINs can anchor onto thrombus via heteromultivalent ligand-mediated binding to active platelet integrin GPIIb-IIIa and P-selectin, and release the thrombolytic payload due to vesicle destabilization triggered by clot-relevant enzyme phospholipase-A2. Here we show on the evaluation of clot-targeting efficacy, lipase-triggered drug release and resultant thrombolytic capability of the PMINs in vitro, and subsequently demonstrate that intravenous delivery of thrombolytic-loaded PMINs can render targeted fibrinolysis without affecting systemic hemostasis, in vivo, in a carotid artery thrombosis model in mice. Our studies establish significant promise of the PMIN technology for safe and site-targeted nanomedicine therapies in the vascular compartment.

For the PMIN design (FIG. 19B), the clot-specific active anchorage was rendered by heteromultivalently surface-decorating glycerophospholipid-based liposomal vesicles with peptide ligands that can specifically bind to stimulated integrin GPIIb/IIIa and P-selectin on activated platelets. Activated platelets are an ideal cellular target for PMIN binding to thrombi, since aggregation of activated platelets and platelet-mediated promotion of coagulation mechanisms are hallmark events in thrombosis. Specifically, the fibrinogen derived peptide sequence GSSSGRGDSPA was used for active GPIIb-IIIa-binding and the sequence DAEWVDVS was used for P-selectin binding. For thrombolytic drug encapsulation, we selected streptokinase (SK) as a model fibrinolytic drug, especially since its direct systemic use is known to cause significant off-target hemorrhagic side-effects (and therefore will be a good control to compare). For clot-relevant stimulus, we selected secreted phospholipase A2 (sPLA2, group II) as a candidate, since it is reported to be produced from activated platelets and inflammatory cells in athero-thrombotic milieu and can cleave the sn-2 ester bonds in glycerophospholipids, thereby destabilizing lipid vesicles for payload release. In fact, PLA2 action can result in release of arachidonic acid from PMPs to augment transactivation and aggregation of platelets in thrombosis. Building on these design components, our central hypothesis was that intravenously administered SK-loaded PMINs can actively anchor onto thrombi (FIG. 19C, C1), where thrombus-associated sPLA2 activity can destabilize the vesicles to render clot site-selective SK release for targeted fibrinolytic action (FIG. 19C, C2 and C3).

Materials and Methods

Materials

Phosphate Buffered Saline (PBS), 3.8% w/v sodium citrate, Bovine Serum Albumin (BSA), chloroform, methanol, ethanol, AlexaFluor 488-conjugated fibrinogen (AF488-Fg) and 1,2-Bis-BODIPY® FL-C11-sn-Glycero-3-Phosphocholine (bis-BODIPY® FL C11-PC) were obtained from Thermo Fisher Scientific (Pittsburgh, Pa., USA). Cholesterol, secreted phospholipase A2 (sPLA2), calcium chloride and collagen were obtained from Sigma Aldrich (St. Louis, Mo., USA). Adenosine Diphosphate (ADP) was purchased from Bio/Data Corporation (Horsham, Pa., USA). Cysteine-terminated peptides CGSSSGRGDSPA and CDAEWVDVS were custom-synthesized and purchased from Genscript (Piscataway, N.J., USA). Distearyl phosphatidyl choline (DSPC), maleimide-terminated polyethylene glycol-conjugated distearyl phosphatidyl ethanolamine (DSPEPEG2000-Mal) and Rhodamine-B-dihexadecanoyl-sn-glycero-3-phosphoethanolamine (DHPE-RhB) were obtained from Avanti Polar Lipids (Alabaster, Ala., USA). Polycarbonate membrane filters with 200 nm pores for vesicle extrusion were obtained from Whatman (Kent, UK). For streptokinase analysis the chromogenic assay Chromogemix S-2251 was purchased from Diapharma (West Chester, Ohio, USA). The Parallel Plate Flow Chamber (PPFC) system was purchased from Glycotech (Gaithersburg, Md., USA). Aggregometry studies were done on a ChronoLog aggregometer. All inverted fluorescence microscope studies were carried out using a Zeiss Axio Observer D1 microscope fitted with a CCD camera. For in vivo studies on mice, anesthesia agents ketamine was obtained from Fort Dodge Animal Health, IA, USA and xylazine was obtained from Hospira, Ill., USA. Rhodamine 6G for in vivo mouse platelet labeling and ferric chloride (FeCl3) for carotid artery thrombus induction were obtained from Sigma. All intravital microscopy studies were carried out using a Leica DMLFS fluorescent microscope with a Gibraltar Platform (EXFO, Quebec, Canada).

Preparation of Heteromultivalently Ligand-Decorated PMINs

The peptides CGSSSGRGDSPA and CDAEWVDVS were conjugated via thioether reaction to DSPE-PEG2000-Mal through the cysteine termini to form DSPE-PEG2000-GSSSGRGDSPA and DSPE-PEG2000-DAEWVDVS conjugates. The peptides and resulting DSPE-PEGpeptide conjugates were characterized by mass spectrometry. For PPFC-based in vitro platelet-rich clot-targeting studies DSPC, DhPERhB, cholesterol and DSPE-PEG-peptide conjugates were dissolved in 1:1 chloroform: methanol, and this lipid mixture was subjected to standard reverse phase evaporation and lipid hydration technique followed by extrusion through 200 nm pore size polycarbonate membrane in a pneumatically controlled lipid extruder (Northern Lipids). Resultant vesicles were characterized for their size distribution using dynamic light scattering (DLS) and cryo transmission electron microscopy (cryoTEM) and the size was found to be approximately 150 to 170 nm in diameter. For the various vesicle formation, DSPC content was always maintained at 50 mol % and DHPE-RhB content was always maintained at 1 mol % of total lipid. For homomultivalently decorated vesicles (single peptide decoration), the corresponding DSPE-PEG-peptide content was maintained at 2.5, 5, or 10 mol % of total lipid, while for heteromultivalently decorated vesicles (bearing both peptides) the total DSPE-PEG-peptide was kept at 5 mol %, with each lipid-peptide conjugate at 2.5 mol %. The remainder of the lipid membrane content was cholesterol, since it is known to interdigitate with lipids to enhance membrane stability of bilayer vesicles. It is to be noted that the heteromultivalent composition was used as a test condition for the current thrombolytic studies, but if needed the heteromultivalent composition can be modulated to vary relative peptide ratios as well as the total peptide content if needed. For analysis of sPLA2-induced vesicle degradation, vesicles were synthesized with adjusting the DSPC component to have DSPC:bis-BODIPY FL C11-PC at 20:1 ratio in mole % (as per ThermoFisher specification), keeping everything else constant. For SK encapsulation and release studies, 25 kU/ml of SK was dissolved in the PBS used for lipid film hydration during the vesicle preparation and after extrusion the SK-loaded vesicles were purified from unencapsulated SK using Amicon ultracentrifugal filters on an ultracentrifuge.

In Vitro Studies of Vesicle Binding and Retention on Active Platelet-Rich Clots

Parallel plate flow chamber (PPFC) studies were done where platelet-rich thrombi was formed by incubating activated platelet rich plasma (PRP) over Type III collagen-coated circular region on glass slides. For this, acid washed glass microscope slides were incubated for 1 h with suspensions of BSA and type III collagen in two adjacent circular areas respectively delineated by 8 mm diameter O-rings (schematic shown in FIG. 21A). The suspensions were gently washed off with PBS and the coated areas were incubated with 200 ml of platelet-rich plasma (PRP) containing ADP and $Ca^{++}$. The active platelets in PRP adhered spontaneously to the collagen-coated region and simulated a platelet-rich clot but not to albumin-coated region (confirmed by SEM shown in FIG. 21A). It is noted that since the incubations are done with PRP, the platelet-rich collagen-coated surface shows dense presence of central bodies of adjacent activated platelets along with fibrin strands and individual 'spread platelet' pseudopodal morphology is not clearly visible. Similar incubation done with 'washed platelets' only (instead of PRP) allows confirmation of activated 'spread platelet' pseudopodal morphologies. The PRP was gently washed off with PBS, the slides were fixed with 4% paraformaldehyde, vacuum sealed within a parallel plate flow chamber system placed under an inverted fluorescence microscope (Zeiss AxioObserver.D1) and were exposed to the flow of the RhB-labeled vesicles (homomultivalently decorated, heteromultivalently decorated, or unmodified) at various flow rates producing wall shear rates of 300-4000 sec-1 in a recirculating loop for 30 min. This was followed by flow of PBS only (at the same flow rates and hence shear values) for an additional 15 min in an open loop to remove any loosely bound vesicles. Thus, imaging up to 30 min time point allowed analysis of 'binding' and following that at the 45 min time point allowed analysis of 'retention' of vesicles on platelet-rich versus platelet-poor surfaces. Images at various time points were analyzed for surface-averaged RhB fluorescence intensity (as a quantitative measure of vesicle binding and retention), using the Zeiss AxioVision software. For the current studies, experiments and analyses were done for homomultivalent decorations of 2.5 mol %, 5 mol % and 10 mol % peptide compositions compared with heteromultivalent peptide composition of 5 mol % (2.5 mol % of each peptide). Additional PPFC experiments were also done by varying the relative ratios of peptides while keeping the total heteromultivalent peptide composition at 5 mol %

Characterization of sPLA2-Induced Vesicle Degradation and Payload (SK) Release

The ability of sPLA2 to degrade and destabilize the PMINs for payload release was characterized in vitro by incorporating fluorescently labeled (BODIPY-labeled) lipid within the vesicle membrane and monitoring the release of BODIPY over time under lipase action. The bulk of the lipid in the vesicle membrane was DSPC, which is a known substrate for sPLA2. An analogous BODIPYlabeled phosphatidylcholine, bis-BODIPY FL C11-PC, (Excitation: 488 nm, Emission: 530 nm) was incorporated at 5 mol % along with DSPC in the vesicle fabrication. In this assay, the BODIPY is selfquenched initially in the intact membrane, but cleavage of the BODIPY-labeled membrane lipid by sPLA2 results in release of BODIPY and corresponding increase in emitted fluorescence signal. Bis-BODIPY FL C11-PC-labeled PMINs thus prepared were incubated in the presence of sPLA2 (final concentration 1 μg/ml) in 450 μl assay volume per well in 96-well plate and resultant fluorescence signal from released BODIPY (due to membrane degradation by sPLA2) was monitored over time using a fluorescence platelet reader. Next, to determine whether such lipase-induced vesicle degradation leads to payload release, model thrombolytic drug streptokinase (SK) was encapsulated within similarly prepared PMINs and incubated in absence versus in presence of sPLA2. For this, SK was loaded within the vesicles using the RPEE technique with 25 kU/ml SK in PBS to reconstitute the lipid film and free SK was removed using ultracentrifugation. Encapsulation efficiency was evaluated by disrupting the vesicles with Triton-X and exhaustively releasing the encapsulated SK, which was analyzed spectrometrically (on a UV-Vis platelet reader) using Chromogenix S-2251 assay. For this, the SK-loaded vesicles were suspended in 5 mM Tris-HCl p 1 mM $CaCl_2$ buffer in microcentrifuge tubes in the presence or absence of 2.5 ng/ml sPLA2 for 0e5 h on a gyratory shaker (60 rpm) at 37° C., and 100 μl of the suspension was aliquoted at various time points to measure the released SK by the S-2251 assay. In this assay, released SK converts the plasminogen reagent to plasmin, which in turn acts on the chromogenic substrate reagent to liberate p-nitroaniline (pNA) that is measured spectrophotometrically at 405 nm. This signal is in linear calibration with respect to active SK concentration, and hence the absorbance signal represents released SK concentration.

Evaluation of Thrombolytic Capacity of Vesicles In Vitro

SK-loaded Rh-B-labeled (red fluorescent) heteromultivalently decorated (2.5 mol % of each peptide at total 5 mol %) PMINs were prepared. Glass microscope slides were incubated with collagen suspension in a circular region for 30 min (similar to slide preparation for PPFC-based binding studies) and then gently washed with 1×PBS. PRP with AlexaFluor 488-conjugated fibrinogen (6% v/v of 1.5 mg/mL, green fluorescent) was briefly mixed with α-thrombin and 0.5 M $CaCl_2$, to final concentrations of 5 nM and 25 μM respectively, to initiate clot formation and the mixture was pipetted (100 μl volume) onto the collagen-coated surface region. The clot was allowed to incubate for 1 h and then gently washed with 1×PBS to remove loosely bound components. The slide thus formed with platelet-rich green fluorescent fibrin clot on its surface, was sealed into the parallel plate flow chamber (PPFC) system, to be imaged under the inverted fluorescence microscope. The objective was focused on an area at the edge of the clot such that the initial field of view enabled observation of the green fluorescence of the fibrin clot throughout the whole area of view, and the clot lysis could then be observed as the loss of this fluorescence. SK-loaded RhB-labeled heteromultivalently platelet-targeted or untargeted PMINs in plateletpoor plasma (final concentration of $2.1 \times 10^{11}$ particles/mL) were flowed along with sPLA2 (2.5 ng/ml) over the clot at 300 $sec^{-1}$ shear rate and the clot (stability or lysis) was imaged (one image per minute) over a period of 60 min with a 10× objective. In this experimental set-up, sPLA2-triggered degradation of clot-bound PMIN vesicles and resultant SK release was expected to convert the plasminogen to plasmin and thereby lyse the fibrin of the clot. This mechanism would result in reduction of red fluorescence (degradation of clot-bound PMINs) and green fluorescence (lysis of fibrin in clot), as depicted in FIG. 23A, imaged over time under inverted fluorescence microscope.

Vesicle Binding to Mouse Carotid Artery Thrombus In Vivo

The mouse model experiments were carried out in accordance to Cleveland Clinic Foundation IACUC-approved protocols, using ferric chloride ($FeCl_3$)-induced vascular injury and thrombosis model in mouse. For this, 8-12 week old male C57BL6 mice were anesthetized with a mixture of ketamine (100 mg/kg) and xylazine (10 mg/kg) via intraperitoneal injection, and anesthesia was confirmed by toe clipping. The right common carotid artery (CA) was exposed. A 1×2 mm piece of Whatman #1 filter paper was saturated with 7.5% $FeCl_3$ solution and placed directly on the CA for ~1 min (FIG. 24A). In our experience, this method produces a thrombus that occludes the vessel ~50% in 5 min and almost full occlusion around 11-12 min after injury. Representative SEM images of substantial platelet-rich clot formation on the luminal side of the artery upon such vascular injury where progressive magnification scales show high accumulation of platelets upon vessel injury and fibrin generation on individual platelets. RhB-labeled (red fluorescent) non-targeted (unmodified) vesicles or platelet targeted (heteromultivalently decorated) PMINs in saline were then injected at 30 mg/kg in the right jugular vein and vesicle interaction with thrombus was imaged in real time in the anesthetized mice using a Leica intravital microscope. In parallel studies, similarly treated mice were euthanized with an overdose of anesthesia cocktail (IACUC approved protocol), the thrombosed artery was excised, sectioned longitudinally, fixed in PFA, placed on glass microscope slides and imaged with the luminal side facing the objective to observe RhB fluorescence in the thrombus. In additional experiments, $FeCl_3$-induced thrombi were created in the carotid of mice (n=3) as before, 100 µl RhB-labeled targeted PMIN was injected into the mouse circulation system via the jugular vein catheter, the circulation was maintained for another 10 min in a 37° C. warming chamber and then mice were euthanized. Lung, liver, kidney and spleen as well as the thrombosed carotid artery (right, ~2-3 mm length section) and non-thrombosed carotid artery (left, ~2-3 mm length section) were harvested, snap-frozen in liquid nitrogen and dried in a lyophilizer. The dry weight of the organs and tissues was recorded. The organs and tissues were then homogenized at 4000 rpm for 2 cycles of 25 s with a 5 s delay using a BeadBug Microtube Homogenizer (Benchmark Scientific, Edison, N.J.) with 3.0 mm high impact zirconium beads. Samples were shaken overnight at 750 rpm at 37° C. in a 1:1 solution of methanol/chloroform to extract RhB-conjugated conjugated lipids. These samples were centrifuged at 12,000 g for 20 min and the supernatant, containing RhB-labeled lipids, was collected. For the thrombosed versus non-thrombosed carotid samples, the overall fluorescence intensities of the processed samples were recorded using a platelet-reader. Assuming that the RhB fluorescence in these samples originate from the anchorage and localization of the PMINs in the carotid, the fluorescence intensities (hence PMIN localization) within thrombosed versus non-thrombosed carotid of the same animal were recorded. For the samples from clearance organs, the RhB-labeled lipids were resolved using Waters Acquity UPLC system (column:Waters BEH C8 1.7 mm) and analyzed with a fluorescence detector (Waters Corporation, Milford, Mass., USA) using excitation wavelength 560 nm and emission wavelength of 580 nm. Accordingly, the uptake of PMINs in the clearance organs was determined by calculating the percent (%) injected dose using an RhB-fluorescence based calibration curve for PMINs.

Targeted Thrombolysis In Vivo Using sPLA2-Responsive PMINs

For targeted thrombolytic capacity assessment, Rhodamine 6G solution was first injected into the right jugular vein of the mouse to render direct fluorescent labeling of circulating platelets and the $FeCl_3$-induced thrombus was created in the carotid as before, such that the formation of the thrombus and extent of vessel occlusion can be observed directly by monitoring the fluorescent platelets in the artery with intra-vital microscopy. For this, the carotid artery was thrombosed as before and 100 ml of Rhodamine 6G solution was injected into the right jugular vein that results in direct fluorescent labeling of circulating platelets. This allows for imaging platelet-rich thrombus formation (and lysis) in real time. Free SK, or, non-fluorescent SK-loaded enzyme-responsive non-targeted (unmodified) vesicles, or, non-fluorescent SK-loaded enzymeresponsive PMINs, or non-fluorescent 'blank' (i.e. no SK loading) enzyme-responsive PMINs were injected via the jugular catheter, ~5 min after thrombus induction. Free SK suspension, SK-loaded unmodified vesicles, as well as, SK-loaded targeted PMIN vesicles, all contained ~400 IU of SK and suspended in 200 µL saline. The effect of these various treatments on delaying the thrombus growth over time was imaged by intravital microscopy, with images recorded for 10 s every minute for the first 10 min and then 10 s every other minute until the end of the experiment. In this experimental framework the thrombolytic drug is expected to constantly lyse the forming thrombus and hence delay vessel occlusion, when compared to no drug treatment. The end points of the experiment were: 1) when blood flow had ceased for >30 s due to vessel occlusion, or 2) if occlusion was not observed in 30 min after SK (free or vesicle-encapsulated) administration. In our experience with this model, at ~5 min after FeCl3-induced endothelial damage the thrombus occludes about 30-50% of the blood vessel and upon further growth of the occlusive thrombus, numerous larger cells (leukocytes) start to roll on the vessel wall at the proximal site of the thrombus and the blood flow usually stops within 2-3 min of the appearance of these large cells. The thrombolytic effect was quantitatively expressed as 'time to delay' for vessel occlusion (blood flow cessation) if vessel was fully occluded before 30 min post-injury or the 30 min data point if vessel occlusion did not occur by 30 min.

Effect of Free SK Versus PMIN-Encapsulated SK on Systemic Hemostasis in Mice

'Tail bleeding time' is a standard method for assessing hemostatic disorders in mouse models and therefore this was used to assess the systemic effect on hemostasis of free SK versus nanovesicle-encapsulated SK administration in mice. For this, 8-12 weeks old C57Bl/6 mice were anesthetized as before with ketamine/xylazine cocktail, and free SK or PMIN-encapsulated SK (400 IU/mouse) in 200 mL saline suspension was injected into the mouse via right jugular vein as before. The mice were kept in 37° C. warming chamber for 30 min. For tail bleeding analysis, 1 cm length of tail from the tail-tip was surgically removed with a sharp scalpel, the transected tail was immediately immersed into warm saline (37° C.) and time for bleeding to stop (designated as 'bleeding time') was recorded. In our experience, the normal bleeding time for tail bleeding in this strain of mice is 100-120 s as shown in our revised FIG. 24C. Therefore any drastic variation of this bleeding time range was considered to be a systemic effect of SK on hemostasis (e.g., circulating plasminogen activation and systemic fibrinogenolysis). At the end of experiments, mice were euthanized by overdose of anesthesia.

Statistical Analysis

Statistical analysis of the PPFC-based in vitro binding and retention studies of heteromultivalent versus homomultivalent targeting of nanovesicles on thrombus-relevant platelet-rich surfaces was done using one-way ANOVA with the Tukey Method. For these studies, the quantitative analysis of surface-averaged fluorescence intensity (from platelet-bound particles on the test and control surfaces) was analyzed for multiple images (n=10 per test condition). FIG. 21 shows histogram data of these studies. The sPLA2-triggered drug release data was derived from n=3 studies and statistical analysis of this was done using a paired student's T-test between the groups. For the in vivo thrombotic occlusion time delay analysis, since we set up 30 min as one of the end points, the data do not have normal distribution. Therefore, we chose to report these results analyzed around the estimated mean (SE), and not by how much the sample differs from the sample mean (SD). For the tail-bleeding assay we used Mann-Whitney U test as this data is also not in a normal distribution. In all analyses, significance was considered to be $p<0.05$ Results In Vitro Evaluation of Thrombus-Targeting Capabilities of PMINs The peptides CGSSSGRGDSPA and CDAEWVDVS and the corresponding DSPE-PEG-peptide conjugates were characterized by mass spectrometry as shown in FIG. 20.

Representative cryo-TEM image of PMINs vesicles formed by combining DSPE-PEG-peptide molecules with distearyl phosphatidylcholine (DSPC) and cholesterol via self-assembly using the reverse phase evaporation and extrusion (RPEE) technique, is shown in FIG. 19, B1. Glass slides with adjacent circular areas of collagen-coated platelet-rich surface (simulating platelet-rich thrombi) and albumin-coated plateletpoor surface (control surface) were placed within the parallel plate chamber, and Rhodamine B (RhB)-labeled (red fluorescence) unmodified vesicles (no peptide decoration), or PMINs bearing both peptides (heteromultivalent at 1:1 ratio of 2.5 mol % each with respect to total lipid), or either peptide (homomultivalent at 2.5, 5 or 10 mol % with respect to total lipid) were flowed over the slides (schematic in FIG. 21A). Vesicle binding (RhB fluorescence) and retention was imaged under an inverted fluorescence microscope as described in the methods section. FIG. 21B shows representative fluorescence microscopy images of particle binding and retention on platelet-rich (or control) surfaces at high shear rate (4000 sec⁻1) conditions, while FIG. 21C shows quantitative results of homomultivalent versus heteromultivalent particle binding on plateletrich surfaces at low (300 sec$^{-1}$) and high (4000 sec$^{-1}$) shear flow conditions. Additional results show representative fluorescence images of vesicle binding (30 min time point) and retention (45 min time point) at low (300 sec-1), medium (2000 sec$^{-1}$) and high (4000 sec$^{-1}$) shear rate conditions, for vesicles decorated homomultivalently (2.5 mol % or 5 mol % or 10 mol % single peptide) compared with PMINs bearing 5 mol % heteromultivalent decoration, along with the quantitative data from these studies for the mid-range (2000 sec$^{-1}$) shear rate condition. The corresponding Mean±SD data sets based on which such histograms of FIG. 21B were prepared. As evident from these results, homomultivalently decorated (singly modified) vesicles (bearing RGDpeptide only or EWVDV-peptide only) were able to substantially bind to activated platelet-rich surface and stay retained under flow conditions (B3: binding and B4: retention for RGD-decorated vesicles, B5: binding and B6: retention for EWVDV-decorated vesicles), but this capability was tremendously enhanced when the peptides decorations were combined on dual modified PMINs, i.e., heteromultivalent decoration (B7: binding, B8: retention). Representative images of particle fluorescence and corresponding platelet-rich surface brightfield images in the same field of view, for single targeted (homomultivalent) versus dual targeted (heteromultivalent) binding, confirming that the fluorescence indeed is from platelet-bound particles and that dual targeted particles have a significantly higher binding/retention capability on active platelets under a flow environment. This enhanced platelet-binding capability of heteromultivalently decorated PMINs was evident both at low (300 sec$^{-1}$) and high (4000 sec$^{-1}$) shear conditions even when the homomultivalent peptide decoration was increased to twice (10 mol %) that of heteromultivalent (5 mol % total) (quantitative histogram data in FIG. 21C). Related studies also indicated that within fixed total heteromultivalent modification (e.g. 5 mol % total peptide incorporation), modulating relative peptide ratios (80:20, 60:40, 50:50, 40:60, 20:80) may have some effect on binding, depending on the shear rate, but all vesicles with various ratios of heteromultivalent decoration compositions are capable of binding and retention on active platelet-coated surfaces substantially more than their homomultivalent (100:0 or 0:100) counterpart. As for the controls, unmodified vesicles showed minimal non-specific binding to platelet-rich collagen surface, as did the heteromultivalently decorated PMINs on platelet-poor albumin surface (FIG. 21B, B1 and B2). These results further confirm that combining PMP-inspired heteromultivalent platelet-binding mechanisms significantly enhances clot-binding specificity and clot-specific retention of PMINs under low-to-high shear flow environment.

Characterization of Lipase-Triggered Vesicle Degradation and Payload Release from PMINs The degradation mechanism of bis-BODIPY FL C11-PC lipid by sPAL2 is the same as that for DSPC lipid as shown in FIG. 22A and therefore the increase in BODIPY fluorescence emission is reflective of PMIN vesicle membrane degradation via sn-2 ester cleavage of DSPC by sPLA2. As shown in FIG. 22B, incubation of BODIPY-labeled PMINs with sPLA2 resulted in substantial enhancement of BODIPY fluorescence emission within 30 min period, indicating substantial membrane degradation of the PMINs by the enzyme. Streptokinase (SK) was encapsulated in these PMINs as described in methods, the vesicles were purified from free (un-encapsulated) SK by using Amicon ultracentrifugal filters and the isolated vesicles were treated with Triton X to exhaustively release the loaded SK. The SK thus released was quantified using an SK-specific chromogenic assay and encapsulation efficiency (EE) of SK for various batches of PMIN preparation was thus assessed. As shown in FIG. 22C, the EE for SK in the PMINs was found to be approximately 40% for the various batches. Following this, temporal release of SK from the PMINs with or without sPLA2 exposure was monitored over 10 h. Exposure of SK-loaded PMINs to sPLA2 resulted in significant enhancement of the SK release levels, compared to that without sPLA2 exposure (FIG. 22D). Within the first 2 h, the percent (%) release of SK from the PMINs was about 4 times more with sPLA2 exposure than without the enzyme exposure. Altogether, these results establish the capability of the PMINs to be amenable to clot-relevant enzyme responsive membrane destabilization and resultant release of encapsulated drug payload.

In Vitro Evaluation of Targeted Thrombolytic Capacity of PMINs

The synergistic validation of platelet-rich thrombus anchorage capability and the lipase-triggered thrombolytic drug release capability of the PMINs, led to the integration of these capabilities to create SK-loaded clot-targeted enzyme-responsive PMINs and their evaluation for targeted thrombolytic (fibrinolytic) capability in vitro. For this, platelet-rich thrombi was created on collagencoated circular regions on glass microscope slides as before but with PRP containing AlexaFluor 488-labeled (green fluorescent) fibrinogen (6% v/v of 1.5 mg/mL), such that the platelet-rich fibrin clot on the collagen-coated region could be visualized for green fluorescence under an inverted fluorescence microscope (see Methods for details). SK-loaded, platelet-targeted (or untargeted) RhB-labeled (red fluorescent) PMINs (or control vesicles) were flowed over these green fluorescent clots in the PPFC system in a closed loop along with sPLA2, and the vesicles and clots were imaged under an inverted fluorescence microscope. FIG. 23A shows the schematic of this set-up where the fibrinolytic effect was assessed by imaging the green fluorescent clot with red fluorescent vesicles binding to it and monitoring the loss of green fluorescence (indicating fibrinolysis) and red fluorescence (indicating vesicle degradation) in the field of view. FIG. 23B shows representative fluorescent images from these studies captured over 60 min flow period for the groups 'Saline only' treatment, 'Free SK' treatment, 'SK-loaded untargeted vesicles+sPLA2', 'SK-loaded thrombustargeted vesicles (PMINs) without sPLA2', and 'SK-loaded thrombus-targeted PMINs with sPLA2'. Please note that for the first two groups, representative images have only clot fluorescence (green) since no red fluorescent particles are involved in these two groups of studies. For the next three groups, since untargeted or targeted vesicles are involved in the studies, the top row shows the clot (green) fluorescence while the bottom row shows the particle (red) fluorescence in the same field of view. Also please note that the fibrin morphology (shown by green fluorescence) has some variability between the various groups compared, but the starting condition in all groups shows a green fluorescent dense fibrin covered surface. As evident from the images, free saline is unable to cause any clot lysis (no change in green clot fluorescence) while free SK effectively lyses clots within 15 min of flow (significant loss of green fluorescence). For the vesicle treated groups, SK-loaded untargeted vesicles are unable to bind to the clot and therefore unable to release any SK in presence of sPLA2, as evident from minimal loss of green clot fluorescence and minimal presence of bound red vesicles over the various time points spanning 60 min. For SK-loaded targeted PMINs, the vesicles are able to substantially bind to the clot as shown by the initial red fluorescence of the bound vesicles on the green clots in corresponding fields of view. However, without the presence of sPLA2, these vesicles do not degrade and release adequate amount of SK for clot lysis, as reflected by minimal loss of green fluorescence of clots (and red fluorescence of vesicles) over time. Some reduction in fluorescence is seen at longer time points (at 45 min and beyond), possibly because of low levels of vesicle destabilization and release of SK. In contrast, in presence of sPLA2, the SK-loaded thrombus-targeted PMINs degrade and release SK to render substantial thrombolysis, as evident from progressive decrease in green clot fluorescence (reflecting fibrin lysis) and red vesicle fluorescence (reflecting vesicle degradation). These studies confirm that the SK-loaded thrombus-targeted PMINs are capable of targeted anchorage to platelet-rich clots and release SK triggered by sPLA2-induced vesicle degradation for substantial clot lysis to levels comparable to free SK action.

In Vivo Evaluation of Clot-Targeted Binding Capacity of PMINs

Before carrying out binding studies in vivo, the effect of the peptides on quiescent mouse platelets were evaluated by adding them at concentrations equivalent to that used for PMINs to murine washed platelets with or without platelet agonist (ADP or collagen) and assessing the effect of the peptides on resting versus activated platelets via turbidimetric measurement on an aggregometer. The peptides were found to have no effect on quiescent platelets without agonist and the platelet aggregation was found to occur only when agonist was added. This indicated that the peptides (and hence peptidedecorated vesicles) themselves were not capable of activating and aggregating quiescent platelets, which can otherwise lead to systemic pro-thrombotic risks. The ferric chloride ($FeCl_3$)-induced carotid artery thrombosis model, viewed under intravital microscopy, was used to evaluate the binding of PMINs in vivo (setup shown in FIG. 24A). This model results in oxidative damage of arterial wall, leading to rapid development of platelet-rich occlusive thrombus, as confirmed by intra-vital microscopy (FIG. 24B, B1), as well as, by immunofluorescence-based histology of excised thrombosed artery (FIG. 24B, B2) and by scanning electron microscopy. In this model, action of fibrinolytic drug can inhibit clot formation and thereby delay the vessel occlusion, which is considered as a measure of thrombolytic efficacy. First, the ability of the PMINs to bind to the carotid artery thrombus was assessed by creating the thrombi in mouse carotid with non-fluorescent platelets, injecting RhB-labeled (red fluorescent) PMINs or unmodified vesicles intravenously (through the jugular) ~5 min after thrombus induction on the carotid, and imaging the binding of the PMINs (versus control unmodified vesicles) onto the platelet-rich thrombi. The studies confirmed that intravenously administered PMINs could actively bind and accumulate on the thrombus at significantly higher levels (FIG. 24C, C1) compared to unmodified vesicles (FIG. 24C, C2). This was further confirmed by excising the thrombosed artery, sectioning it longitudinally and imaging the luminal surface for vesicle (RhB) fluorescence. Ex vivo images of thrombi exposed to targeted PMINs showed significantly high levels of red fluorescent clusters (FIG. 24D, D1), compared to that exposed to unmodified vesicles (FIG. 24D, D2), indicating enhanced binding of the RhB-labeled PMINs to thrombus-associated active platelets. In additional experiments, after thrombus induction followed by targeted PMIN injection in the mice, the thrombi was observed for ~10 min under intravital microscopy, the mice were then euthanized, and the thrombosed carotid, non-thrombosed carotid, as well as, clearance organs (liver, lung, spleen and kidney) were excised, processed and analyzed for PMIN fluorescence to analyze percent localization (see Methods for experiment details). The targeted PMINs showed a significantly high level of localization (higher fluorescence intensity) in the thrombosed carotid compared to the non-thrombosed carotid. Also, during the 15 min circulation period of the experimental time window, only ~20% of the total injected dose were cleared cumulatively in the various clearance organs, with liver and spleen being the major organs of clearance. This is not surprising considering the fact that the PMINs are built upon a PEG-ylated liposome platform known to have low clearance and long circulation periods. These results therefore suggest that much of the injected PMINs might still be in the vascular compartment of the injected mice.

In Vivo Evaluation of Targeted Thrombolytic Capacity of PMINs

For targeted thrombolytic capacity assessment, Rhodamine 6G solution was first injected into the right jugular vein of the mouse to render direct fluorescent labeling of circulating platelets and the $FeCl_3$-induced thrombus was created in the carotid as before, such that the formation of the thrombus and extent of vessel occlusion can be observed directly by monitoring the fluorescent platelets in the artery with intra-vital microscopy. Blank (i.e., without SKloading) non-fluorescent PMINs or SK-loaded non-fluorescent PMINs or unmodified vesicles or free SK or saline only, was administered via the jugular vein (5 min after $FeCl_3$-induced thrombus induction) to observe thrombolytic effect (delay in thrombus growth and vessel occlusion) at the carotid site, in real time. FIG. 25A shows representative 2 min and 10 min post-injection time-point images for various treatment conditions, while FIG. 25B shows overall quantitative data (4 animals per group) from the various condition studies. Series of images from 2 min to 12 min time points for 'free SK' treatment group, 'SK-loaded targeted PMIN' treatment group and 'SK-loaded untargeted PMIN' treatment group. As evident from these results, administration of SK-loaded clot-targeted PMINs resulted in significant delay in vessel occlusion, at levels similar to that rendered by free SK administration. In comparison, administration of SK-loaded untargeted vesicles failed to render such delay in vessel occlusion and the vessel appeared majorly occluded by 12 min. These results indicate that the enhanced anchorage of SK loaded PMINs at the carotid thrombus site enabled enzyme triggered release of the encapsulated SK to cause targeted thrombolytic action and delay the vessel occlusion, while this was not the case for unmodified (untargeted) SK-loaded vesicles. Furthermore, targeted 'blank' PMINs (i.e. without SK loading) did not seem to have any thromboprotective effect by themselves. This is probably because of the fact that the multivalent decoration of plateletinteractive ligands on the PMIN surface possibly allows them to act as 'bridging' particles between active platelets, thereby supplementing the thrombotic aggregation. This effect is potentially offset when thrombolytic drug (e.g., SK) is released from the PMINs and hence the delay in vessel occlusion is essentially an effect of targeted delivery and release of PMIN-encapsulated SK. In separate experiments, free SK or PMIN-encapsulated SK was intravenously administered in mice and 30 min post-administration the effect of SK on systemic hemostatic capability (i.e., off-target systemic effect) was assessed by tail-vein bleeding time measurement. Free SK administration resulted in significant prolongation of tail bleeding time (indicating systemic off-target fibrinogenolysis) compared to normal (no treatment) mice, while administration of PMINencapsulated SK had minimal effect on bleeding time (FIG. 25C). Altogether these results establish that the SK-loaded enzymeresponsive PMINs can render thrombolysis almost as effectively as free SK but in a targeted fashion, while minimizing off-target effects on systemic hemostatic capabilities.

This example describes the development, characterization and in vitro, as well as, in vivo evaluation of a platelet microparticle inspired nanovesicle (PMIN) system for active platelet-directed thrombus site-selective delivery and enzyme-triggered release of thrombolytic drug for targeted fibrinolytic action while minimizing off-target systemic side-effects. The results described herein establish the capability of the PMINs to actively anchor onto platelet-rich thrombi under flow, allow lipase triggered vesicle degradation for encapsulated payload release and thereby allow targeted fibrinolytic action at the clot site. Also, per our aggregometry studies, the peptide ligands themselves do not activate and aggregate quiescent platelets, indicating that these PMINs should have minimal interaction with circulating resting platelets and hence minimal systemic prothrombotic risk. Our in vivo results further validate that these enzyme-responsive PMINs can render targeted thrombolysis effectively without affecting systemic hemostatic capabilities. Besides targeted thrombolysis, the PMIN system can also become an efficient delivery platform for other therapeutic payloads (e.g. anticoagulant and anti-inflammatory drugs) in the vascular compartment, for potential site-selective treatment of vaso-occlusive pathologies in acute myocardial infarction, ischemic stroke, pulmonary embolism, deep vein thrombosis, peripheral arterial occlusion and indwelling catheter occlusions.

Example 5

The SynthoPlate nanotechnology can act as a synthetic intravenous 'platelet surrogate' to render rapid targeted hemostasis at acute injury sites to mitigate hemorrhagic shock-induced exacerbating effects in traumatic brain injury+hemorrhagic shock 'TBI+HS' and the technology can be further refined into a braintargeted drug delivery system for localizing neuro-protective/regenerative therapeutic agents selectively at sites of TBI, for pre-hospital, en route and long term precision trauma care in 'TBI+HS'.

Targeted Hemostatic Benefit of SynthoPlate™ in a Swine Model of TBI+HS

A porcine model of 'TBI+HS' multisystem trauma is used to evaluate the impact of SynthoPlate on hemodynamics, coagulopathy, cerebral injury, and neurologic recovery. Animals are instrumented with peripheral and pulmonary artery catheters for 'precision monitoring' of hemodynamics (cardiac output, blood pressure, systemic and pulmonary vascular resistance) and a Raumedic catheter is placed to monitor intracranial pressure, cerebral perfusion pressure and brain tissue oxygenation. TBI is induced by controlled cortical injury followed by pressure-controlled hemorrhagic shock induced via controlled venous injury and bleed. Resuscitation involves 'precision monitoring'-guided doses of various treatment groups: crystalloid, crystalloid+SynthoPlate, whole blood, RBCs+plasma, or RBC+plasma+SynthoPlate with resuscitation using 'precision monitoring'-guided doses of various treatment groups: crystalloid, crystalloid+SynthoPlate, whole blood, RBCs, plasma, or RBC+plasma+SynthoPlate. Hemostatic outcomes is assessed with viscoelastic coagulation testing via rotational thromboelastometry (ROTEM), platelet aggregometry, blood loss analysis, arterial pressure stabilization and other vitals monitoring, and tissue histology analyses at bleeding site post-hemostasis. Neurologic outcome assessment includes neuron specific enolase as a serum biomarker of injury, MRI for extent of injury, and a neurologic exam within 7 days of injury. SynthoPlate at precisely monitored intravenous doses can efficiently act as a 'platelet surrogate' to site-specifically augment physiologic coagulation mechanisms to render rapid hemostasis and mitigate HS, thereby improving neurologic outcomes as assessed by a porcine neurologic severity score and MRI measurement of cerebral injury. To this end, a dosage protocol for SynthoPlate in swine model of 'TBI+HS' is established and SynthoPlate dose evaluation studies in hemostatic+neurologic benefit are started. In addition, the effect of SynthoPlate dose vs other (standard) resuscitation fluids in 'TBI+HS' is compared. At fixed dose SynthoPlate vs fluid vs RBC vs plasma vs whole blood is compared, SynthoPlate dose combination with other resuscitative fluids and blood are studied, and SP is established as a viable I.V. hemostatic platelet surrogate for field use in 'TBI+HS'.

Surface-Refined SynthoPlate™ Platform for TBI-Targeted Delivery of Cerebrolysin for Augmented Neuroprotection.

The SynthoPlate vesicle design is refined to incorporate the TBI-targeted peptide CAQK on the surface, so as to create a TBI-targeted nanovehicle platform. Within this nanoparticle, Cerebrolysin is loaded to create a TBI-directed Cerebrolysin nanoformulation for precisely targeted delivery and sustained drug action at the TBI site. This unique TBI-targeted nanomedicine system is optimized for TBI-targeting capabilities and drug loading/release kinetics. The optimized drug-loaded formulation is subsequently evaluated in the pig model of TBI for therapeutic efficacy and neurologic outcome evaluation. The end goal is to establish that the Cerebrolysin-loaded CAQKdecorated nanomedicine vesicles are capable of precisely recruiting to sites of brain injury in TBI and releasing the drug payload for precise spatio-temporally regulated neuroprotective (and possibly neuro-regenerative) by MRI assessment of brain injury and neurologic severity score. To this end, CAQK-decorated lipid nanovesicles are manufactured and characterized by refining Synthoplate-type vesicle platform surface with peptide CAQK. In addition, TBI-Targeted Drug Delivery Nanomedicine is evaluated by evaluating targeted binding efficacy CAQK-decorated nanovesicles at TBI site by loading nanovesicle with Cerebrolysin and testing encapsulation and release kinetics, and evaluating single dose delivery of Cerebrolysin-loaded CAQK-decorated lipidic nanomedicine system in swine model of TBI and assess neurologic outcome.

Research Design and Methods

The manufacture of SynthoPlate hemostatic nanoparticle formulations, as well as, the SynthoPlate-analogous refined design of CAQK-decorated Cerebrolysin-loaded lipidic vesicle nanoformulations, are done at scales needed for the pig model studies, characterize their size, stability, loading/release kinetics and bioactivities in vitro using appropriate instrumentation, biochemical, aggregometry and thromboelastometric assays. Manufactured particles and nanoformulations are provided for all aspects of in vivo studies in 'TBI+HS' models.

Targeted hemostatic benefit of SynthoPlate™ in a swine model of TBI+HS

Since the application of SynthoPlate™ is in emergency hemostatic treatment of traumatic bleeding in 'TBI+HS', we first carry out 60 min time period studies on pharmacokinetics, biodistribution and systemic safety of SynthoPlate™ administered in healthy pigs without injury. Pigs are injected with a bolus (full dose injected in <1 min) versus infusion (full dose injected over period of 10 min) of various SynthoPlate™ doses followed by 450 ml saline flush. For the SynthoPlate™ suspensions, both normal (0.9%) and hypertonic (3%) saline suspensions are studied, given the known benefit of 3% saline following acute TBI. This will allow us to establish a dose window, as well as, a dosage protocol within which SynthoPlate can be safely administered without acute response in pigs. These parameters are used subsequently to evaluate effect of SynthoPlate dosing in pigs with 'TBI+HS'.

Manufacture of SynthoPlate

We have optimized the compositional design of the SynthoPlate vesicle, where a total of 5 mol % incorporation of peptides (1.25 mol % VBP, 1.25 mol % CBP and 2.5 mol % FMP with respect to total lipid) results in a theoretical estimate of ~50,000 ligands decorations on the surface per vesicle, which is more than sufficient to render platelet-mimetic pro-adhesive and pro-aggregatory functions important in hemostasis. Therefore for all SynthoPlate™ systems used we utilize 1.25 mol % of DSPE-PEG-VBP, 1.25 mol % of DSPE-PEG-CBP, 2.5 mol % of DSPE-PEG-FMP, 5 mol % of DSPE-PEG, 40 mol % Cholesterol, 49 mol % DSPC and 1 mol % DSPEE-PEG-Rhodamine B (red fluorescent probe), to make self-assembled liposomal vesicles using the reverse phase evaporation extrusion technique. The DSPC content is to maintain vesicle stability at room temperature (DSPC melting temperature is ~55° C.) in storage, as well as, to impart the property of secreted Phospholipase A2 (sPLA2)-triggered membrane destabilization at the traumatic injury site for ultimate biodegradation and safe elimination of SynthoPlate components. The rationale for this biodegradation mechanism is based on the fact that activated platelets and leukocytes (phenotypic hallmarks of bleeding, vascular injury and inflammation) upregulate the secretion of enzyme PLA2, which can be leveraged as a stimulus for enzyme-triggered biodegradation. The cholesterol content in SynthoPlate is to maintain membrane integrity of the vesicle during in vivo circulation, and the PEG linker (with molecule weight 2000 Da) is to maintain reasonable circulation lifetime of the vesicles by minimizing rapid opsonization and macrophagic uptake. SynthoPlate vesicles thus prepared are stored in saline suspensions or as lyophilized powder (reconstitutable in saline prior to I.V.-administration).

Assessment of Dose Window and Systemic Safety

For a 30 kg pig, native platelet concentration is ~2-4×$10^{11}$ platelets per liter. The diameter of our SynthoPlate particles is 3 orders of magnitude smaller (i.e. nano-scale) compared to platelets (which is micro-scale). Therefore, we test SynthoPlate™ doses 3 orders of magnitude higher than native platelet concentration (i.e. in the order ~$10^{11}$ particles per ml instead of per liter) as our baseline dose concentration and then test 3 log doses below this and 3 log doses above this (i.e., total 7 dose values), as our starting evaluation metric. As mentioned previously, each dose is suspended in 0.9% saline or 3% saline, to evaluate the two tonicity conditions, and injected at −1.5 ml/kg volume followed by 450 ml saline flush. Upon bolus (<1 min) or infusion (over 10 min) administration of SynthoPlate in uninjured pigs within the dose windows stated above, the vitals, including arterial blood pressure, heart rate, $SpO_2$, $CO_2$, and temperature are monitored every 30 seconds for the first 10 minutes, then every minute for the next 20 minutes, then every 5 minutes for the last 30 minutes for anomalies that could be indicative of systemic risk. The skin is monitored for the presence of urticaria, flushing, or other types of rash that could be suggestive of an immune response. Blood samples are drawn at baseline, 5 minutes, 15 minutes, 30 minutes, and 1 hour to track the pigs' physiological response including arterial blood gas, and complete blood count. The blood is also used to evaluate systemic pro-thrombotic risk via coagulation panel (PT and aPTT), ROTEM, D-dimer assay and impedance aggregometry. The blood is also used to run assays to detect complement activation components as markers of the pigs' immune response on SynthoPlate dosage. Specifically, we run immunoassays that will measure and quantify spectrophotometrically the complement components C3b, C5a and immunoglobulin. 1 hr after SynthoPlate administration, pigs are euthanized and the major organs (heart, lungs, liver, spleen, kidneys, brain, and blood) are harvested. Histology (H&E staining and fibrin-specific immunostaining) is performed on these organs to monitor for the presence of microvascular thrombi.

Number of Animals

For these studies we use a sample size of 5 animals per group, with calculations based on p=0.05, power 0.9, assuming a standard deviation equal to half of the difference in our means. Groups include 7 different SynthoPlate concentrations and suspended in 0.9% or 3% saline, thereby totaling 14 groups. Therefore we estimate use of 70 pigs for dose and systemic safety studies.

Detailed Description of the 'TBI+HS' Model

Pigs are chosen as the model in order to achieve the desired neurologic benefit endpoint in a large animal model where physiologic changes after hemorrhage are similar to that seen in humans. Also, pigs represent a well-validated gyrencephalic species for the study of 'TBI' as well as 'TBI+HS'. In addition, this pig injury model allows for neurologic assessment by MRI, which can provide precision assessment of pathology as well as therapeutic outcomes. In the studies, pigs are subjected to TBI, HS and post-injury resuscitation. Each pig is anesthetized and endotracheally intubated. Central venous access and femoral arterial access is obtained in a supine position via cutdown and vessel cannulation (FIG. 26). Animals are then placed in a prone position on a platform with stereotaxic frame. A 2 cm right and 1 cm left craniotomy is created to expose the dura. The craniotomies are centered 16 mm anterior to the coronal suture and 10 mm lateral to the midline sagittal suture. An intracranial pressure monitor is placed through the left craniotomy. FIG. 26. Schematic of porcine 'TBI+HS' model Traumatic brain injury is induced by controlled cortical injury through the right craniotomy with a 15 mm diameter impactor at 4 meters/second, with 100 millisecond dwell time to a 12 mm depth onto the exposed dura and underlying cerebral parenchyma. Pigs then undergo a controlled hemorrhage induced by the removal of 100 mL/minute of blood via the central venous access to a goal of 40% of predicted intravascular volume. Following blood removal, the pig is maintained in a shock state with a target mean arterial pressure (MAP) of 35±5 mmHg (removing blood if the MAP goes above target range or infusing intravenous fluid if it is below the target range) for 30 min, simulating the shock that occurs in a clinical trauma prior to administration of medical care. Thus, the 'TBI+HS' insult is rendered in the model.

SynthoPlate Treatment of the 'TBI+HS' Scenario

Upon inducing the 'TBI+HS' insult, pigs are administered intravenously with the following groups: 0.9% saline+control particles, 0.9% saline+SynthoPlate™, 3% saline+control particles, 3% saline+SynthoPlate, autologous shed (whole) blood+control particles, autologous shed (whole) blood+SynthoPlate, banked RBCs+plasma with control particles, banked RBCs+plasma with SynthoPlate. The initial dose of SynthoPlate is $2.5 \times 10^{11}$ particles/ml given at ~1.5 ml/Kg followed by 450 ml saline flush, as this dose gave promising data in our preliminary studies in femoral artery bleeding model in pigs. In subsequent experiments the dose is varied between 3 logs down 3 logs up as needed, dictated by our safety studies described previously. If the pig decompensates hemodynamically following the specified resuscitation protocols, the pig is resuscitated with a 1:1 volume of lactated Ringer's to shed blood volume. Following this resuscitation, further resuscitation with lactated Ringer's is based upon comparison to baseline MAP and stroke volume variation determination from the indwelling Swan-Ganz catheter. The pigs are then observed for 4 hours and several parameters will be assessed to evaluate hemostatic efficacy and neurologic benefit of SynthoPlate, as described below.

Assessment of Hemostatic Efficacy of SynthoPlate-Based Resuscitation

Blood is drawn at baseline, post-TBI/pre-HS, every 10 min in hemorrhagic shock, every 30 min for 2 hours after providing resuscitation, and then hourly until completion of the four hour observation period. These blood samples are used to assess hemostasis and coagulation status of the pig utilizing prothrombin time, rotational thromboelastometry (ROTEM), impedance aggregometry, as well as biochemical assays for soluble P-selectin, VWF, soluble D-dimer and soluble CD40L. Thus this spectrum of measurements provides a comprehensive assessment of not only the hemostasis/coagulation status, but also of pro-inflammatory pathology if present.

Assessment of Neurologic Benefit of Hemorrhage Control with SynthoPlate™ in 'TBI+HS'

Blood will be drawn at baseline, post-TBI/pre-HS, every 10 min in hemorrhagic shock, every 30 min for 2 hours after resuscitation is provided, then hourly until completion of the 4 hour observation period. These blood samples are used to assess neurologic injury by measuring serum levels of neuron specific enolase (NSE). Hypotension exacerbates the neuronal injury incurred after TBI, which can be followed with serum sampling of NSE. SynthoPlate efficacy would be established by a reduction of cerebral NSE. Mean arterial, intracranial, and cerebral perfusion pressures are monitored from the induction of TBI through the 4 hour observation period. Brain tissue oxygenation in the cerebral hemisphere contralateral to the injured hemisphere are also continuously monitored. In addition, immediate post-mortem MRIs are obtained to assess neurologic injury using T2 sequences to determine tissue water content, cerebral edema in the injured cortex and penumbra surrounding the injured area, and determine the volume of injured cerebral tissue.

Histologic Analysis of Hemostatic and Neurologic Response

Following post-mortem MRI, brains are sliced in a standardized mold. Brain slices are further assessed for a hemostatic response using Carstair's stain and anti-thrombocyte specific immunostaining to determine the distribution of intracerebral microvascular thrombosis. Immunostaining and fluorescence microscopy analyses are performed to determine the distribution of SynthoPlate at hemostatic clot site of injured vessel versus normal uninjured vessel, typical clearance organs (liver, lung, kidney, spleen), and throughout the injured and uninjured areas of the brain. Based on the design of SynthoPlate we anticipate that it will preferentially localize at sites of macro and microvascular bleeding to leverage, mimic and amplify physiologic mechanisms of coagulation to enhance hemostasis, and excess SynthoPlate will be cleared predominantly in the liver via macrophagic process. Alternating slices of the brain are also assessed via triphenyl tetrazolium chloride (TTC) to differentiate between metabolically active and inactive (ischemic) tissues. Treatment efficacy is indicated by a reduction of intracerebral microvascular thrombosis by Carstair's stain and anti-thrombocyte stain. In addition, reduction in the volume of TTC stain indicates a macroscopic decrease in cerebral injury size.

Number of Animals/Data Analysis/Statistical Analysis

For these studies a sample size of 5 animals per group is used, with calculations based on p=0.05, power 0.9, assuming a standard deviation equal to half of the difference in our means. Our anticipated groups would be 0.9% saline+control particles, 0.9% saline+SynthoPlate™, 3% saline+control particles, 3% saline+SynthoPlate™, autologous shed (whole) blood, autologous shed (whole) blood+SynthoPlate™, banked RBCs+plasma with control particles, banked RBCs+plasma with SynthoPlate™, each 'SynthoPlate™' group testing at least two doses (one low, one high). Therefore we estimate 12 groups and an estimated total of 60 pigs for this resuscitation study phase. Statistical analysis is done by ANOVA.

Evaluation of Surface-Refined SynthoPlate™ Platform for TBI-Targeted Delivery of Cerebrolysin for Augmented Neuroprotection A significant research focus is currently being directed at effective pharmacological strategies for treating TBI and TBI-associated symptoms. There needs to be robust research of pharmacotherapeutic agents in human anatomy-relevant preclinical standardized TBI models, where predictive and pharmacodynamic biomarkers of therapeutic response (and hence target patient selection) can be precisely monitored, e.g., via biochemical monitoring of oxidative stress, inflammation, and neuronal integrity, and high resolution imaging-assisted monitoring of cellular and tissue function (e.g., using PET and MRI). The pharmacotherapeutic strategies and their response analysis also need to incorporate consideration of the multifactorial nature of TBI pathology in acute phases and chronic phases, in terms of immediate and longterm effects. Within this framework, we postulate that (i) due to the complex multifactorial pathology of 'TBI+HS', pharmacotherapeutic intervention with multifunctional pleiotropic drugs may have significant benefit in neuroprotective and regenerative mitigation of TBI, and (ii) site-selective delivery of the drug to TBI site via molecularly targeted nanomedicine platforms can allow precise spatio-temporally controlled therapy with minimal systemic off-target drug loss and side-effects. Built on this rationale, we investigate Cerebrolysin as a candidate drug and the peptide sequence CAQK (SEQ ID NO:6) as a molecular zipcode to target drug-loaded refined SynthoPlate-analogous lipid nanovesicles to TBI site. Various neurotrophic factors such as nerve growth factor (NGF), brain-derived neurotrophic factor (BDNF), ciliary neurotrophic factor (CNTF), glial cell line derived neurotrophic factor (GDNF) etc. are present in the CNS, that are required for the survival and proper functioning of neurons. Cerebrolysin is a parenterally administered, porcine brain-derived peptide preparation that contains active fragments of many of these neurotrophic factors, and therefore it has pharmacodynamic properties similar to those of endogenous neurotrophic factors. In recent years, a large number of in vitro studies, in vivo studies in pre-clinical animal models and several clinical studies in Europe have established the therapeutic promise of Cerebrolysin in neuroprotective maintenance of neuronal viability after CNS injury, synaptic modulation to improve integrity of neuronal circuits, and rendering short-to-long term neuro-generative effects in diseases like multiple sclerosis, Parkinson's disease, Alzheimer's disease, dementia, and acute or chronic stroke. The effect of this therapeutic peptide cocktail has not been studied in pre-clinical gyrencephalic models of 'TBI+HS'. Therefore, we aim to evaluate its therapeutic effect in a pig model of 'TBI+HS' to provide new insight on its neuroprotective and neuro-generative capacities. The other unique component of our method is to render spatio-temporally directed delivery of Cerebrolysin packaged within a TBI-targeted nanomedicine platform. For this purpose, we use a SynthoPlate-analogous lipid nanovesicle surface-decorated with the peptide sequence CAQK. This short peptide sequence was recently identified by in vivo phage display screening in mice with acute brain injury, and was found to have the capability to bind to both mouse and human brain specifically to extracellular matrix domains (e.g., perineuronal nets or PNNs) rich in chondroitin sulfate proteoglycans (CSPGs) that are known to be upregulated at TBI sites. The CAQK peptide, when conjugated to fluorescent labels, was capable of enhancing the localization (and hence imaging) of the label to acute brain injury site, and when conjugated to oligonucleotide-loaded (e.g., siRNA) silica nanoparticle surface, was capable to render site-selective response at the brain injury site. We package Cerebrolysin within CAQK-decorated lipidic nanovesicles for targeted delivery and spatio-temporally directed action at the TBI site, evaluated in pig models.

Figure 27:
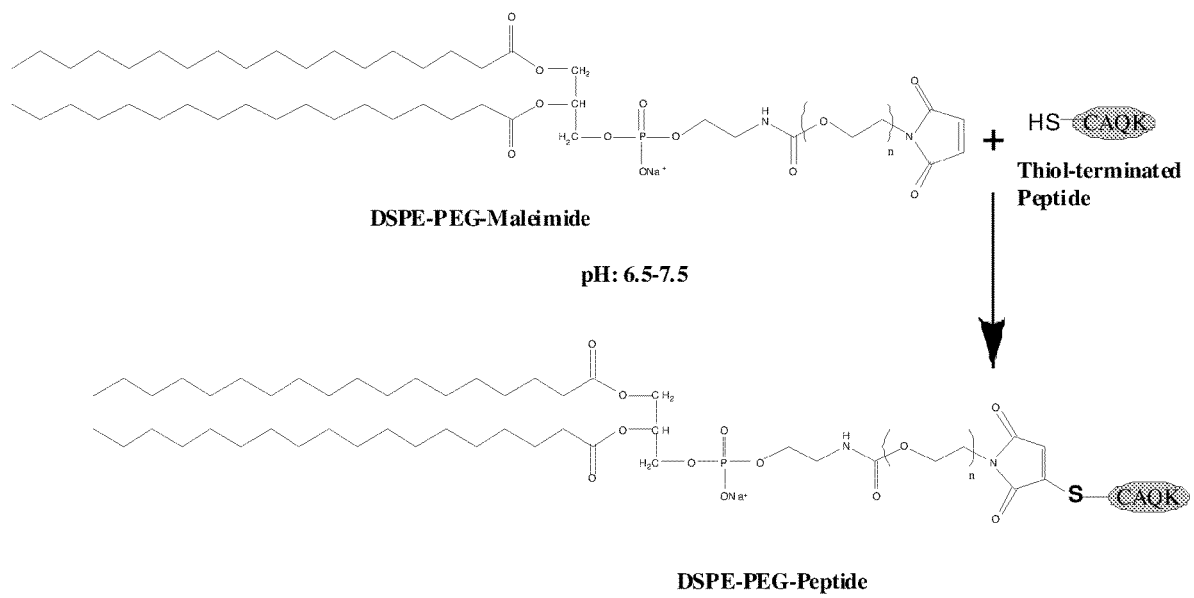
FIG. 27 illustrates a reaction schematic for conjugating CAQK peptide to DSPE lipid.
Figure 28:
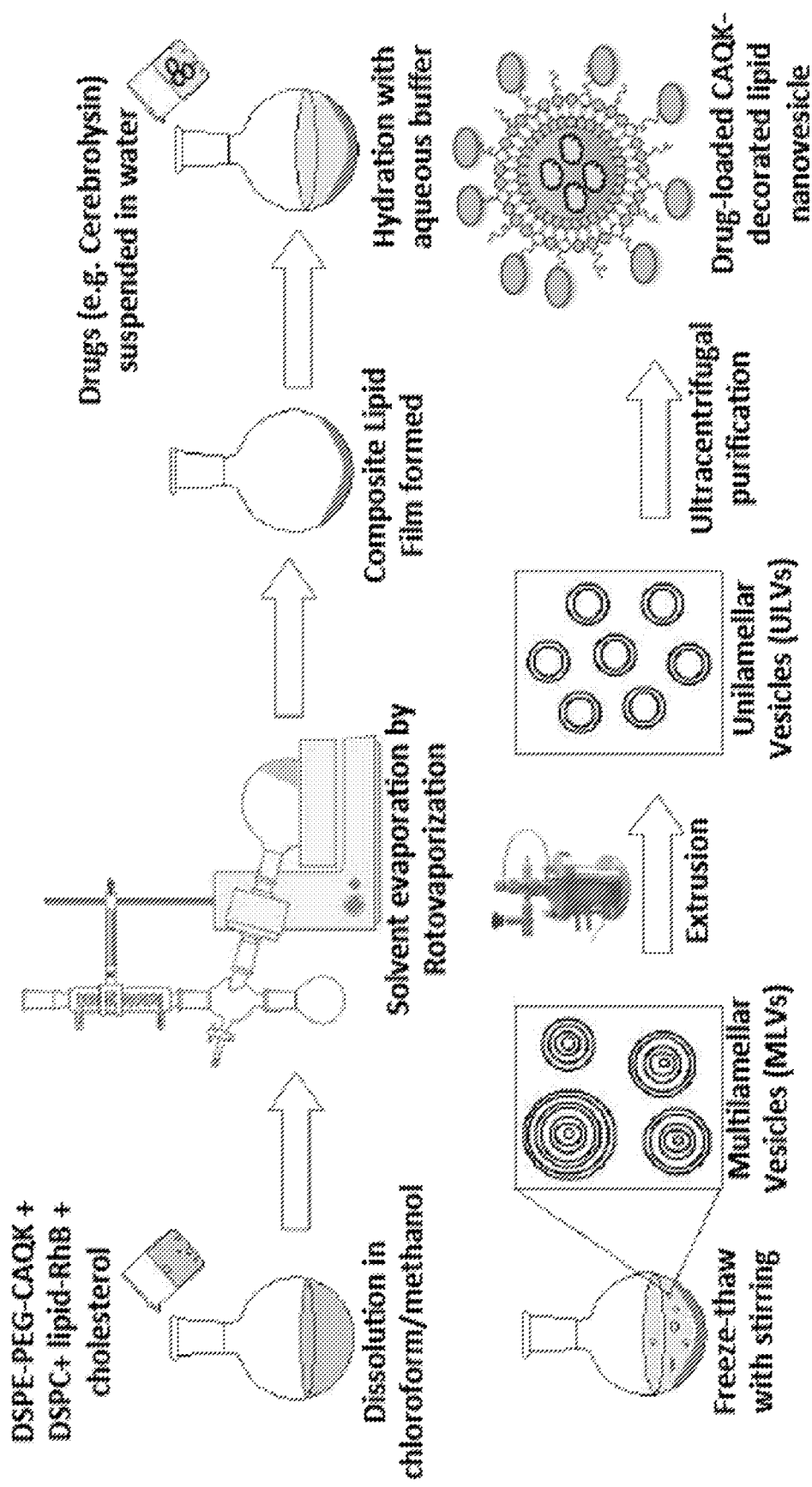
FIG. 28 illustrates a schematic showing a reverse phase evaporation extrusion (RPEE) process for manufacturing peptide-decorated drug-loaded lipid nanovesicles.

Synthesis and Characterization of CAQK-Decorated SynthoPlate™-Analogous Lipid Nanovesicle The sulfhydryl (—SH) group in the terminal Cysteine residue of the CAQK peptide is utilized to conjugate it via thioether linkage chemistry to the maleimide (Mal) group at the terminus of a polyethylene glycol-modified distearyl phosphatidyl ethanolamine lipid molecule (DSPE-PEG-Mal). Maleimide group reacts specifically with sulfhydryl groups when the pH of the reaction mixture is between pH 6.5 and 7.5, forming a stable thioether linkage. The reaction schematic is shown in FIG. 27. The resultant DSPE-PEG-CAQK conjugate at 5 mol % is integrated with SynthoPlate™-relevant structural lipid distearyl phopshatidyl choline (DSPC) at 50 mol %, cholesterol at 40 mol % and the lipophilic fluorescent probe Rhodamine-B-dihexadecanoyl-snglycero-3-phosphoethanolamine (DHPERhB, orange red emission), to manufacture CAQK-decorated lipid nanovesicles via reverse phase evaporation and extrusion (RPEE) technique, as shown in FIG. 28. Resultant vesicles are characterized for their size distribution and stability by Dynamic Light Scattering (DLS) and cryo-Transmission Electron Microscopy (cryo-TEM). The vesicles, manufactured batch-to-batch, are further subjected to a variety of ambient conditions: acidic and alkaline pH, normal vs hypertonic saline (0.9% and 3%), storage temperature (4° C., 25° C., 37° C. and 50° C.), exposure to serum, and lyophilization/reconstitution, and vesicle stability and integrity are assessed by DLS and cryo-TEM. The overall goal of these characterization studies is to establish the manufacturing reproducibility and variable condition stability of the nanovesicles, which will be important for subsequent therapeutic nanoformulation.

Loading and Release Kinetics Studies of Cerebrolysin from CAQK-Loaded Nanovesicles Cerebrolysin is obtained commercially from EVER Neuro Pharma GmbH (Austria). This pleiotropic cocktail of polypeptides and growth factors is available in a soluble form and hence can be conveniently loaded within the aqueous core of the above-described lipid vesicles. For this purpose, the Cerebrolysin suspension is mixed with the hydration buffer during the lipid layer hydration step of RPEE process. The commercially obtained Cerebrolysin is run through UV-Vis spectrophotometer to establish its absorption spectra characteristics and thus a calibration curve that quantitatively correlates its absorption to its concentration. Following that, Cerebrolysin-loaded nanovesicles is ultracentrifuged (at 500,000 g) to pellet the drug-loaded vesicles at the bottom of the tube and thus separate them from the un-encapsulated (i.e. free) Cerebrolysin. The supernatant is analyzed by UV-Vis spectrophotometry to quantify the un-encapsulated amount (based on the calibration curve established as described above). The pelleted vesicles is then exposed to Triton X buffer to completely destabilize the vesicles and thus exhaustively release the 'encapsulated' Cerebrolysin, which are similarly quantified by UV-Vis spectrophotometry. Thus, the 'encapsulated' and 'un-encapsulated' values provide the basis for calculating the loading capacity of Cerebrolysin within these CAQK-decorated lipid nanovesicles. This analysis is done for at least 5 batches of preparation to ensure reproducibility and consistency of this Cerebrolysin loading capability in the CAQK decorated lipid nanovesicles. In our experience, the encapsulation efficiency of water-soluble drugs in vesicles can vary from 40-70%. Therefore, we consider an average encapsulation of ~50% as success.

Therapeutic Feasibility Studies of Cerebrolysin Nanoformulation in Targeted Treatment of TBI in Pigs Since a brain-targeted Cerebrolysin nanoformulation within CAQK-targeted lipid vesicles has never been studied for precision treatment of TBI, for the current proposal we will limit our evaluations only to a porcine model of TBI only (not 'TBI+HS'), so as to not confound potential effects of Cerebrolysin with blood productbased resuscitation resuscitation. We initially utilize a porcine intravenous (through jugular) dosing of 1 mL/kg followed by 10 mL saline flush administered over a 10-minute period, starting at 30 minutes after TBI. Based upon neurologic outcome assessment, our dosage protocol remains flexible to further consider doubling the groups of animals to determine earlier vs later timing of the Cerebrolysin if needed. Vital signs and intracranial pressure, cerebral perfusion pressure, and cerebral tissue oxygenation are measured during the induction of TBI, during the nanomedicine infusion, and for 4 hours following the infusion to assess physiologic response to the infusion. Neurological outcomes include post-mortem MRI at 4 hours after Cerebrolysin suspension administration and another experimental group to survive to 7 days, then undergo MRI followed by euthanasia. Brain histological assessment is performed with H&E, Fluorojade-C for neurodegeneration, and immunostaining for tau phosphorylation and staining for Cerebrolysin-loaded vesicles in the brain at both time points. Benefit is determined by a reduction in Fluorojade-C indicated neurodegeneration as well as a reduction in the accumulation of tau protein and injury-related edema on T2 MRI sequences. Labeled Cerebrolysin-loaded nanovesicles are also assessed histologically for their distribution within the injured cerebral hemisphere and uninjured cerebral hemisphere. Additional tissue is harvested from the lung, liver, and spleen to further determine the targeting specificity of nanovesicles for the injured cerebral tissue.

Number of Animals

For these studies a sample size of 10 animals per group is used (5 for immediate euthanasia and brain assessment and 5 for 7 day post-TBI survival and neurologic recovery assessment), with calculations based on p=0.05, power 0.9, assuming a standard deviation equal to half of the difference in our means. Groups include TBI without HS+Cerebrolysin/0.9% saline, TBI without HS+Cerebrolysin/3% saline, TBI+HS+Cerebrolysin/0.9% saline, TBI+HS+Cerebrolysin/3% saline, TBI+HS+0.9% saline, TBI+HS+3% saline, TBI+HS+free Cerebrolysin (without nanovesicles), TBI+HS+nanovesicles without Cerebrolysin. Therefore we estimate 8 groups and an estimated total of 80 pigs for this neuroprotective study. Statistical analyses will be done by ANOVA.

Example 6

SynthoPlate Nanotechnology for Intravenous Hemostasis and Wound Healing in Prolonged Field Care The use of a synthetic platelet substitute, such as the SynthoPlate vesicle, with the ability to be localized at the wound site via intravenous as well as local (topical and intracavitary) application and respond to biochemical cues (e.g., enzymes) at the wound site for delivery of wound healing agents in a targeted fashion, can lead to a synthetic version of PRP therapy with enhanced precision and sustained spatio-temporal regulation of bioactivity.

As a feasibility demonstration, FIG. 29 shows the effect of enzyme phospholipase-triggered release of a model payload (in this case a thrombolytic drug Streptokinase) encapsulated within the SynthoPlate platform. As evident from the figure, encapsulation of the payload within the SynthoPlate platform itself allows for slow release kinetics (sustained release) over several hours (10 hrs in this case as shown by the red line), whereas the platform can be customized to destabilize (via vesicle membrane degradation) under action of specific enzymes (e.g., enzyme Phopspholipase A2 or PLA2 in this case) such that the payload can be released at a faster rate (e.g., 4 fold increase in release kinetics under PLA2 action, as shown by the blue line). Thus, the SynthoPlate system can be utilized as a triggerable drug release platform, e.g., for rapid release of an anti-fibrinolytic agent like TXA for augmentation of hemostatic clot or for slow release of anti-infective agents over sustained periods of time to facilitate wound bed protection and healing. The SynthoPlate particles can also be easily formed into a biodegradable gel or used directly as lyophilized powder, for topical use in the field.

It is believed that the SynthoPlate=technology can act as a synthetic platelet-mimetic intravenous hemostat and a platform for targeted delivery of TXA in the damage control resuscitation (DCR) management of hemorrhage in polytrauma, as well as, as a locally administrable controlled release platform for sustained release of anti-infective (and other bioactive) agents to facilitate improved early epithelialization (primary endpoint) in wound healing. We envision future expansion of this technology for intravascularly targeted delivery of a variety of therapeutic compounds (coagulation factors, anti-inflammatory agents, immunomodulatory agents etc.), as well as, a locally (topical and intracavitary) administrable platform for spatio-temporally regulated release of multiple growth factors in wound healing management. The hypothesis components are based on our preliminary findings that SynthoPlate can efficiently reduce bleeding time and blood volume loss in several small and large animal model pilot studies, and that the SynthoPlate vesicle design can be refined to incorporate lipidic and macromolecular components that allow temporal control over release kinetics of model payloads encapsulated within the vesicles.

Characterization of the Biodistribution, Systemic Risks and Immune Response of SynthoPlate™ in Pigs In translating any nanoparticle-based technology in large animals, it is critical to determine the pharmacokinetics and biodistribution of the particles, as well as, investigate systemic off-target effects if any. Here we investigate and mechanistically characterize dose-dependent complement-mediated immune response, leading to allergic reactions including elevated hear rate, respiratory distress, and development of skin rash responses (if present) in pigs, so that, if needed we can tailor the dosage and therapeutic protocols to mitigate such issues.

To this end, we will administer SynthoPlate suspension at various doses (max dose containing particle number equivalent to porcine normal platelet count and then lower doses up to 5 logs below) in total volume suspension of 50 ml via jugular vein catheter in pigs. Vitals (BP, CO2, sPO2, HR, temperature) will be closely monitored, and periodic blood draws will be performed over the course of 1 hour, to evaluate CBC and plasma levels of critical complement activation components (C3b and C5a). Based upon initial administration reaction, repeat dosing will be performed in selected group of pigs after 15 and 30 minutes. At the end of 1 hour, animals will be euthanized and harvested organs (lungs, liver, spleen, kidney, heart, brain, blood) will be analyzed for SynthoPlate™ sequestration (hence biodistribution). The blood will also be analyzed for signs of systemic pro-thrombotic effects (platelet activation levels by flow cytometry, systemic fibrinogen degradation effect by D-dimer assay and overall clotting characteristics by rotational thromboelastometry). Post-mortem histopathology of organs will also be used to assess organ-specific microvascular thrombi as a measure of systemic risk.

Altogether, we will characterize and mitigate immune response (if any) to SynthoPlate dosing, characterize biodistribution of SynthoPlate over time, characterize and mitigate systemic pro-thrombotic risks (if any) upon SynthoPlate administration, and by virtue of these findings, establish a safe dosing protocol for SynthoPlate in pigs.

We will also evaluate hemostatic efficacy of pristine SynthoPlate and TXA-loaded SynthoPlate in porcine model of polytrauma. A model of damage-control surgery following polytrauma will be implemented for large animal hemostatic validation of SynthoPlate™ transfusion. Pigs will be placed under anaesthesia with pulmonary artery catheter placement and femoral artery cannulation. Femur fracture, liver laceration and pulmonary contusion will be rendered on the anaesthetized pig. The femur fracture and pulmonary contusion will be produced by firing a bolt gun at the mid femur and 5th intercostal space. These procedures result in a highly repeatable type of closed fracture and contusion. A 10 cm liver laceration will be rendered surgically. The combination of these reproducible injuries results in significant trauma and hemorrhage, relevant to combat scenario. At this point, six treatment groups will be tested via intravenous administration: SynthoPlate vs Control particles (particles with no peptide modification) by themselves, or, SynthoPlate vs Control particles mixed together in suspension with TXA, or, SynthoPlate vs Control particles loaded in the vesicle core with TXA (encapsulated in vesicle core). TXA is already in military use as an intravenous anti-fibrinolytic agent to strengthen hemostatic clots and therefore the overarching theme of adding TXA (in suspension or in encapsulated form) to SynthoPlate treatment is to investigate potential synergistic benefit of the two mechanisms (SynthoPlate helping to form clot while TXA helping to stabilize/strengthen clot) to augment the hemostatic effect. If the animal drops its mean arterial pressure below 40 mmHg, we will resuscitate with lactated Ringer's (and the volume of resuscitation required will be quantified). After 30 minutes, we will pack the abdomen with a fixed number of weighed laparotomy pads and close the abdomen. At the end of 90 minutes, the pig will be resuscitated with crystalloid and the pigs will be then observed for up to 4 hours and sacrificed. Total blood loss will be quantified both in shed blood (via weighing laparotomy pads) and peritoneal lavage with calculation of hematocrit. Hemodynamic changes will be monitored throughout resuscitation. Post-euthanasia, tissues/organs will be harvested in a similar fashion as described above to analyze platelet and SynthoPlate sequestration as well as for assessment of validated measurements of organ injury.

We will demonstrate that post-injury SynthoPlate transfusion results in a significant reduction in blood loss following polytrauma, evaluate the potential synergistic effect of SynthoPlate and site-specific delivery of TXA on blood loss and hemodynamic changes after injury, and identify the effects of SynthoPlates ±TXA (additively mixed in suspension or encapsulated within vesicle) on organ injury and inflammation following trauma.

We will also evaluate the efficacy of SynthoPlate™ alone or in combination with Gentamicin to provide wound protection and improve re-epithelialization in porcine wound models. To explore and expand the applicability of SynthoPlate™ technology as a bioactive agent delivery platform in wound healing, we will test the feasibility and efficacy of SynthoPlate™ alone or SynthoPlate™ loaded with Gentamicin to (1) provide wound protection and decrease inflammation by limiting bacterial growth and migration of inflammatory markers in a deep partial-thickness burn model and (2) to improve re-epithelialization in a tangential excision wound model, both models in pigs. As a result of trauma, the human body attempts to protect itself from invading microorganisms and heal the injury by way of a complicated inflammatory response and cascade of events. Not uncommonly this inflammatory response is worsened with a concomitant infection. The development of an infection has profound effects on wound healing and scar formation after injury. To evaluate the efficacy of SynthoPlate (pristine or loaded with Gentamicin) to protect the wound from infection, a deep partial-thickness burn model will be used. Our models are based on preliminary data and experience with similarly modeled studies in the Chan (co-I) group. Pigs will be placed under anesthesia and deep partial-thickness burns will be created using a 300 g brass block coupled with a T-type thermocoupler (Omega, Stamford, Conn.). Once the burns have been created, either SynthoPlate alone or a SynthoPlate Gentamicin combination (mixed additively or Gentamicin loaded within SynthoPlate) will be applied to the wound. One high dose SynthoPlate-Gentamicin combination and one low dose combination will be used. On day 7 post-burn the pig will be euthanized and a superficial layer of skin will be harvested and both bacterial content and inflammatory markers will be analyzed. For the epithelialization studies, pigs will be placed under anesthesia and tangential excision wounds 56 $cm^2$ in area will be created using dermatome. Subsequently, either SynthoPlate alone or a SynthoPlate-Gentamicin combination (additively mixed or vesicle-loaded) will be applied to the wounds (untreated wounds used as controls). The wounds will be monitored every 7 days for 28 days. At each assessment additional treatments will be applied if needed. Altogether, we will demonstrate that SynthoPlate alone has beneficial effect on wound protection and inflammation, demonstrate that SynthoPlate-Gentamicin combinations provide wound protection and decrease inflammation by decreasing the bacterial burden and local inflammatory markers, respectively, and demonstrate that SynthoPlate™ alone, or with Gentamicin combination (additive or encapsulated within), has a beneficial effect on re-epithelialization of a wound Research Design and Methods All the SynthoPlate™ and control particle systems (pristine/empty and drugloaded) will be manufactured at scales needed for the various studies and provided to laboratories as needed.

Characterization of Biodistribution, Systemic Risks and Immune Response of Intravenously Administered SynthoPlate™ in Pigs Since the application of SynthoPlate™ is in emergency treatment of traumatic bleeding, we will first carry out 60 min time period studies on pharmacokinetics, biodistribution and systemic safety of SynthoPlate administered in healthy pigs without injury. Pigs will be injected with a bolus (full dose injected in <1 min) of SynthoPlate dose of $4 \times 10^6$ particles/kg (particle number approximately 5 logs below 30 kg porcine native platelet concentration of $4 \times 10^{11}$) and tested up to maximum dose of $4 \times 10^{11}$ particles/kg (particle number equivalent to porcine native platelet count) in 50 ml saline.

Manufacture of SynthoPlate

Figure 30:
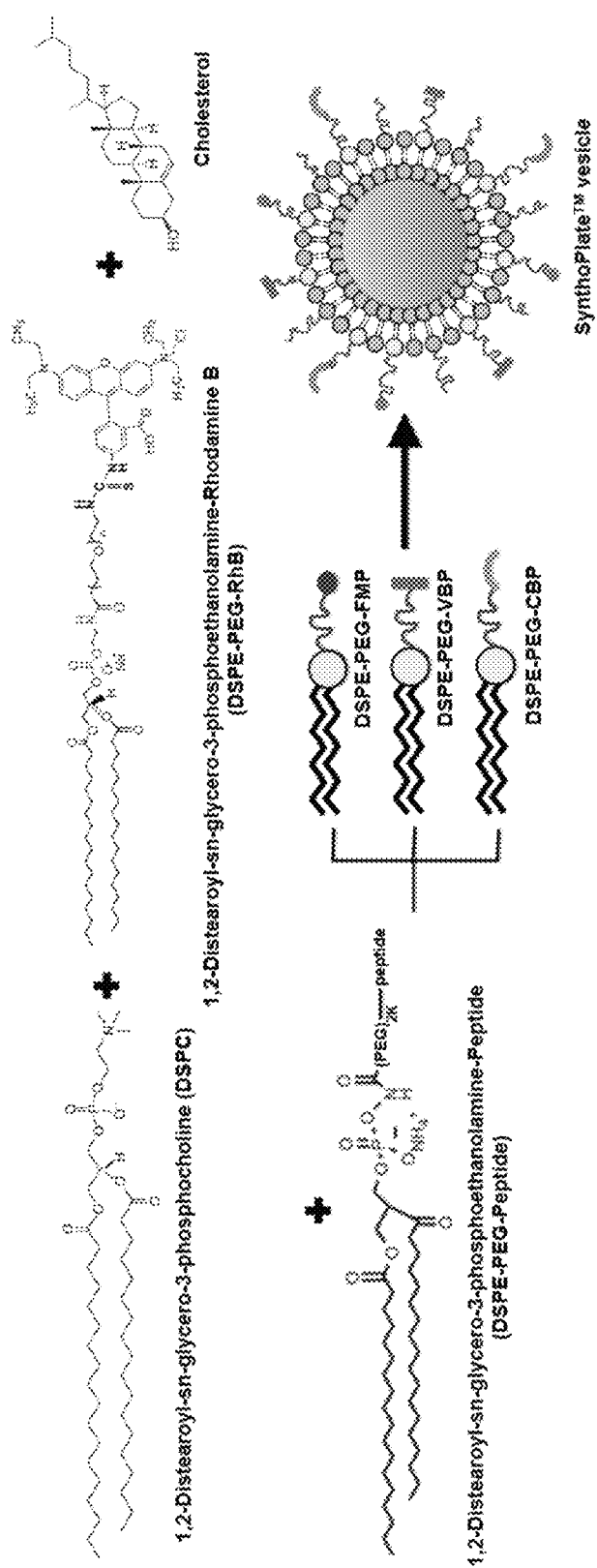
FIG. 30 illustrates a schematic showing components (with corresponding abbreviations) for SynthoPlate manufacture.

By virtue of our preliminary studies we have optimized the compositional design of the SynthoPlate™ vesicle. We have established that a total of 5 mol % incorporation of peptides (1.25 mol % VBP, 1.25 mol % CBP and 2.5 mol % FMP with respect to total lipid) results in a theoretical estimate of ~50,000 ligands decorations on the surface per vesicle, which is more than sufficient to render platelet-mimetic pro-adhesive and pro-aggregatory functions important in hemostasis. Therefore for all SynthoPlate™ systems to be used for the proposed studies, we will utilize 1.25 mol % of DSPE-PEG-VBP, 1.25 mol % of DSPE-PEG-CBP, 2.5 mol % of DSPE-PEG-FMP, 5 mol % of DSPE-PEG, 40 mol % Cholesterol, 49 mol % DSPC and 1 mol % DSPEE-PEG-Rhodamine B (red fluorescent probe), to make self-assembled liposomal vesicles using the reverse phase evaporation extrusion technique (schematic and abbreviations shown in FIG. 30). The DSPC content is to maintain vesicle stability at room temperature (DSPC melting temperature is ~55° C.) in storage, as well as, to impart the property of secreted Phospholipase A2 (sPLA2)-triggered membrane destabilization at the traumatic injury site for rapid release of encapsulated TXA payload (in studies where applicable).

The rationale for this release mechanism is based on the fact that activated platelets and leukocytes (phenotypic hallmarks of bleeding, vascular injury and inflammation) upregulate the secretion of enzyme PLA2, which can be leveraged as a stimulus for enzyme-triggered drug delivery. The cholesterol content is to maintain membrane integrity of the vesicle during in vivo circulation, and the PEG linker (with molecule weight 2000 Da) is to maintain reasonable circulation lifetime of the vesicles by minimizing rapid opsonization and macrophagic uptake. SynthoPlate vesicles thus prepared will be stored in saline suspensions or as lyophilized powder (reconstitutable in saline prior to I.V.-administration).

Characterization of Systemic Risks and Immune Response (if any)

The vitals, including invasive arterial blood pressure, heart rate, $SpO_2$, $CO_2$, and temperature will be monitored every 30 seconds for the first 10 minutes, then every minute for the next 20 minutes, then every 5 minutes for the last 30 minutes for anomalies that could be indicative of systemic risk. The skin will be monitored for the presence of urticaria, flushing, or other types of rash that could be suggestive of an immune response. Blood samples will be drawn at baseline, 5 minutes, 15 minutes, 30 minutes, and 1 hour to track the pigs' physiological response including arterial blood gas, and complete blood count. The blood will also be used to evaluate systemic pro-thrombotic risk via coagulation panel (PT and aPTT), ROTEM, D-dimer assay and aggregometry. The blood will also be used to run assays to detect complement activation components as markers of the pigs' immune response on SynthoPlate dosage. Specifically we will run immunoassays that will measure and quantify spectrophotometrically the complement components C3b, C5a and immunoglobulin. One hour after SynthoPlate administration, pigs will be euthanized and the major organs (heart, lungs, liver, spleen, kidneys, brain, and blood) will be harvested. Histology (H&E staining and fibrin-specific immunostaining) will be performed on sample sections of these organs to monitor for the presence of microvascular thrombi.

Characterization of Pharmacokinetics and Biodistribution

The Rhodamine B (RhB) fluorescence of the labeled SynthoPlate vesicles will be used to characterize their pharmacokinetics and biodistribution in the pig. For this, post-euthanasia, the harvested organs/tissues will be dried and homogenized at 4000 rpm using a BeadBug Microtube Homogenizer with 3.0 mm high impact zirconium beads. Homogenates will be shaken overnight at 750 rpm at 37° C. with a 1:1 solution of methanol/chloroform to extract the RhB-labeled lipids. Resultant samples will be centrifuged at 3,000 rpm for 10 minutes, the supernatant containing RhB-labeled lipids will be collected and the fluorescence in the supernatant will be determined using a fluorescence-based ultra-high performance liquid chromatography (UPLC) technique. Using this data, the SynthoPlate percentage in the organs listed at 60 minutes and in blood drawn at 5 minutes, 15 minutes, 30 minutes and 60 minutes will be determined by calculating the nanogram/ml of particles from a fluorescence calibration curve.

Number of Animals

For these studies we propose a sample size of 5 animals per group, with calculations based on p=0.05, power 0.9, assuming a standard deviation equal to half of the difference in our means. All of our groups would include the SynthoPlate™ maximum dose, max −1 log dose, max −3 log dose, max −5 log dose, and a saline comparison group. Therefore we propose an estimated total of 25 pigs for this study.

Evaluation of Hemostatic Efficacy of Pristine SynthoPlate™ and TXA-Loaded SynthoPlate™ in a Pig Model of Polytrauma Intra-cavitary, non-compressible hemorrhage is a leading cause of death and disability in military casualties. SynthoPlates provide an attractive and effective alternative to platelet transfusion as a pro-hemostatic entity that overcomes many of the potential shortcomings and eliminates the risks associated with autologous platelet transfusion. However, enthusiasm for TXA use is potentially tempered by a) small overall magnitude of benefit to mortality without significant changes in blood loss and b) concerns about off target and potential pro-thrombotic effects of administration of TXA. In order to overcome these concerns and potentially maximize the effect of TXA, we additionally propose to use SynthoPlates as a delivery vehicle for site-specific distribution of TXA. We believe that site-selective delivery of TXA to the site of hemorrhage via targeted action by SynthoPlates, will result in improved hemostasis in a swine model of polytrauma and uncontrolled hemorrhage. This model of polytrauma and hemostatic resuscitation is an adaptation of previously reported swine studies designed to model uncontrolled intracavitary hemorrhage.

Detailed Description of the Model

Figure 31:
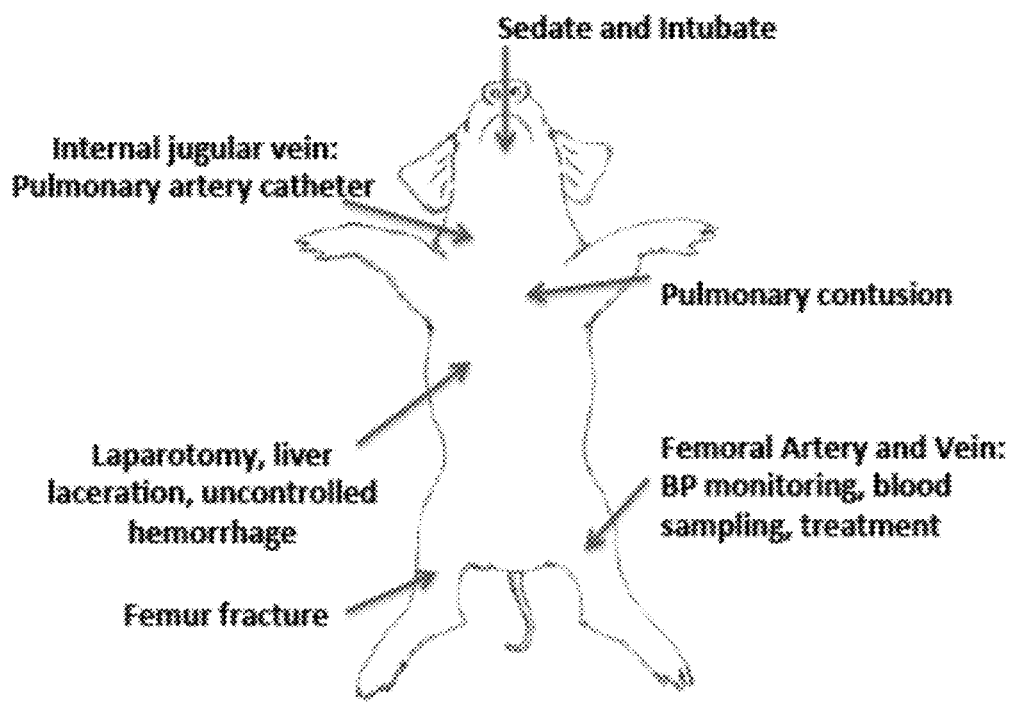
FIG. 31 illustrates a schematic showing a polytrauma model in pig.

Swine were chosen as the model for this study in order to achieve the desired endpoint of a large animal model with physiologic changes after hemorrhage that are similar to that seen in humans and represent a well validated species for the study of trauma and hemorrhage. Pigs will be subjected to hemorrhagic shock and standard resuscitation. Pigs will be anesthetized and cannulated. After cannulation the pigs will be subjected to polytrauma (FIG. 31) as follows: After the skin is prepped a small (1-2 mm) stab wound will be made through the skin, at the level of the left mid-femur, laterally using a #11 blade. A 25 gauge spinal needle will be inserted towards the mid shaft of the femur bone to assure the correct trajectory for firing the bolt gun at the mid femur. After firing the bolt gun (Schermer Stunner Model MKL, Karl Schermer and Co, Karlsruhe, Germany) the femur is broken at the level of the mid shaft. We will also fire the bolt gun without the use of a needle, on the chest of the animal at the level of the 5th intercostal space with midaxillary line, to produce a lung contusion. This results in a highly repeatable type of fracture and contusion, however it does not result in an open fracture. Additionally, due to the nature of the fracture, the musculature, the anesthetized and non-mobile state of the animal for the duration of the experiment, there is no need for splinting of the limb. We will also induce a 10 cm liver laceration. At this point, pigs will be administered intravenously with the following groups: SynthoPlate vs Control particles (particles with no peptide modification) by themselves, or, SynthoPlate vs Control particles mixed together in suspension with TXA, or, SynthoPlate vs Control particles loaded in the vesicle core with TXA (encapsulated in vesicle core). If the animal drops its mean arterial pressure below 40 mmHg, we will resuscitate with lactated ringer's (and the volume of resuscitation required will be quantified). After 30 minutes, we will pack the abdomen with a fixed number of pre-weighed laparotomy pads and close the abdomen. Hemodynamics are monitored continuously throughout the experiment. The pigs will be maintained in this shock state for a maximum of 90 minutes. At the end of 90 minutes or if the pig decompensates during this shock period, the pig will be resuscitated with a 1:1 volume of lactated ringer's to shed blood volume. Following this resuscitation, further resuscitation with lactated ringer's will be based upon comparison to baseline MAP and stroke volume variation determination from the indwelling Swan-Ganz catheter. The pigs will then be observed for up to 4 hours and several parameters will be assessed to evaluate hemostatic efficacy and resuscitation benefit of SynthoPlate™, as described below.

Assessment of Blood Loss and Hemostatic Efficacy of SynthoPlate-Based Resuscitation For each of the six types of treatment stated above, total shed blood volume will be determined by the change in weight of laparotomy pads placed within the abdominal cavity at the time of hemorrhage control and a post-mortem fixed volume peritoneal lavage to calculate the hematocrit of peritoneal shed blood. We will also quantify serum hemoglobin and hematocrit (iSTAT, Abbott, Princeton, N.J.), platelet count (Beckman Coulter Counter Pasadena, Calif.), prothrombin time (PT), partial thromboplastin time (PTT), international normalized ratio (INR) (STAGO, Start4 Analyzer, Diagnostica STAGO, Ramsey, Minnesotta), as well as viscoelastic coagulation measurement including thromboelastography (TEG) (Haemonetics, Braintree, Mass.). Fibrinolysis, especially in TXA groups, will be quantified by TEG, histologic staining for microvascular thromboses as we have described, and serum measurement of fibrinogen and D-dimer. All laboratory tests will be performed on a pre-trauma blood draw immediately prior to soft tissue trauma to establish a baseline so that each animal serves as its own internal control. Lab assessments will be repeated at serial time points post-trauma: 30 minutes, and each hour up to the point of sacrifice (total 6 time points per pig including baseline).

Determine the Effect of SynthoPlate ±TXA Treatment on Platelet Function Following Trauma At the time points noted above, we will analyze platelet function using three separate assays. Whole blood platelet aggregometry (Chronolog) will be performed using a low dose collagen (2 μg) as an agonist and area under the curve (AUC) will be quantified. Platelet rich plasma will be harvested and washed platelets will be analyzed for activation markers (CD62p, CD42) as well as for the formation of pro-coagulant platelet derived microparticles using sorting for CD41 and CD62p with size filtration using <1 uM microbeads as a size reference control. Finally, we will test the influence of SynthoPlate ±TXA resuscitation under flow conditions with arterial shear stress conditions. Blood collected at serial time points will be perfused over a collagen impregnated flow chamber and the rate and density of thrombus formation will be quantified.

Analysis of Organ Injury and Systemic Inflammation Following SynthoPlate ±TXA Treatment It is believed that improved hemostasis and potential anti-inflammatory effects of TXA will result in a reduction in end organ injury and systemic inflammation following polytrauma and hemorrhage. To this end, serum cytokines will be measured by Luminex, and the lung, liver, and kidney will be analyzed using histology techniques (H&E and immunostaining) for evidence of injury. Specifically we will measure platelet sequestration (CD41), platelet-neutrophil aggregates (CD41-Ly6G) (REF), and SynthoPlate sequestration (utilizing the pre-existing RhB fluorescent label on SynthoPlates).

Number of Animals/Data Analysis/Statistical Analysis

Groups to be tested (number of animals): Sham (3), resuscitation as above; Control Particles (7); Control Particles+TXA (7); SynthoPlate (7); SynthoPlate+TXA (7). For these studies we will use a sample size of 7 animals per experimental group, with calculations based on p=0.05, power 0.9, assuming a standard deviation equal to half of the difference in our means. These calculations are based on preliminary assays in the swine model indicating that the anticipated blood loss mirrors the distribution of blood loss in our murine polytrauma model, where robust reproducible studies indicate N=7 is sufficient to detect the differences between groups. Data collection time points are included in the individual experiments above, and data collection termination will occur at the time of planned sacrifice of the animal or if unanticipated mortality occurs. The primary endpoints will be quantification of intraperitoneal shed blood and change in serum hemoglobin at the end of the experiment. Secondary endpoints are outlined above. Data will be collected using a previously established Excel data collection sheet which includes automatic downloads of physiologic data collected throughout the experiment, and data will be compared using ANOVA. Outliers will be defined and excluded as those points greater than or equal to two standard deviations from the mean.

Evaluation of the Efficacy of SynthoPlate™ Alone or in Combination with Gentamicin to Provide Wound Protection and Improve Re-Epithelialization in Porcine Wound Models Inflammation and infection have profound effects on wound healing, re-epithelialization and scar formation. Scar formation after a burn poses a difficult clinical problem as it has overwhelming physiological and psychological effects on the individual injured. Additionally, it is not uncommon for burn wounds to develop hypertrophic scars and contractures while healing due to the robust immune response. Depending on the specific location, these scars and contractures can be disfiguring, cause significant pain and even limit function. On top of all this, development of an infection at the injury site not only delays wound healing but also has a significant impact on the eventual scar. Due to these issues, there has been extensive research on methods to regulate the immune response, improve wound healing and limit scar formation. The use of the SynthoPlate provides an attractive way of protecting the wound from infection while assisting epithelialization in effort to improve final outcomes. We believe that the use of SynthoPlate alone or in combination with Gentamicin will protect the wound from infection and decrease local inflammation. In turn this will improve wound re-epithelialization, wound healing and resultant scar formation. Demonstration of feasibility and efficacy in this aspect will also help expand the application of SynthoPlate as a wound-targeted delivery platform for spatio-temporally regulated release of cytokines and growth factors that further improve wound healing and reduce scar formation. To that end, we envision that SynthoPlate can become a customizable synthetic version of PRP therapy Burn Model Description Prior to inflicting any injury, the swine will be placed under general anesthesia and their back shaved and depilated to remove any remaining hair. Pre-operative markings will then be made with an electric tattoo marker (Superior Tattoo, Phoenix, Ariz.). Once the tattoos are created, the surgical field will be prepped in a standard fashion using povidone-iodine solution. Subsequently, 30 partial thickness burns encompassing a total of 270 $cm^2$ will be created along with two growth controls (total of 60 wounds between 2 pigs). Each wound will be approximately 2 cm apart (FIG. 32). This will be performed using a 300 g brass block coupled with a T-type thermocoupler (Omega, Stamford, Conn.) (FIG. 32B). The block will be heated to 100° C. and placed over the site of interest (lateral to spine). Based on prior studies performed in our lab, 15 seconds is the optimal duration to achieve a deep partial-thickness injury. Once the injuries have been created, the SynthoPlate alone, or in combination with Gentamicin will be applied to the wounds. On post-burn day 7, the pig will be euthanized, the superficial skin harvested and analyzed for CFU and 16S-RNA to assess bacterial burden. Additionally, inflammatory cytokines will be analyzed via appropriate biochemistry techniques (PCR, ELISA and immunoasays) from tissue homogenates.

Tangential Excision Model Description

Similar to the above burn model, the pig will be placed under general anesthesia, all hair removed and prepped and draped in the standard sterile fashion. We will use a dermatome and create ten, 56 cm2, tangential excision wounds (FIG. 33). Each wound will be created by two passing's of the dermatome set at $^{30}/_{1000}$ in. Five of the wounds will be standard of care controls while the remaining five are treated with either SynthoPlate alone or SynthoPlate in combination with Gentamicin. The treatment that is chosen will depend on the results of the burn model. We will plan to utilize whichever treatment provided optimal results and reapply this during each assessment. In contrast to the burn model, these pigs will be monitored for 28 days with wound assessments on days 7, 14, 21 and 28. Wounds will be assessed both clinically and histologically. Photographs will be taken at each assessment and on day 28 biopsies will be taken for histopathology.

Number of Animals/Statistical Analysis

A total of 4 Yorkshire-Duroc hybrid pigs will be utilized in this portion of the study. We will use 2 pigs (total of 60 wounds) for the burn model and 2 pigs (total of 20 wounds) for the tangential excision model. Differences between groups will be analyzed by two-way ANOVA, unless otherwise indicated. P-values below 0.05 will be considered significant. Power analysis concluded that 10 samples per group are sufficient for a power set at 80% and a type-1 error rate of 0.05.

From the above description of the invention, those skilled in the art will perceive improvements, changes and modifications. Such improvements, changes, and modifications are within the skill of the art and are intended to be covered by the appended claims. All patents, patent applications, and publications cited herein are incorporated by reference in their entirety.

---

Having described the invention, we claim:

1. A method of treating a traumatic brain injury (TBI) in a gyrencephalic mammalian subject, the method comprising:
administering to a gyrencephalic mammalian subject a synthetic platelet comprising a biocompatible flexible liposome nanoparticle and a therapeutic agent, wherein the therapeutic agent is encapsulated by the biocompatible flexible liposome nanoparticle, wherein the biocompatible flexible liposome nanoparticle comprises distearyl phosphatidyl ethanolamine (DSPE), distearyl phosphatidyl choline (DSPC), and cholesterol,
wherein the synthetic platelet includes an outer surface, a plurality of peptides conjugated to the surface, the peptides including a plurality of brain injury site-targeting peptides having SEQ ID NO: 6 (CAQK), wherein the synthetic platelet adheres to a brain injury site and promotes delivery of the therapeutic agent onto sites of the brain injury, wherein the therapeutic agent is released at the site of brain injury via a site-relevant enzyme, and wherein the brain injury site-targeted peptides are spatially or topographically arranged on the biocompatible flexible liposome nanoparticle surface such that the brain injury site-targeted peptides do not spatially mask each other, and wherein the biocompatible flexible liposome nanoparticle shape, size and elastic modulus facilitates margination to a vascular wall and their bio-interactions upon administration to a vasculature of the subject.

2. The method of claim 1, wherein the therapeutic agent is administered in an amount effective to reduce intracerebral microvascular thrombosis and/or decrease cerebral injury size.

3. The method of claim 1, wherein the therapeutic agent comprises a neuroprotective therapeutic agent selected from the group consisting of brain-derived neurotrophic factor (BDNF), glial cell line-derived neurotrophic factor (GDNF), nerve growth factor (NGF), ciliary neurotrophic factor (CNTF), and combinations thereof.

4. The method of claim 1, wherein the site-relevant enzyme is phospholipase A2 (PLA2).

5. The method of claim 1, wherein the biocompatible flexible liposome nanoparticle consists of distearyl phosphatidyl ethanolamine (DSPE), distearyl phosphatidyl choline (DSPC), and cholesterol.

6. The method of claim 5, wherein the DSPE of the liposome nanoparticle is conjugated to the brain injury site-targeting peptides via a polyethylene glycol (PEG) linker.

7. The method of claim 6, wherein the liposome nanoparticle comprises about 5 mol % of a DSPE-PEG-CAQK conjugate.

8. The method of claim 1, wherein the therapeutic agent is cerebrolysin.

9. A method of treating a traumatic brain injury (TBI) in a gyrencephalic mammalian subject, the method comprising:
administering to a gyrencephalic mammalian subject a synthetic platelet comprising a biocompatible flexible liposome nanoparticle and cerebrolysin, wherein the cerebrolysin is encapsulated by the biocompatible flexible liposome nanoparticle, wherein the biocompatible flexible liposome nanoparticle comprises distearyl phosphatidyl ethanolamine (DSPE), distearyl phosphatidyl choline (DSPC), and cholesterol,
wherein the synthetic platelet includes an outer surface, a plurality of peptides conjugated to the surface, the peptides including a plurality of brain injury site-targeting peptides having SEQ ID NO: 6 (CAQK), wherein the synthetic platelet adheres to a brain injury site and promotes delivery of the cerebrolysin onto sites of the brain injury, and wherein the cerebrolysin is released at the site of brain injury via a site-relevant enzyme, and wherein the brain injury site-targeted peptides are spatially or topographically arranged on the biocompatible flexible liposome nanoparticle surface such that the brain injury site-targeted peptides do not spatially mask each other, and wherein the biocompatible flexible liposome nanoparticle shape, size and elastic modulus facilitates margination to a vascular wall and their bio-interactions upon administration to a vasculature of the subject.

* * * * *